United States Patent
Pordy et al.

(10) Patent No.: US 10,772,956 B2
(45) Date of Patent: Sep. 15, 2020

(54) METHODS FOR REDUCING OR ELIMINATING THE NEED FOR LIPOPROTEIN APHERESIS IN PATIENTS WITH HYPERLIPIDEMIA BY ADMINISTERING ALIROCUMAB

(71) Applicant: Regeneron Pharmaceuticals, Inc., Tarrytown, NY (US)

(72) Inventors: Robert C. Pordy, Ardsley, NY (US); Garen Manvelian, White Plains, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 245 days.

(21) Appl. No.: 15/238,890

(22) Filed: Aug. 17, 2016

(65) Prior Publication Data

US 2017/0049886 A1     Feb. 23, 2017

Related U.S. Application Data

(60) Provisional application No. 62/206,326, filed on Aug. 18, 2015, provisional application No. 62/264,361, filed on Dec. 8, 2015, provisional application No. 62/270,790, filed on Dec. 22, 2015, provisional application No. 62/291,571, filed on Feb. 5, 2016, provisional application No. 62/311,455, filed on Mar. 22, 2016, provisional application No. 62/367,374, filed on Jul. 27, 2016.

(51) Int. Cl.
| | | |
|---|---|---|
| A61K 39/395 | (2006.01) | |
| A61K 35/413 | (2015.01) | |
| C07K 16/40 | (2006.01) | |
| A61M 1/34 | (2006.01) | |
| A61K 31/397 | (2006.01) | |
| A61K 31/455 | (2006.01) | |
| A61K 39/00 | (2006.01) | |

(52) U.S. Cl.
CPC ........ *A61K 39/3955* (2013.01); *A61K 31/397* (2013.01); *A61K 31/455* (2013.01); *A61K 35/413* (2013.01); *A61K 39/395* (2013.01); *A61M 1/3496* (2013.01); *C07K 16/40* (2013.01); *A61K 2039/505* (2013.01); *A61K 2039/54* (2013.01); *A61K 2039/545* (2013.01); *A61M 1/34* (2013.01); *A61M 2205/33* (2013.01); *C07K 2317/21* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,260,440 A | 11/1993 | Hirai |
| 5,273,995 A | 12/1993 | Roth |
| 5,399,670 A | 3/1995 | Bhattacharya |
| 5,851,999 A | 12/1998 | Ulrich |
| 5,939,598 A | 8/1999 | Kucherlapati |
| 6,011,003 A | 1/2000 | Charmock-Jones |
| 6,171,586 B1 | 1/2001 | Lam |
| 6,267,958 B1 | 7/2001 | Andya |
| 6,270,993 B1 | 8/2001 | Shibuya |
| 6,596,541 B2 | 7/2003 | Murphy |
| 6,629,949 B1 | 10/2003 | Douglas |
| 6,659,982 B2 | 12/2003 | Douglas |
| 6,875,432 B2 | 4/2005 | Liu |
| 7,001,892 B1 | 2/2006 | Chmielweski |
| 7,029,895 B2 | 4/2006 | Glucksmann |
| 7,060,268 B2 | 6/2006 | Andya |
| 7,129,338 B1 | 10/2006 | Ota |
| 7,300,754 B2 | 11/2007 | Fadel |
| 7,482,147 B2 | 1/2009 | Glucksmann |
| 7,572,618 B2 | 8/2009 | Mintier |
| 7,608,693 B2 | 10/2009 | Martin |
| 7,754,208 B2 | 7/2010 | Ledbetter |
| 8,030,457 B2 | 10/2011 | Jackson |
| 8,062,640 B2 | 11/2011 | Sleeman |
| 8,080,243 B2 | 12/2011 | Liang |

(Continued)

FOREIGN PATENT DOCUMENTS

| | | |
|---|---|---|
| CN | 101489565 | 7/2009 |
| EP | 0521471 | 10/2000 |

(Continued)

OTHER PUBLICATIONS

Bambauer et al. (The Scientific World Journal, 2012, Article ID 314283, pp. 1-19) (Year: 2012).*
Abifadel, et al. (2003) Nature Genetics 34(2):154-156, "Mutations in PCSK9 cause autosomal dominant hypercholesterolemia".
Abifadel, et al., 2009 Human Mutation 30(4):520-529, "Mutations and polymorphisms in the proprotein convertase subtilisin kexin 9 (PCSK9) gene in cholesterol metabolism and disease".
Abifadel, et al., 2012 Atherosclerosis 223(2):394-400, "Identification and characterization of new gain-of-function mutations in the PCSK9 gene responsible for autosomal dominant hypercholesterolemia".
Alborn, et al. (2007) Clinical Chemistry 53(10):1814-1819, "Serum proprotein convertase subtilisin Kexin type 9 is correlated directly with serum LDL cholesterol".

(Continued)

*Primary Examiner* — Sharon X Wen
(74) *Attorney, Agent, or Firm* — Lathrop GPM LLP; James H. Velema, Esq.

(57) ABSTRACT

The present invention provides methods for reducing or eliminating a patient's need for lipoprotein apheresis therapy. The methods of the present invention comprise administering to a patient a pharmaceutical composition comprising a PCSK9 inhibitor. In certain embodiments, the PCSK9 inhibitor is an anti-PCSK9 antibody. The methods of the present invention are useful for treating patients with hyperlipidemia and related conditions who are currently being treated with a therapeutic regimen comprising lipoprotein apheresis (e.g., LDL apheresis or Lp(a) apheresis).

17 Claims, 8 Drawing Sheets

Specification includes a Sequence Listing.

(56) References Cited

U.S. PATENT DOCUMENTS

| | | | |
|---|---|---|---|
| 8,092,803 B2 | 1/2012 | Furfine | |
| 8,168,762 B2 | 5/2012 | Jackson | |
| 8,188,233 B2 | 5/2012 | Condra | |
| 8,188,234 B2 | 5/2012 | Condra | |
| 8,357,371 B2 | 1/2013 | Sleeman | |
| 8,501,184 B2 | 8/2013 | Sleeman | |
| 8,795,669 B2 | 8/2014 | Dix | |
| 8,829,165 B2 | 9/2014 | Jackson | |
| 8,883,157 B1 | 11/2014 | Clube | |
| 8,945,560 B1* | 2/2015 | Clube | C07K 16/40 424/130.1 |
| 9,034,332 B1 | 5/2015 | Clube | |
| 9,127,068 B2 | 9/2015 | Okamoto | |
| 9,193,801 B2 | 11/2015 | Walsh | |
| 9,358,287 B2 | 6/2016 | Harp | |
| 9,540,449 B2 | 1/2017 | Yancopoulos | |
| 9,550,837 B2* | 1/2017 | Sleeman | C07K 16/40 |
| 10,023,654 B2 | 7/2018 | Sleeman | |
| 2003/0092606 A1 | 5/2003 | L'Italien | |
| 2003/0113316 A1 | 6/2003 | Kaisheva | |
| 2003/0118592 A1 | 6/2003 | Ledbetter | |
| 2003/0133939 A1 | 7/2003 | Ledbetter | |
| 2004/0101920 A1 | 5/2004 | Radziejewski | |
| 2004/0197324 A1 | 10/2004 | Liu | |
| 2005/0281831 A1 | 12/2005 | Davis-Smyth | |
| 2006/0147945 A1 | 7/2006 | Edmonds | |
| 2007/0082345 A1 | 4/2007 | Ota | |
| 2007/0224663 A1 | 9/2007 | Rosen | |
| 2008/0008697 A1 | 1/2008 | Mintier | |
| 2009/0142352 A1 | 6/2009 | Jackson | |
| 2009/0232795 A1 | 9/2009 | Condra | |
| 2009/0246192 A1 | 10/2009 | Condra | |
| 2009/0269350 A1 | 10/2009 | Glucksmann | |
| 2009/0318536 A1 | 12/2009 | Freier | |
| 2009/0326202 A1 | 12/2009 | Jackson | |
| 2010/0040610 A1 | 2/2010 | Sitlani | |
| 2010/0040611 A1 | 2/2010 | Sparrow | |
| 2010/0041102 A1 | 2/2010 | Sitlani | |
| 2010/0068199 A1 | 3/2010 | Liang | |
| 2010/0136028 A1 | 6/2010 | Sparrow | |
| 2010/0150937 A1 | 6/2010 | Sparrow | |
| 2010/0166768 A1 | 7/2010 | Sleeman | |
| 2010/0233177 A1 | 9/2010 | Yowe | |
| 2011/0027287 A1 | 2/2011 | Jackson | |
| 2011/0033465 A1 | 2/2011 | Hedrick | |
| 2011/0065902 A1 | 3/2011 | Sleeman | |
| 2011/0098450 A1 | 4/2011 | Igawa | |
| 2011/0111406 A1 | 5/2011 | Igawa | |
| 2011/0142849 A1 | 6/2011 | Rue | |
| 2011/0171241 A1 | 7/2011 | Dix | |
| 2011/0229489 A1 | 9/2011 | Pons | |
| 2011/0256148 A1 | 10/2011 | Sleeman | |
| 2012/0014951 A1 | 1/2012 | Liang | |
| 2012/0015435 A1 | 1/2012 | Liang | |
| 2012/0020975 A1 | 1/2012 | Jackson | |
| 2012/0027765 A1 | 2/2012 | Jackson | |
| 2012/0076799 A1 | 3/2012 | Sparrow | |
| 2012/0077964 A1 | 3/2012 | Sparrow | |
| 2012/0082679 A1 | 4/2012 | Sparrow | |
| 2012/0082680 A1 | 4/2012 | Sitlani | |
| 2012/0093818 A1 | 4/2012 | Jackson | |
| 2012/0097565 A1 | 4/2012 | Dix | |
| 2012/0195910 A1 | 8/2012 | Wu | |
| 2012/0213794 A1 | 8/2012 | Luo | |
| 2012/0213797 A1 | 8/2012 | Jackson | |
| 2012/0219558 A1 | 8/2012 | Ni | |
| 2012/0231005 A1 | 9/2012 | Luo | |
| 2012/0251544 A1 | 10/2012 | Jackson | |
| 2013/0011866 A1 | 1/2013 | Igawa | |
| 2013/0064825 A1 | 3/2013 | Chan et al. | |
| 2013/0064834 A1 | 3/2013 | Sleeman | |
| 2013/0085266 A1 | 4/2013 | Sleeman | |
| 2013/0243784 A1 | 9/2013 | Swergold | |
| 2014/0004122 A1 | 1/2014 | Chan | |
| 2014/0099312 A1 | 4/2014 | Sleeman | |
| 2014/0161821 A1 | 6/2014 | Udata | |
| 2014/0356370 A1 | 12/2014 | Swergold | |
| 2014/0356371 A1 | 12/2014 | Swergold | |
| 2015/0140002 A1 | 5/2015 | Baccara-Dinet | |
| 2015/0152191 A1 | 6/2015 | Baccara-Dinet | |
| 2015/0231236 A1 | 8/2015 | Pordy | |
| 2015/0283236 A1 | 10/2015 | Baccara-Dinet | |
| 2015/0284473 A1 | 10/2015 | Bessac | |
| 2016/0032015 A1 | 2/2016 | Walsh et al. | |
| 2016/0152734 A1 | 2/2016 | Udata | |
| 2017/0096496 A1 | 4/2017 | Sleeman | |
| 2017/0296657 A1 | 10/2017 | Sleeman | |
| 2018/0044436 A1 | 2/2018 | Walsh et al. | |
| 2018/0296675 A1 | 10/2018 | Coleman et al. | |
| 2018/0333490 A1 | 11/2018 | Swergold | |
| 2019/0135941 A1 | 5/2019 | Sleeman | |
| 2019/0284301 A1 | 9/2019 | Walsh | |
| 2019/0330371 A1 | 10/2019 | Swergold | |

FOREIGN PATENT DOCUMENTS

| | | |
|---|---|---|
| EP | 1067182 | 1/2001 |
| EP | 0409281 | 10/2001 |
| EP | 1514933 | 3/2005 |
| EP | 1317537 | 12/2006 |
| EP | 1618212 | 11/2007 |
| EP | 2 703 008 | 8/2012 |
| EP | 2 703 009 | 8/2012 |
| EP | 2 706 070 | 3/2014 |
| WO | WO 1993/000807 | 1/1993 |
| WO | WO 97/035620 | 10/1997 |
| WO | WO 98/22136 | 5/1998 |
| WO | WO 99/38495 | 8/1999 |
| WO | WO 2001/057081 | 8/2001 |
| WO | WO 2004/055164 | 7/2004 |
| WO | WO 2004/097047 | 11/2004 |
| WO | WO 2005/103081 | 11/2005 |
| WO | 2007/146511 | 12/2007 |
| WO | WO 2007/149334 | 12/2007 |
| WO | WO 2008/057457 | 5/2008 |
| WO | WO 2008/057458 | 5/2008 |
| WO | WO 2008/057459 | 5/2008 |
| WO | WO 2008/063382 | 5/2008 |
| WO | 2008066776 A2 | 6/2008 |
| WO | WO 2008/125623 | 10/2008 |
| WO | 2008138536 A2 | 11/2008 |
| WO | WO 2008/133647 | 11/2008 |
| WO | WO 2008/138536 | 1/2009 |
| WO | WO 2009/026558 | 2/2009 |
| WO | WO 2009/042765 | 4/2009 |
| WO | WO 2009/055783 | 4/2009 |
| WO | WO 2009/100297 | 8/2009 |
| WO | WO 2009/100318 | 8/2009 |
| WO | WO 2010/029513 | 3/2010 |
| WO | WO 2010/032220 | 3/2010 |
| WO | WO 2010/077854 | 7/2010 |
| WO | WO 2010/102241 | 9/2010 |
| WO | WO 2010/148337 | 12/2010 |
| WO | WO 2011/028938 | 3/2011 |
| WO | WO 2011/039578 | 4/2011 |
| WO | WO 2011/053759 | 5/2011 |
| WO | WO 2011/061712 | 5/2011 |
| WO | WO 2011/072263 | 6/2011 |
| WO | WO 2011/111007 | 9/2011 |
| WO | WO 2012/054438 | 4/2012 |
| WO | WO 2012/064792 | 5/2012 |
| WO | WO 2012/101251 | 8/2012 |
| WO | WO 2012/101252 | 8/2012 |
| WO | WO 2012/101253 | 8/2012 |
| WO | WO 2012/109530 | 8/2012 |
| WO | WO 2012/146776 | 11/2012 |
| WO | WO 2012/154999 | 11/2012 |
| WO | WO 2013/039958 | 3/2013 |
| WO | WO 2013/039969 | 3/2013 |
| WO | WO 2013/158984 | 10/2013 |
| WO | 2013/169886 | 11/2013 |
| WO | 2013/177536 | 11/2013 |
| WO | WO 2013/166448 | 11/2013 |
| WO | WO 2014/194111 | 12/2014 |

(56) References Cited

FOREIGN PATENT DOCUMENTS

| WO | WO 2014/197752 | 12/2014 |
|---|---|---|
| WO | WO 2011/117401 | 3/2015 |
| WO | WO 2015/054619 | 4/2015 |
| WO | WO 2015/073494 | 5/2015 |
| WO | WO 2015/123423 | 8/2015 |
| WO | WO 2015/140079 | 9/2015 |
| WO | WO 2015/142668 | 9/2015 |
| WO | WO 2016/011256 | 1/2016 |
| WO | WO 2016/011260 | 1/2016 |

OTHER PUBLICATIONS

Almagro et al., 'Humanization of antibodies.' Frontiers in Bioscience. 2008, vol. 13, pp. 1619-1633.
Al-Mashhadi et al., 2013 Science Translation Medicine, American Association for the Advancement of Science 5(166):44-53, "Atherosclerosis: Familial hypercholesterolemia and atherosclerosis in clones minipigs created by DNA transposition of a human PCSK9 gain-of-function mutant".
Altschul et al., 'Basic local alignment search tool.' Journal of Molecular Biology. 1990, vol. 215, No. 3, pp. 403-410.
Altschul et al., 'Gapped BLAST and PSI-BLAST: a new generation of protein database search programs.' Nucleic Acids Research. 1997, vol. 25, No. 17, pp. 3389-3402.
AMGEN: 'Ascending Multiple Dose Study to Evaluate the Safety, Tolerability, Pharmacokinetics and Pharmacodynamics of AMG 145 in Subjects With Hyperlipidemia on Stable Doses of a Statin'. May 27, 2010, XP002682099. Retrieved from the Internet: URL:http://clinicaltrials.gov/ct2/show/nct01133522?term=amg+145&rank=2 Accessed on Aug. 6, 2014.
Angal et al., 'A single amino acid substitution abolishes the heterogeneity of chimeric mouse/human (IgG4) antibody.' Molecular Immunology. 1993, vol. 30, No. 1, pp. 105-108.
Annex to Form PCT/ISA/206—Communication Relating to the Results of the Partial International Search for PCT/US2009/068013, dated Mar. 10, 2010.
Anonymous: A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome. Archive from ClinicalTrials.gov for NCT01663402 on Mar. 11, 2014 (3 pages).
Anonymous: Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study. Archive from ClinicalTrials.gov for NCT01507831 on Jun. 27, 2013 (3 pages).
Anthem (Sep. 21, 2015) "Proprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016].
Attie and Seidah (2005) Cell Metabolism 5:290-292, "Dual regulation of the LDL receptor—Some clarity and new questions".
Bambauer R., et al. (2003) Therapeutic Apheresis and Dialysis 7(4):382-390 Low-density Lipoprotein Apheresis: An Overview.
Barbie and Lefranc, 1998 Exp. Clin. Immunogenet. 15:171-183, "The Human Immunoglobulin Kappa Variable (IGKV) Genes and Joining (IGKJ) Segments".
Bays H, Farnier M, Gaudet D, Weiss R, Lima Ruiz J, Watts GF, Gouni-Berthold I, Robinson J, Jones P, Severance R, Averna M, Steinhagen-Thiessen E, Colhoun HM, Zhao J, Du Y, Hanotin C, Donahue S. Efficacy and safety of combining alirocumab with atorvastatin or rosuvastatin versus statin intensification or adding ezetimibe in high cardiovascular risk patients: ODYSSEY Options I and II. Circulation. 2014;130:2105-2126.
Bays H; Gaudet D; Weiss R; Lima Ruiz J; Watts GF; Gouni-Berthold I; Robinson J; Zhao J; Hanotin C; Donahue S. PCSK9 Inhibitor Alirocumab as Add-on to Atorvastatin versus Other Lipid Treatment Strategies in Patients at High CVD Risk: ODYSSEY Options I. Circulation. 2014;130:A16194.
Bee, et al. (2009) Journal of Pharmaceutical Sciences 98(9): 3290-3301, "Precipitation of a monoclonal antibody by soluble tungsten".
Benjannet, et al. (2006) J. Biological Chemistry 281(41): 30561-30572, "The Proprotein Convertase (PC) PCSK9 is Inactivated by Furin and/or PC5/6A".
Bird et al., 'Single-chain antigen-binding proteins.' Science. 1988, vol. 242, No. 4877, pp. 423-426.
Blom, Dirk J. et al.: "A 52-Week Placebo-Controlled Trial of Evolocumab in Hyperlipidemia" vol. 370, No. 19, May 8, 2014 pp. 1809-1819.
Borberg, H. (2013) Transfusion and Apheresis Science 48:203-206.
Breen, et al. (2001) Pharmaceutical Research 18(9): 1345-1353, "Effect of moisture on the stability of a lyophilized humanized monoclonal antibody formulation".
Cannon CP, Cariou B, Blom D, McKenney JM, Lorenzato C, Pordy R, Chaudhari U, Colhoun HM. Efficacy and safety of alirocumab in high cardiovascular risk patients with inadequately controlled hypercholesterolaemia on maximally tolerated daily statin: results from the ODYSSEY COMBO II study; presented at ESC Congress Aug. 31, 2014, abstract not published.
Cannon CP, Cariou B, Blom D, McKenney JM, Lorenzato C, Pordy R, Chaudhari U, Colhoun HM; for the Odyssey Combo II Investigators. Efficacy and safety of alirocumab in high cardiovascular risk patients with inadequately controlled hypercholesterolaemia on maximally tolerated doses of statins: the ODYSSEY COMBO II randomized controlled trial Eur Heart J. 2015. doi:10.1093/eurheartj/ehv028 [epub ahead of print].
Carpenter, 1997 Pharm. Res. 14(8): 969-975, Rational Design of Stable Lyophilized Protein Formulations: Some Practical Advice.
Catapano AL, Papadopoulos N. The safety of therapeutic monoclonal antibodies: implications for cardiovascular disease and targeting the PCSK9 pathway. Atherosclerosis 2013;228(1):18-28.
Chan, et al. (2009) PNAS 106(24):9820-9825, "A proprotein convertase subtilisin/kexin type 9 neutralizing antibody reduces serum cholesterol in mice and nonhuman primates".
Chaparro-Riggers, et al. (2012) J. Biological Chemistry 287(14):11090-11097, "Increasing serum half-life and extending cholesterol lowering in vivo by engineering antibody with pH-sensitive binding to PCSK9".
Chinese Patent Application No. 201280015477.6, Office Action dated Dec. 2, 2014 with English summary, 12 pages.
Chinese Patent Application No. 201280015571.1, Office Action dated Sep. 3, 2014 with English summary, 12 pages.
ClinicalTrials.gov archive; A Randomized, Double-Blind, Placebo-Controlled, Parallel-Group Study to Evaluate the Efficacy and Safety of Alirocumab in Patients With Heterozygous Familial Hypercholesterolemia Undergoing Lipid Apheresis Therapy 2014; 4 pgs.
Colhoun HM, Robinson JG, Farnier M, Cariou B, Blom D, Kereiakes DJ, Lorenzato C, Pordy R, Chaudhari U. Efficacy and safety of alirocumab, a fully human PCSK9 monoclonal antibody, in high cardiovascular risk patients with poorly controlled hypercholesterolemia on maximally tolerated doses of statins: rationale and design of the ODYSSEY COMBO I and II trials. BMC Cardiovasc Disord. 2014;14(1):121.
Costet. PCSK9 inhibitors as LDL cholesterol-lowering agents: Rationale, concerns and preliminary outcomes. Drugs of the Future. May 1, 2012. vol. 37, No. 5, pp. 331-341.
Daugherty, et al., 2006 Advanced Drug Delivery Reviews 58: 686-706, "Formulation and delivery issues for monoclonal antibody therapeutics".
Davidson et al. (2011) Journal of Clinical Lipidology 5:338-367, "Clinical utility of inflammatory markers and advanced lipoprotein testing: Advice from an expert panel of lipid specialists".
Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Abstract of a presentation presented at the 81st European Atherosclerosis Society (EAS) Congress, Jun. 2-5, 2013, Lyon, France.

(56) References Cited

OTHER PUBLICATIONS

Dube, et al. (2012) Curr Opin Lipidol 23(2):133-140, "Lipoprotein(a): more interesting than ever after 50 years".

Duff et al. Biochem Journal, the Biochemical Society, vol. 419, No. 3, May 1, 2009 pp. 577-584.

Dufour R, Moriarty PM, Genestin E, Sasiela WJ, Du Y, Ferrand A-C; Ginsberg HN. Effect of REGN727/SAR236553 PCSK9 fully human monoclonal antibody in patients with elevated triglycerides/ low high-density lipoprotein cholesterol: data from three phase 2 studies. Circulation 2012;126:Abstract A16127.

European Patent Application No. 12701015.5, Communication pursuant to Article 94(3) EPC dated Apr. 24, 2015, 9 pages.

European Patent Application No. 12701015.5, Communication pursuant to Article 94(3) EPC dated May 30, 2014, 8 pages.

European Patent Application No. 12701742.4, Communication pursuant to Article 94(3) EPC dated Jun. 1, 2015, 10 pages.

Fallon, et al. (2000) J. Biological Chemistry 275(10):6790-6797, "Increased endosomal sorting of ligand to recycling enhances potency of an intereukin-2 analog".

Farnier M, Kastelein JJP, Roth E, Taskinen MR, Ginsberg HN, Colhoun HM, Robinson JG, Merlet L, Brunet A, Pordy R, Baccara-Dinet MT. Relationship between alirocumab, PCSK9 and LDL-C levels: results from the ODYSSEY MONO Phase 3 trial of alirocumab 75 mg every 2 weeks. Atherosclerosis. 2014;235(2):e34—e35. [Abstract MP02E].

Farnier, 2011 American Journal of Cardiovascular Drugs 11(3):145-152, "The role of proprotein convertase subtilisin/kexin type 9 in hyperlipidemia: Focus on therapeutic implications".

Fasano, et al., 2008 NMCD Nutrition Metabolism and Cardiovascular Diseases 18(1):S46, "45 Activity of Gain-of-Function PCSK9 Mutants on LDLR Correlates with Total-Cholesterol Values in ADH patients".

Foody J, Khan I, Lewis B. Attainment of low-density lipoprotein cholesterol goals in patients at high cardiovascular risk: results from a managed care population study. Circulation. 2013;128:A17254.

Foote and Winter (1992) J. Mol. Biol. 224:487-499, "Antibody Framework Residues Affecting the Conformation of the Hypervariable Loops".

Gaudet D, Kereiakes D, McKenney J, Roth E, Hanotin C, Gipe D, Du Y, Ferrand A-C, Ginsberg H, Stein E. Alirocumab, a fully human monoclonal antibody to PCSK9, reduces high plasma Lp(a) concentration: pooled analysis of 352 patients from phase 2. J Clin Lipidol 2013:7(3):283-284.

Gaudet D, Kereiakes D, McKenney J, Roth E, Hanotin C, Gipe D, Du Y, Ferrand A-C, Ginsberg H, Stein E. Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials). Am J Cardiol. 2014;114(5):711-715.

Gaudet D, Kereiakes D, McKenney J, Roth E, Hanotin C, Gipe D, Du Y, Ferrand A-C, Ginsberg H, Stein E. Effect of SAR236553/ REGN727 fully human monoclonal anti-proprotein convertase subtilisin/ kexin type 9 antibody on plasma lipoprotein(a) concentrations: pooled analysis from three phase 2 studies (NCT:01266876; 01288469; 01288443). Circulation 2012;126:Abstract A16125.

Ginsberg HN, Rader DJ, Raal FJ, Guyton JR, Lorenzato C, Pordy R, Baccara-Dinet MT, Stroes E. ODYSSEY HIGH FH: efficacy and safety of alirocumab in patients with severe heterozygous familial hypercholesterolemia. Circulation. 2014;130:2119.

Gonnet et al.: Exhaustive Matching of the Entire Protein Sequence Database; Science; 1992, vol. 256, pp. 1443-1445.

Grozdanov, et al. (2006) Biochem. Cell. Biol. 84:80-92, "Expression and localization of PCSK9 in rat hepatic cells".

Gusarova V, Howard VG, Okamoto H, Koehler-Stec EM, Papadopoulos N, Murphy AJ, Yancopoulos GD, Stahl N, Sleeman MW. Reduction of LDL cholesterol by a monoclonal antibody to PCSK9 in rodents and nonhuman primates. Clin Lipidol 2012;7(6):737-743.

Gusarova V, Sleeman M, Swergold G, Sasiela B, Stahl N, Yancopoulos G, Murphy A. Fully human antibody that blocks PCSK9 demonstrates reduction in LDL-C preclinically and in early clinical trials. Abstract of oral presentation at the Keystone Symposia on Molecular and Cellular Biology, Mar. 25-30, 2012, Montana, USA.

Haddley et al. ALIROCUMAB Anti-Proprotein Convertase 9 (PCSK9) Mab Treatment of Hypercholesterolemia. Drugs of the Future; Apr. 1, 2013. vol. 38, No. 4. pp. 215-216.

Heap et al., 'Analysis of a 17-amino acid residue, virus-neutralizing microantibody.' Journal of General Virology. 2005, vol. 86, No. 6, pp. 1791-1800.

Hiriyama et al. (Jan. 1, 2014) "Effects of evolocumab (AMG 145), a monoclonal antibody to PCSK9, in hypercholesterolemic, statin-treated Japanese patients at high cardiovascular risk—primary results from the phase 2 YUKAWA study," Circulation Journal. 78(5):1073-1082.

Hochleitner et al., Characterization of a discontinuous epitope of the human immunodeficiency virus—HIV! core protein p24 by epitope excision and differential chemical modification followed by mass spectrometric peptide mapping analysis; Protein Science 2000, 9:487-496. Cambridge University Press.

Holliger et al., 'Diabodies: small bivalent and bispecific antibody fragments.' Proceedings of the National Academy of Sciences. 1993, vol. 90,No. 14, pp. 6444-6448.

Hopkins PN, Swergold GD, Mellis S, Bruckert E, Luc G, Mendoza J, Du Y, Krempf M. A randomized placebo-phase clinical trial with the monoclonal antibody alirocumab demonstrates reductions in low-density lipoprotein cholesterol in patients with proprotein convertase subtilisin/kexin type 9 gain-of-function mutations. Circulation. 2013;128:A17156.

Hopkins, et al., 2011 Journal of Clinical Lipidology 5(3):S9-S17, "Familial Hypercholesterolemias: Prevalence, genetics, diagnosis and screening recommendations from the National Lipid Association Expert Panel on Familial Hypercholesterolemia".

Horton, et al. (2007) Trends Biochem Sci. 32(2): 71-77, "Molecular biology of PCSK9: its role in LDL metabolism".

Hovingh GK, Davidson MH, Kastelein JJ, O'Connor AM. Diagnosis and treatment of familial hypercholesterolaemia. Eur Heart J 2013;34(13):962-971.

Huston et al. 'Protein engineering of antibody binding sites: recovery of specific activity in an anti-digoxin single-chain Fv analogue produced in *Escherichia coli.*' Proceedings of the National Academy of Sciences. 1988, vol. 85, No. 16, pp. 5879.

Igawa, et al. (2010) Nature Biotechnology 28(11):1203-1208, "Antibody recycling by engineered pH-dependent antigen binding improves the duration of antigen neutralization".

International Search Report and Written Opinion dated Apr. 16, 2015 for International Application No. PCT/US2014/060109 (19 pages).

International Search Report and Written Opinion dated Feb. 3, 2015 for International Application No. PCT/US2014/065149 (17 pages).

International Search Report and Written Opinion dated Jun. 12, 2015 for International Application No. PCT/US2015/020564 (20 pages).

International Search Report for International Application No. PCT/EP2012/051320, dated Sep. 21, 2012 (9 pages).

International Search Report with Written Opinion corresponding to International Patent Application No. PCT/EP2012/051321, dated Apr. 19, 2012, 10 pages.

International Search Report with Written Opinion corresponding to International Patent Application No. PCT/EP2012/057890, dated Aug. 28, 2012, 14 pages.

International Search Report with Written Opinion corresponding to International Patent Application No. PCT/US2015/040754, dated Oct. 14, 2015, 15 pages.

International Search Report with Written Opinion corresponding to International Patent Application No. PCT/US2015/040765, dated Nov. 26, 2015, 15 pages.

International Search Report and Written Opinion dated Aug. 19, 2015 for International application No. PCT/US2015/015633, 23 pages.

International Preliminary Report on Patentability dated Jul. 30, 2013 for International application No. PCT/EP12/051321, 7 pages.

Ito, et al. (1992) Federation of European Biochemical Societies 309(1):85-88, "The His-probe method: effects of histidine residues

(56) References Cited

OTHER PUBLICATIONS introduced into the complementarity-determining regions of antibodies on antigen-antibody interactions at different pH values".
Jones P, Bays H, Chaudhari U, Pordy R, Lorenzato C, Miller K, Robinson J. Pooled safety and adverse events in nine randomized, placebo-controlled, phase 2 and 3 clinical trials of alirocumab. J Am Coll Cardiol 2015;65(10_S):A1363.
Jorgensen et al. (2013) European Heart Journal 34:1826-1833, "Genetically elevated non-fasting triglycerides and calculated remnant cholesterol as casual risk factors for myocardial infarction".
Junghans et al.: Anti-Tac-H, a Humanized Antibody to the Interleukin 2 Receptor with New Features for Immunotherapy in Malignant and Immune Disorders; Cancer Research, 50. 1495-1502; Mar. 1. 1990.
Kastelein JJ, Robinson JG, Farnier M, Krempf M, Langslet G, Lorenzato C, Gipe DA, Baccara-Dinet MT. Efficacy and Safety of Alirocumab in Patients with Heterozygous Familial Hypercholesterolemia not Adequately Controlled with Current Lipid-Lowering Therapy: Design and Rationale of the ODYSSEY FH Studies. Cardiovasc Drugs Ther 2014; 28(3):281-289.
Kastelein JJP, Ginsberg HN, Langslet G, Kees Hovingh G, Ceska R, Dufour R, Blom D, Civeira F, Krempf M, Farnier M. Efficacy and safety of alirocumab in patients with heterozygous familial hypercholesterolaemia not adequately controlled with current lipid-lowering therapy: results of ODYSSEY FH I and FH II studies; presented at ESC Congress Aug. 31, 2014, abstract not published.
Katayama, et al. 2004 J. Pharm. Sci. 93(10): 2609-2623, "Retrospective statistical analysis of lyophilized Protein Formulations of Progenipoietin Using PLS: Determination of the Critical Parameters for Long-Term Storage Stability".
Kawashiri, et al. (2012) Circulation 126(21):13869, "Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope".
Kereiakes DJ, Robinson JG, Cannon CP, Lorenzato C, Pordy R, Chaudhari U, Colhoun HM. Efficacy and safety of alirocumab in high cardiovascular risk patients with suboptimally controlled hypercholesterolemia on maximally tolerated doses of statins: the ODYSSEY COMBO I study. Circulation. 2014;130:2119.
Kereiakes DJ, Robinson JG, Cannon CP, Lorenzato C, Pordy R, Chaudhari U, Colhoun HM. Efficacy and safety of the PCSK9 inhibitor alirocumab among high cardiovascular risk patients on maximally tolerated statin therapy: the ODYSSEY COMBO I study. Am Heart J. 2015. In press. DOI: http://dx.doi.org/10.1016/j.ahj.2015.03.004.
Koschinsky and Boffa (2014) Endocrinology and Metabolism Clinics of North America 43(4): 949-962, "Lipoprotein(a): An Important Cardiovascular Risk Factor and a Clinical Conundrum".
Koren M, Stein E, McKenney JM, Gipe D, Hanotin C, Ferrand A-C, Wu R, Dufour R. Efficacy, safety and tolerability of 150 mg Q2W dose of the anti-PCSK9 mAb, REGN727/SAR236553: data from 3 phase 2 studies. Eur Heart J 2012;33(Abstract Supplement);37. Abstract 429.
Koren MJ, Kereiakes D, Pourfarzib R, Winegar D, Banerjee P, Hamon S, Hanotin C, McKenney JM. Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial. J Am Coll Cardiol 2014;63(12 Suppl 1):A1373.
Koren MJ, Roth EM, McKenney JM, Gipe D, Hanotin C, Ferrand AC, Wu R, Dufour R. Safety and efficacy of alirocumab 150 mg every 2 weeks, a fully human proprotein convertase subtilisin/kexin type 9 monoclonal antibody: a Phase II pooled analysis. Postgrad Med 2015;22:1-8.
Koren MJ, Stein E, Roth E, McKenney JM, Gipe D, Hanotin C, Ferrand A-C, Wu R, Dufour R. Efficacy, safety and tolerability of alirocumab 150 mg Q2W, a fully human PCSK9 monoclonal antibody: a pooled analysis of 352 patients from phase 2. J Clin Lipidol 2013;7(3)279-280.
Kostner et al. (2013) European Heart Journal 34:3268-3276, "When should we measure lipoprotein (a)?".
Krauss RM, Banerjee P, Hamon S, Hanotin C, Sasiela B, Koren MJ, McKenney JM. Alirocumab, a fully human monoclonal antibody to proprotein convertase subtilisin/kexin type 9, and its effects on lipoprotein subfractions determined by ion mobility. Circulation. 2014;130:A15525.
Kühnast S, van der Hoorn JW, Pieterman E, Sasiela WJ, Gusarova V, Peyman A, Schäfer H-L, Schwahn U, Jukema JW, Princen HM. PCSK-9 monoclonal antibody alirocumab dose-dependently decreases atherosclerosis development and enhances the effects of atorvastatin in APOE*3Leiden.CETP mice. Circulation. 2013;128:A15823.
Kühnast S, van der Hoorn JWA, Pieterman EJ, van den Hoek AM, Sasiela WJ, Gusarova V, Peyman A, Schäfer H-L, Schwahn U, Jukema JW, Princen HMG. Alirocumab inhibits atherosclerosis, improves the plaque morphology, and enhances the effects of a statin. J Lipid Res. 2014;55(10):2103-2112.
Lagace, et al. (2006) J Clin Invest Am Soc Clin Invest 116(11):2995-3005, "Secreted PCSK9 decreases the number of LDL receptors in hepatocytes and in liver of parabiotic mice".
Lambert G, Chatelais M, Petrides F, Passard M, Thedrez A, Rye KA, Schwahn U, Gusarova V, Blom DJ, Sasiela W, Marais AD. Normalization of Low-Density Lipoprotein Receptor Expression in Receptor Defective Homozygous Familial Hypercholesterolemia by Inhibition of PCSK9 With Alirocumab. J Am Coll Cardiol. 2014;64(21):2299-2300.
Lambert G, Sjouke B, Choque B, Kastelein JJ, Hovingh GK. The PCSK9 decade. J Lipid Res 2012;53(12):2515-2524.
Lamon-Fava, et al. (2011) Journal of Lipid Research 52:1181-1187 "Lipoprotein(a) levels, apo(a) isoform size, and coronary heart disease risk in the Framingham Offspring Study".
Langer et al., 'Medical Applications of Controlled Release.' CRC Press, Boca Raton, Florida. 1974, pp. 115-138.
Langer et al., 'New methods of drug delivery.' Science. 1990, vol. 249, No. 4976, pp. 1527-1533.
Lefranc, M.-P., et al., IMGT®, the international ImMunoGeneTics information system®, Nucl. Acids Res, 37, D1006-D1012 (2009).
Leuenberger et al., 'A Multilingual Glossary of Biotechnological Terms.' Recueil des Travaux Chimiques des Pays Bas. 1996, vol. 115, No. 7, pp. 382.
Lippi and Guidi (2000) QJ Med 93:75-84, "Lipoprotein(a): from ancestral benefit to modern pathogen?".
Lopez, Dayami (2008) Drug News & Perspectives Abstract 21(6): 323, "Inhibition of PCSK9 as a Novel Strategy for the Treatment of Hypercholesterolemia".
Lose, et al., 2013 Pharmacotherapy: The Journal of Human Pharmacology and Drug Therapy 33(4):447-460, "Evaluation of Proprotein Convertase Subtilisin/Kexin Type 9: Focus on Potential Clinical and Therapeutic Implications for Low-Density Lipoprotein Cholesterol Lowering".
Lunven C, Paehler T, Lewanczyk P, Poitiers F, Brunet A, Rey J, Hanotin C, Sasiela WJ. A randomized study of the relative bioavailability, pharmacodynamics, and safety of alirocumab, a fully human monoclonal antibody to proprotein convertase subtilisin/ kexin type 9, after single subcutaneous administration at three different injection sites in healthy subjects. J Am Coll Cardiol 2014;63(12 Suppl 1): A1377.
Lunven C, Paehler T, Poitiers F, Brunet A, Rey J, Hanotin C, Sasiela WJ. A randomized study of the relative pharmacokinetics, pharmacodynamics and safety of alirocumab, a fully human monoclonal antibody to PCSK9, after single subcutaneous administration at three different injection sites in healthy subjects. Cardiovasc Ther. Dec. 2014.;32(6):297-301.
Maeda, et a. (2002) J. Controlled Release 82:71-82, "pH-dependent receptor/ligand dissociation as a determining factor for intracellular sorting of ligands for epidermal growth factor receptors in rat hepatocytes".
Marcovina and Koschinsky (1998) The American Journal of Cardiology 82(12A):57U-66U, "Lipoprotein(a) as a Risk Factor for Coronary Artery Disease".
Majumdar, et al. (2011) Journal of Pharmaceutical Sciences 100(7):2563-2573, "Evaluation of the effect of syringe surfaces on protein formulations".

(56) References Cited

OTHER PUBLICATIONS

Maxwell and Breslow (2004) PNAS 101(18):7100-7105, "Adenoviral-mediated expression of Pcsk9 in mice results in a low-density lipoprotein receptor knockout phenotype".
McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Presented as a poster presentation at the 81st European Atherosclerosis Society (EAS) Congress, Jun. 2-5, 2013, Lyon, France.
McKenney J, Koren M, Kereiakes D, Hanotin C, Ferrand A-C. A randomized, double-blind, placebo-controlled trial of the safety and efficacy of a monoclonal antibody to proprotein convertase subtilisin/kexin type 9 serine protease, REGN727/SAR236553, in patients with primary hypercholesterolemia (NCT: 01288443). Presented as a late-breaking oral presentation at the American College of Cardiology (ACC) Annual Scientific Session, Mar. 24-27, 2012, Chicago, Illinois, USA.
McKenney, et a. (2012) Journal of the American College of Cardiology 59(25):2335-2353, "Safety and Efficacy of a Monoclonal Antibody to Proprotein Convertase Subtilisin/Kexin Type 9 Serine Protease, SAR236553/REGN727, in Patients With Primary Hypercholesterolemia Receiving Ongoing Stable Atorvastatin Therapy".
Meehan et al., 1996, J. Controlled Release 46:107-116, "A microinfusor device for the delivery of therapeutic levels of peptides and macromolecules".
Missouri Du Report, Drug Use Review Newsletter, vol. 8, No. 6, Oct./Nov. 2003 "Statin Therapy" pp. 1-9.
Moriarty PM, Jacobson TA, Bruckert E, Thompson PD, Guyton JR, Baccara-Dinet MT, Gipe D. Efficacy and safety of alirocumab, a monoclonal antibody to PCSK9, in statin-intolerant patients: Design and rationale of ODYSSEY Alternative, a randomized Phase 3 trial. J Clin Lipidol. 2014;8(6):554-561.
Moriarty PM, Lecorps G, Hanotin C, Pordy R, Roth EM. Homogeneity of treatment effect of REGN727/SAR236553, a fully human monoclonal antibody against PCSK9, in lowering LDL-C: data from three phase 2 studies. Eur Heart J. 2013;34(Suppl 1):doi:10.1093/eurheartj/eht307.142.
Moriarty PM, Thompson PD, Cannon CP, Guyton JR, Bergeron J, Zieve FJ, Bruckert E, Jacobson TA, BaccaraDinet MT, Zhao J, Pordy R, Gipe R. Odyssey Alternative: Efficacy and safety of the proprotein convertase subtilisin/kexin type 9 monoclonal antibody, alirocumab, versus ezetimibe, in patients with statin intolerance as defined by a placebo run-in and statin rechallenge arm. Circulation. 2014;130:2108.
Nakasako, et a. (1999) J. Mol. Biol. 291:117-134, "The pH-dependent structural variation of complementarity-determining region H3 in the crystal structures of the Fv fragment from an anti-dansyl monoclonal antibody".
Naureckiene, et al. (2003) Archives of Biochemistry and Biophysics 420:55-67, "Functional characterization of Narc 1, a novel proteinase related to proteinase K".
Noguchi, et al., 2010 Atherosclerosis 210(1):166-172, "The E32K variant of PCSK9 exacerbates the phenotype of familial hypercholesterolemia by increasing PCSK9 function and concentration in the circulation".
Nordestgaard, et al. (2010) European Heart Journal 31:2844-2853, "Lipoprotein(s) as cardiovascular risk factor: current status".
Padlan et al., 'Identification of specificity-determining residues in antibodies.' The FASEB Journal. 1995, vol. 9, No. 1, pp. 133-139.
Parhofer (2011) Current Pharmaceutical Design 17:871-876, "Lipoprotein(a): Medical Treatment Options for an Elusive Molecule".
Park, et al. (2004) J. Biol. Chem. 279: 50630-50638, "Lipids and Lipoproteins: Post-transcriptional Regulation of Low Density Lipoprotein Receptor Protein by Proprotein Convertase Subtilisin/Kexin Type 9a in Mouse Liver".
Partial International Search Report dated Nov. 6, 2014 for International Application No. PCT/US2014/040163.

Pearson, William R., 'Using the FASTA program to search protein and DNA sequence databases.' Computer Analysis of Sequence Data. 1994, pp. 307-331.
Pfizer: 'Safety and Tolerability of Multiple Doses of PF-04950615 (RN316) in Subjects With Hypercholesterolemia.' Nov. 3, 2012, XP002682100. Retrieved from the Internet: URL:http://clinicaltrials.gov/ct2/show?term=rn316&rank=2.
Pordy R, Lecorps G, Bessac L, Sasiela WJ, Ginsberg H. Alirocumab, a fully human monoclonal antibody to proprotein convertase subtilisin/kexin type 9: therapeutic dosing in phase 3 studies. J Clin Lipidol 2013;7(3):279.
Powell et al., 'Compendium of Excipients for Parenteral Formulations PDA.' Journal of Pharmaceutical Science and Technology. 1998, vol. 52, No. 5, pp. 238-311.
Qiu et al., 'Small antibody mimetics comprising two complementarity-determining regions and a framework region for tumor targeting.' Nature Biotechnology. 2007, vol. 25, No. 8, pp. 921-929.
Rader, et al. (1995) The Journal of Clinical Investigation, Inc. 95:1403-1408, "The Low Density Lipoprotein Receptor is Not Required for Normal Catabolism of Lp(a) in Humans".
Ramanathan A, Gusarova V, Kyratsous C. Role of alirocumab (proprotein convertase subtilisin/kexin type 9 antibody) on CD81 levels and hepatitis C virus entry into hepatocytes. Circulation. 2013;128:A12052.
Rashid, et al. (2005) PNAS 102(15):5374-5379, "Decreased plasma cholesterol and hypersensitivity to statins in mice lacking Pcsk9".
Ray KK, Foody J, Khan I, Lewis BE. Attainment of low-density lipoprotein cholesterol goals in patients at very high cardiovascular risk in the United Kingdom: results from a general practice population study. Value Health 2013;16(7):A513.
Reddy et al., 'Elimination of Fc receptor-dependent effector functions of a modified IgG4 monoclonal antibody to human CD4.' The Journal of Immunology. 2000, vol. 164, No. 4, pp. 1925-1933.
Regeneron/Sanofi (2012) IR Conference Call on PCSK9 "SAR236553/REGN727 PCSK9 Antibody for Hypercholesterolemia Phase 3 ODYSSEY Program Underway".
Reineke, Ulrich, 'Antibody epitope mapping using arrays of synthetic peptides.' Antibody Engineering. Humana Press. 2004, pp. 443-463.
Rey J, Poitiers F, Paehler T, Brunet A, Pinquier JL, Hanotin C, Sasiela B. Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects. J Am Coll Cardiol 2014;63(12 Suppl 1):A1375.
Rhainds, et al., 2012 Clinical Lipidology 7(6):621-640, "PCSK9 inhibition and LDL cholesterol lowering: The biology of an attractive therapeutic target and critical review of the latest clinical trials".
Robinson, N., 2002, *PNAS*, 99(8):5283-5288 "Protein Deamidation".
Robinson J, Farnier M, Chaudhari U, Sasiela B, Lorenzato C, Miller K, Kastelein JJP. Adverse events in patients with low-density lipoprotein cholesterol levels <25 or <15 mg/dL on at least two consecutive visits in fourteen randomized, controlled, clinical trials of alirocumab. J Am Coll Cardiol 2015;65(10_S):A1350.
Robinson JG, Colhoun HM, Bays HE, Jones PH, Du Y, Hanotin C, Donahue S, Efficacy and safety of alirocumab as add-on therapy in high-cardiovascular-risk patients with hypercholesterolemia not adequately controlled with atorvastatin (20 or 40 mg) or rosuvastatin (10 or 20mg): design and rationale of the ODYSSEY Options studies. Clin Cardiol. 2014;37(10):597-604.
Robinson JG, Farnier M, Krempf M, Bergeron J, Luc G, Averna M, Stroes E, Langslet G, Raal FJ, El Shahawy M, Koren MJ, Lepor N, Lorenzato C, Pordy R, Chaudhari U, Kastelein JJP. Long-term safety, tolerability and efficacy of alirocumab versus placebo in high cardiovascular risk patients: first results from the ODYSSEY Long Term study in 2,341 patients; presented at ESC Congress Aug. 31, 2014, abstract not published.
Robinson JG, Farnier M, Krempf M, Bergeron J, Luc G, Averna M, Stroes E, Langslet G, Raal FJ, El Shahawy M, Koren MJ, Lepor N, Lorenzato C, Pordy R, Chaudhari U, Kastelein JJP. Long-term safety, tolerability and efficacy of alirocumab versus placebo in high

(56) References Cited

OTHER PUBLICATIONS cardiovascular risk patients: first results from the ODYSSEY Long Term study in 2,341 patients. Circulation. 2014;130:2120.
Robinson JG, Farnier M, Krempf M, Bergeron J, Luc G, Averna M, Stroes ES, Langslet G, Raal FJ, Shahawy ME, Koren MJ, Lepor NE, Lorenzato C, Pordy R, Chaudhari U, Kastelein JJ; ODYSSEY Long Term Investigators. Efficacy and Safety of Alirocumab in Reducing Lipids and Cardiovascular Events. N Eng J Med. 2015.
Romagnuolo, et al. (2015) The Journal of Biological Chemistry 290(18):11649-11662, "Lipoprotein(a) Catabolism is Regulated by Proprotein Convertase Subtilisin/Kexin Type 9 through the Low Density Lipoprotein Receptor".
Roth E, Taskinen M-R, Ginsberg HN, Kastelein JJP, Colhoun HM, Robinson JG, Merlet L, Pordy R, Baccara-Dinet MT. A 24-week study of alirocumab monotherapy versus ezetimibe: The first phase 3 data of a proprotein convertase subtilisin/kexin type 9 inhibitor. J Am Coll Cardiol 2014;63(12 Suppl 1): A.
Roth EM, McKenney J, Hanotin C, Asset G, Stein E. The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469). J Am Coll Cardiol 2012;59:E1620.
Roth EM, McKenney JM, Hanotin C, Asset G, Stein EA. Atorvastatin with or without an antibody to PCSK9 in primary hypercholesterolemia. N Engl J Med. 2012;367(20):1891-1900.
Roth EM, McKenney JM. ODYSSEY Mono: effect of alirocumab 75 mg subcutaneously every 2 weeks as monotherapy versus ezetimibe over 24 weeks. Future Cardiol 2015;11(1):27-37.
Roth EM, Taskinen M-R, Ginsberg H, Kastelein JJP, Colhoun HM, Robinson JG, Merlet L, Pordy R, Baccara-Dinet MT. Monotherapy with the PCSK9 inhibitor alirocumab versus ezetimibe in patients with hypercholesterolemia: Results of a 24 week, double-blind, randomized Phase 3 trial. Int J Cardiol. 2014;176(1):55-61.
Roth et al. Alirocumab for hyperlipidemia: physiology of PCSK9 inhibition, pharmacodynamics and Phase I and II clinical trial results of a PCSK9 monoclonal antibody. Future Cardiology. Mar. 2014; vol. 10, No. 2. pp. 183-199.
Sarkar, et al. (2002) Nature Biotechnology 20:908-913, "Rational cytokine design for increased lifetime and enhanced potency using pH-activated histidine switching".
Scaviner, D. et al., 1999 Exp. Clin. Immunogenet. 16:234-240 "Protein Displays of the Human Immunoglobulin Heavy, Kappa and Lambda Variable and Joining Regions".
Schäfer et al. (Mar. 14-16, 2011) "Cholesterol lowering effect of SAR236553/REGN727, a fully human PCSK9 blocking monoclonal antibody in male Syrian hamster," Presented as a poster at the Drugs Affecting Lipid Metabolism (DALM)—XVII International Symposium, Mar. 14-16, 2011, Doha, Qatar.
Schwartz GG, Bessac L, Berdan LG, Bhatt DL, Bittner V, Diaz R, Goodman SG, Hanotin C, Harrington RA, Jukema JW, Mahaffey KW, Moryusef A, Pordy R, Roe MT, Rorick T, Sasiela WJ, Shirodaria C, Szarek M, Tamby J-F, Tricoci P, White H, Zeiher A, Steg PG. Effect of alirocumab, a monoclonal antibody to pcsk9, on long-term cardiovascular outcomes following acute coronary syndromes: Rationale and design of the odyssey outcomes trial. Am Heart J. 2014;168(5):682-689.e1.
Sefton, Michael V., 'Implantable Pumps.' Critical Reviews in Biomedical Engineering. 1986, vol. 14, No. 3, pp. 201-240.
Seidah et al., 'The secretory proprotein convertase neural apoptosis-regulated convertase 1 (NARC-1): liver regeneration and neuronal differentiation.' PNAS. 2003,100(3):928-933.
Shao W. New Therapies for Lowering LDL-C: Targeting PCSK9. Abstract of oral presentation at the Sino-American Pharmaceutical Professionals Association—2014 Scientific Symposium, Apr. 26, 2014, New Jersey, USA.
Shields et al., 'Lack of fucose on human IgG1 N-linked oligosaccharide improves binding to human FcγRIII and antibody-dependent cellular toxicity.' Journal of Biological Chemistry. 2002, vol. 277, No. 30, pp. 26733-26740.
Soutar, Anne, 'Unexpected Roles for PCSK9 in Lipid Metabolism.' Current Opinion in Lipidology. 2011, vol. 22, pp. 192-196.
Steen D, Khan I, Becker L, Gorcyca K, Foody J. Attainment of Lipid Levels in Patients at High Cardiovascular Risk: Results from a U.S. Managed Care Population Study. Circulation. 2014;130:A19949.
Steen D, Khan I, Song X, Sanchez R, Gorcyca K, Hollenbeak CS, Foody J. Cardiovascular Event Rates in a High-Risk Managed Care Population in the United States. J Am Coll Cardiol 2015;65(10_S):A1647.
Stein and Swergold, 2013 Current Atherosclerosis Reports 15(310):1-14, "Potential of proprotein Convertase Subtilisin/Kexin Type 9 Based Therapeutics".
Stein EA, Bergeron J, Gaudet D, Weiss R, Dufour R, Du Y, Yang F, Andisik M, Torri A, Pordy R, Gipe D. One year open-label treatment with alirocumab 150 mg every two weeks in heterozygous familial hypercholesterolemic patients. J Am Coll Cardiol 2014;63(12 Suppl 1): A1371.
Stein E, Bergeron J, Gaudet D, Weiss R, Gipe D, Wu R, Dufour R, Pordy R. Safety and efficacy of a monoclonal antibody to PCSK9, REGN727/SAR236553, in statin-treated heterozygous familial hypercholesterolemia patients. Presented as an oral presentation at the 80th European Atherosclerosis Society (EAS) Congress, May 25-28, 2012, Milan, Italy. Abstract 1398.
Stein, et al. (2012) New England Journal of Medicine 366:1108-1118, "Effect of a Monoclonal Antibody to PCSK9 on D Cholesterol".
Stein, et al. (2012) The Lancet 380:29-36, "Effect of a monoclonal antibody to PCSK9, REGN727/SAR236553, to reduce low-density lipoprotein cholesterol in patients with heterozygofamilial hypercholesterolemia on stable statin dose with or without ezetimibe therapy: a phase 2 randomized controlled trial".
Stein, et al., 2012 Obstetrical and Gynecological Survey 67(7):413-414, "Effect of a monoclonal antibody to PCSK9 on LDL cholesterol".
Stroes E, Guyton JR, Farnier M, Rader D, Moriarty PM, Bergeron J, Langslet G, Lepor N, Civeira F, Gaudet D, Watts GF, Manvelian G, Lecorps G, Zhao J, Baccara-Dinet M, Roth EM. Efficacy and safety of different dosing regimens of alirocumab (starting doses of 75 mg every two weeks and 150 mg every four weeks) versus placebo in patients with hypercholesterolemia not treated using statins: the ODYSSEY Choice II study. J Am Coll Cardiol 2015;65(10_S):A1370.
Sullivan, et al. Effect of a Monoclonal Antibody to PCSK9 on Low-Density Lipoprotein Cholesterol Levels in Statin-Intolerant Patients. JAMA. Dec. 19, 2012. vol. 308, No. 23. pp. 2497-2506.
Swergold G, Biedermann S, Renard R, Du Y, Nadler D, Wu R, Mellis S, Lisbon E. REGN727/SAR236553, a fully-human monoclonal antibody to proprotein convertase subtilisin kexin 9 (PCSK9), decreases ApoB and non-HDL-C when administered intravenously to healthy volunteers. J Clin Lipidol 2011;5(3):219.
Swergold G, Biedermann S, Renard R, Nadler D, Wu R, Lisbon EA, Gutierrez MJ, Mellis S. REGN727/SAR236553, a fully human proprotein convertase subtilisin kexin 9 (PCSK9) monoclonal antibody: effects on safety and lipid and lipoprotein profiles when administered subcutaneously. J Am Coll Cardiol 2011;57(14s1):E2023.
Swergold G, Biedermann S, Renard R, Nadler D, Wu R, Mellis S. Safety, lipid, and lipoprotein effects of REGN727/SAR236553, a fully human proprotein convertase subtilisin kexin 9 (PCSK9) neutralizing monoclonal antibody administered intravenously to healthy volunteers. Circulation 2010;122:Abstract A23251.
Swergold G, Smith W, Mellis S, Logan D, Webb C, Wu R, Du Y, Krans T, Gasparino E, Stein EA. Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia. Circulation 2011;124:Abstract A16265.
Swergold GD, et al. Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB). Abstract of a

(56) References Cited

OTHER PUBLICATIONS poster presentation at the American Society of Human Genetics (ASHG), Oct. 22-26, 2013, Boston, USA.
Tavori, Hagai et al. (2013) Circulation Research: 1290-1302 "Loss of Plasma Proprotein Convertase Subtilisin/Kevin 9 (PCSK9) After Lipoprotein Apheresis".
Teramoto T, Kobayashi M, Uno K, Takagi Y, Matsuoka O, Sugimoto M, Inoue S, Minami F, Baccara-Dinet MT. Efficacy and safety of alirocumab in Japanese patients with hypercholesterolemia on stable statin therapy: first data with the 75 mg every two weeks dose. Circulation. 2014;130:A13651.
Third Party Observation for European Patent Application No. 12761864.3 dated Feb. 24, 2016.
Thompson J. et al., (2006) Atherosclerosis 189:31-38 "A systematic review of LDL apheresis in the treatment of cardiovascular disease".
Timms, et al. (2004) Human Genetics 114(4):349-353, "A mutation in PCSK9 causing autosomal-dominant hypercholesterolemia in a Utah pedigree".
Tiwari et al., 'Statins therapy: a review on conventional and novel formulation approaches.' Journal of Pharmacy and Pharmacology. 2011, vol. 63, No. 8, pp. 983-998.
Toth PP, Hamon S, Jones SR, Joshi PH, Martin SS, Pordy R, Hanotin C. Alirocumab, a proprotein convertase subtilisin/kexin type 9 monoclonal antibody, reduces cholesterol concentrations of all serum low-density lipoprotein cholesterol fractions. Circulation. 2013;128:A17313.
Toth PP, Hamon S, Jones SR, Martin SS, Joshi PH, Kulkarni K, Banerjee P, Hanotin C. Proprotein convertase subtilisin/kexin 9 monoclonal antibody therapy significantly reduces apoprotein CII and CIII levels in serum. Atherosclerosis. 2014;235(2):e107-e108. [Abstract 593].
Toth, et al., (2013) Circulation 128(22):17492, "Alirocumab, a Proprotein Convertase Subtilisin/Kexin Type 9 Monoclonal Antibody, Reduces Cholesterol Concentrations of Serum Remnant Lipoprotein Fractions, Very Low-Density Lipoproteins and Triglycerides".
Tsimikas, et al. (2015) The Lancet 386(10002):1472-1483, "Antisense therapy targeting apolipoprotein(a): a randomised, double-blind, placebo-controlled phase 1 study".
Tutt et al., 'Trispecific F (ab') 3 derivatives that use cooperative signaling via the TCR/CD3 complex and CD2 to activate and redirect resting cytotoxic T cells.' The Journal of Immunology. 1991, vol. 147, No. 1, pp. 60-69.
Vajdos et al., 'Comprehensive functional maps of the antigen-binding site of an anti-ErbB2 antibody obtained with shotgun scanning mutagenesis.' Journal of Molecular Biology. 2002, vol. 320, No. 2, pp. 415-428.
Van der Hoorn JWA, Kuhnast S, Pieterman E, van der Hoek AM, Sasiela WJ, Gusarova V, Peyman A, Schafer H-L, Schwahn U, Jukema JW, Princen HMG. Alirocumab, a monoclonal antibody to PCSK-9, dose-dependently decreases atherosclerosis, improves plaque stability and shows additive effects with atorvastatin in APOE*3Leiden. CETP mice. Atherosclerosis. 2014;235(2):e19. [Abstract WS16].
Varbo, et al., (2013) Journal of the American College of Cardiology 61(4):427-436, "Remnant Cholesterol as a Casual Risk Factor for Ischemic Heart Disease".
Varret, et al., 1999 Am. J. Hum. Genet. 64: 1378-1387, "A third major locus for autosomal dominant hypercholesterolemia Maps to 1p34.1-p32".
Wang, 1999 International J. Pharmaceutics 185(2): 129-188, "Instability, stabilization, and formulation of liquid protein pharmaceuticals".
Walji S., (2013) Clinical Lipidology 8(5):573-586, "Lipoprotein Apheresis for the Treatment of Familial Hypercholesterolemia".
Ward et al., 'Binding activities of a repertoire of single immunoglobulin variable domains secreted from*Escherichia coli*.' Nature. 1989, vol. 341, No. 6242, pp. 544-546.
Watanabe, et al. (2009) J. Biological Chemistry 284(18):12373-12383, "Optimizing pH response of affinity between protein G and IgG Fc".

Webb, et al. 2002 J. Pharm. Sci. 91(2): 543-558, "A new mechanism for decreasing aggregation of Recombinant Human Interferon-γ by a Surfactant: Slowed Dissolution of Lyophilized Formulations in a Solution Containing 0.03% Polysorbate 20".
Winter and Harris (1993) Immunology Today 14(6):243-246, "Humanized Antibodies".
Wong ND, Chuang J. Residual Dyslipidemia According to LDL-C, non-HDl-C and Apolipoprotein B by Cardiovascular Risk Category in Statin Treated US Adults. J Clin Lipidol. 2014;8:323-324. Presented as a poster presentation at the National Lipid Association Scientific Sessions, May 1-4, 2014, Orlando, Florida, USA.
Written Opinion of the International Searching Authority for International Application No. PCT/EP2012/051320, dated Jul. 30, 2013 (16 pages).
Wu et al., 'Receptor-mediated in vitro gene transformation by a soluble DNA carrier system.' Journal of Biological Chemistry. 1987, vol. 262, No. 10, pp. 4429-4432.
Brouwers, M. C. G. J., et al., "Plasma proprotein convertase subtilisin kexin type 9 levels are related to markers of cholesterol synthesis in familial combined hyperlipidemia," Nutrition, Metabolism & Cardiovascular Diseases (2013) 23, 1115-1121.
Yamashita, Sizuya, "PCSK9 (proprotein convertase subtilisin/kexin type 9)", Prevention of Arteriosclerosis, Feb. 10, 2013, vol. 11, No. 4, p. 101-105 (Lambert, Gilles, et al., "Molecular basis of PCSK9 function," Atherosclerosis 203 (2009) 1-7).
Ned, R.M., et al., Cascade Screening for Familial Hypercholesterolemia (FH), PLOS Currents Evidence on Genomic Tests, Jul. 1, 2011. Edition 1. doi: 10.1371/currents.RRN1238.
Todo, Yasuhiro, et al., "Detailed Analysis of Serum Lipids and Lipoproteins from Japanese Type III Hlyperlipoproteinemia with Apolipoprotein E2/2 Phenotype," Clinica Chimica Acta 348 (2004) 35-40.
Ason, Brandon, et al., "Improved efficacy for ezetimibe and rosuvastatin by attenuating the induction of PCSK9," Journal of Lipid Research, vol. 52, 2011, pp. 679-687.
Chaudhary, Rahul, et al., "PCSK9 inhibitors: A new era of lipid lowering therapy," World Journal of Cardiology, Feb. 26, 2017; 9(2): 76-91.
Zimmerman, Marj P., "How Do PCSK9 Inhibitors Stack Up to Statins for Low-Density Lipoprotein Cholesterol Control?", American health & Drug Benefits, Nov. 1, 2015, p. 436.
Stone, Neil J., et al., "2013 ACC/AHA Guideline on the Treatment of Blood Cholesterol to Reduce Atherosclerotic Cardiovascular Risk in Adults," A report of the American College of Cardiology/American Heart Association Task Force on Practice Guidelines, Journal of the American College of cardiology, vol. 63, No. 25, Nov. 12, 2013 (Nov. 12, 2013), pp. 2889-2934.
Rahilly-Tierney, Catherine R., "Low-Density Lipoprotein Reduction and Magnitude of Cardiovascular Risk Reduction," Clinical Study, Preventive Cardiology, Spring 2009, Maveric, pp. 80-87.
Notice of Reason(s) for Rejection for JP 2016-516825, dated Jan. 16, 2018.
McNutt, Markey C., et al., "So Far, PCSK9 Inhibitors Work for All Heterozygous FH Patients," Circ Cardiovasc Genet.2015;8:749-751.
"Sanofi and Regeneron Announce Collaboration with American College of Cardiology for PCSK9 Inhibitor Clinical Program", Dec. 19, 2013, PRNewswire, obtained on Dec. 5, 2018 at: https://newsroom.regeneron.com/news-releases/news-release-details/sanofi-and-regeneron-announce-collaboration-american-college . . . , 5 pages.
"Sanofi and Regeneron Report Positive Top-line Results with Alirocumab from First Phase 3 Study of a PCSK9 Inhibitor for LDL Cholesterol Reduction", Oct. 16, 2013, ePressPack, Jay Edelberg M.D., Ph.D, obtained online on Dec. 5, 2018 at: http://www.epresspack.net/mmr/sanofi-pcsk9-1st-phase3-results/, 3 pages.
Ason (2011) Journal of Lipid Research 52:679-687 "Improved Efficacy for Ezetimibe and Rosuvastatin by Attenuating the Induction of PCSK9".
Chaudhary et al. (2017) World J. Cardiol. 9(2):76-91 "PCSK9 Inhibitors: A New Era of Lipid Lowering Therapy".

(56) References Cited

OTHER PUBLICATIONS

Fasano (2009) Atherosclerosis 203:166-171 "Degradation of LDLR Protein Mediated by Gain of Function PCSK9 Mutants in Normal and ARH Cells".
Stone et al. (2014) JACC 63(25):2889-2934 "2013 ACC/AHA Guideline on the Treatment of Blood Cholesterol to Reduce Atherosclerotic Cardiovascular Risk in Adults".
Zimmerman (2015) Am Health Drug Benefits 8(8):436-442 "How do PCSK9 Inhibitors Stack Up to Statins for Low-Density Lipoprotein Cholesterol Control".
Lalanne, Florent, et al., "Wild-type PCSK9 inhibits LDL clearance but does not affect apoB-containing lipoprotein production in mouse and cultured cells," Journal of Lipid Research, vol. 46, 2005, pp. 1312-1319.
Voet, et al., "Fundamentals of Biochemistry," Von Hoffmann Press, Inc., 1999, pp. 260-264.
Bendig, Mary M., "Humanization of Rodent Monoclonal Antibodies by CDR Grafting," Methods: A Companion to Methods in Enzymology 8, 83-93 (1995).
Jefferis, Roy, et al., "Human Immunoglobulin Allotypes," Review mAbs 1:4, 1-7; Jul./Aug. 2009.
QSM, "Essential medicines and health products," WHO Drug Information, vol. 26, No. 2, 2012.
Voet, et al., "Fundamentals of Biochemistry," Von Hoffmann Press, Inc., 1999, pp. 80-81.
Defesche et al. (Jun. 2-5, 2013) Presentation presented at the 81st European Atherosclerosis Society (EAS) Congress, Lyon, France "Natural history of autosomal dominant hypercholesterolemia caused by gain-of-function mutations in proprotein convertase subtilisin/kexin type 9 (PCSK9) (funded by Regeneron/Sanofi)".
McKenney et al. (2013) Abstract 81st European Atherosclerosis Society (EAS) Congress, Jun. 2-5, 2013, Lyon, France "Dynamics between the monoclonal antibody SAR236553/REGN727, proprotein convertase subtilisin/kexin type 9 and low-density lipoprotein cholesterol (LDL-C) levels (funding: Regeneron/Sanofi)".
Goodson (1984) Medical Applications of Controlled Release 2:115-138 "Chapter 6:Dental Applications".
Reyes-Soffer et al. (2017) Circulation 135:352-362 "Effects of PCSK9 Inhibition with Alirocumab on Lipoprotein Metabolism in Healthy Humans".
Bays et al. (2015) J Clin Lipidol. 9(3):471-472 Abstract 183 "Alirocumab treatment effect on non-HDL-C: pooled analyses of ten Phase 3 trials in the ODYSSEY program".
Berthold and Berthold (2013) Atherosclerosis Supplements 14:10-5 "Hyperlipoproteinemia(a): Clinical significance and treatment options".
Cariou et al. (May 23-26, 2015) International Symposium on Atherosclerosis. Abstract No. 1039 "Patient arid physician perspectives on administration of the PCSK9 monoclonal antibody alirocumab, an injectable medication to lower LDL-C levels".
clinicaltrials.gov (Dec. 23, 2010) "View of NCT01266876," US National Institutes of Health. [accessible on the internet at: https://clinicaltrials.gov/archive/NCT01266876/2010_12_23].
clinicaltrials.gov (Feb. 1, 2011) "View of NCT01288443," US National Institutes of Health. [accessible on the internet at: https://clinicaltrials.gov/archive/NCT01288443/2011_02_01).
clinicaltrials.gov (First Received: Aug. 8, 2012) "View of NCT01663402," US National Institutes of Health. [accessible on the internet at: https://clinicaltrials.gov/ct2/show/NCT01663402].
clinicaltrials.gov (First Received: Jun. 8, 2012) "View of NCT01617655," US National Institutes of Health. [accessible on the internet at: https://clinicaltrials.gov/ct2/show/NCT01617655?term=NCT01617655&rank=1].
clinicaltrials.gov (First Received: Jan. 6, 2012) "View of NCT01507831," US National Institutes of Health. [accessible on the internet at: https://clinicaltrials.gov/ct2/show/NCT01507831?term=NCT01507831&rank=1].
clinicaltrials.gov (First Received: Feb. 1, 2011) "View of NCT01288469," US National Institutes of Health. [accessible on the internet at: https://clinicaltrials.gov/ct2/show/NCT01288469?term=NCT01288469&rank=1].
clinicaltrials.gov (First Received: Oct. 8, 2012) "View of NCT01709500," US National Institutes of Health. [accessible on the internet at: https://clinicaltrials.gov/ct2/show/NCT01709500?term=NCT01709500&rank=1].
clinicaltrials.gov (First Received: Jul. 16, 2012) "View of NCT01644175," US National Institutes of Health. [accessible on the internet at: https://clinicaltrials.gov/ct2/show/NCT01644175?term=NCT01644175&rank=1].
clinicaltrials.gov (First Received: Jul. 16, 2012) "View of NCT01644188," US National Institutes of Health. [accessible on the internet at: https://clinicaltrials.gov/ct2/show/NCT01644188?term=NCT01644188&rank=1].
clinicaltrials.gov(First Received: Jul. 9, 2010) "View of NCT01161082," US National Institutes of Health. [accessible on the internet at: https://clinicaltrials.gov/ct2/show/NCT01161082?term=NCT01161082&rank=1].
clinicaltrials.Gov (First Received: Jul. 17, 2012) "View of NCT01644474," US National Institutes of Health. [accessible on the internet at: https://clinicaltrials.gov/ct2/show/NCT01644474?term=NCT01644474&rank=1].
Dufour et al. (2014) Can J Cardiol 30(10 suppl):S338 Abstract 546 "One year open-label treatment with alirocumab 150 mg every two weeks in heterozygous familial hypercholesterolemic patients".
Gaudet et al. (2012) Circulation 126:Abstract A14725 "Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443)".
Gaudet et al. (2017) Am Journal Cardiology 119:40-46 "Effect of Alirocumab on Lipoprotein(a) Over ‡1.5 Years (from the Phase 3 ODYSSEY Program)".
Gorcyca et al. (2015) J Clin Lipidol. 9(3):424 Abstract 118 "Prevalence of atherosclerotic cardiovascular disease and diabetes in the United States".
Hopkins et al. (Dec. 2015) Circ Cardiovasc Genet. 8(6):823-831 "Characterization of Autosomal Dominant Hypercholesterolemia Caused by PCSK9 Gain of Function Mutations and its Specific Treatment with Alirocumab, a PCSK9 Monoclonal Antibody".
Huang et al. (May 2015) J Clin Lipidol. 9(3):437-438 Abstract 134 "Clinical characteristics and unmet need among real-world atherosclerotic cardiovascular disease (ASCVD) patients stratified by statin use".
ISR and WO for International Application No. PCT/US2014/046170 dated Oct. 2, 2014.
ISR and WO from PCT/US2014/040050 dated Oct. 6, 2014.
ISR with WO for International Patent Application No. PCT/EP2015/055369 dated May 21, 2015.
ISR with WO for International Patent Application No. PCT/US2014/041204 dated Oct. 17, 2014.
Kolata (2015) The New York Times "Praluent Looks Cheap to Those with Extreme Cholesterol" Website [Online] Available Website: www.nytimes.com/2015/07/28/health/praluent-looks-cheap-to-those-with-extreme-cholesterol.html; Last Update: unknown; Accessed on: Nov. 8, 2016.
Konrad et al. (2011) Lipids in Health and Disease 10(1):38 "Effects of currently prescribed LDL-C-lowering drugs on PCSK9 and implications for the next generation of LDL-C-lowering agents".
Kuiper (2015) Pharma ISA Poster "Statin use and low density lipoprotein cholesterol goal attainment among a high cardiovascular risk population in the Netherlands".
Li et al. (2009) Recent Patents on DNA and Gene Sequences 3(3):201-212 "Recent Patents on PCSK9: A New Target for Treating Hypercholesterolemia".
McPherson (2013) Journal of the American College of Cardiology 61(4):437-439 "Remnant Cholesterol: Non-(HDL-C + LDL-C) as a Coronary Artery Disease Risk Factor".
Miettinen et al. (1971) Circulation 44(5):842-850 "Cholesterol production in obesity".
Moon (2007) Cardiology 108:282-289 "Lipoprotein(a) and LDL Particle Size are Related to the Severity of Coronary Artery Disease".

(56) References Cited

OTHER PUBLICATIONS

Moriarty et al. (2015) J Clin Lipidol. 9(6):758-769 "Efficacy and safety of alirocumab versus ezetimibe in statin-intolerant patients, with a statin-re-challenge arm: The ODYSSEY Alternative randomized trial".

Moriarty (2015) 10th International Society for Apheresis Congress XP55317363, Cancun Mexico "PCSK9 Inhibitors and their Effect on Patients who are Statin Intolerant or Receiving Lipoprotein-apheresis".

Office Action Article 94(3) EP App No. 12701742.4 dated May 28, 2014.

Ray (2015) Clin Lipidol. 10(1):9-12 "Alirocumab: an investigational treatment for hypercholesterolemia".

Reyes-Soffer et al. (2015) Arterioscler Thromb Vasc Biol 35:A129 "Effects of a proprotein convertase subtilisin/kexin type 9 inhibitor, alirocumab, on lipid and lipoprotein metabolism in normal subjects".

Roth et al. (2015) J. Clin. Lipidol. 37(9):1945-1954 "Patient and physician perspectives on administration of the PCSK9 monoclonal antibody alirocumab, an injectable medication to lower LDL-C levels".

Roth et al. (2015) International Symposium on Atherosclerosis, Abstract No. 254 "Phase 3 Randomized Trial Evaluating Alirocumab Every Four Weeks Dosing as Add-on to Statin or as Monotherapy: ODYSSEY Choice I".

Saeedi and Frohlich (2016) Clinical Diabetes and Endocrinology 2:7 "Lipoprotein (a), an independent cardiovascular risk marker".

Sahebkar et al. (2013) Clinical Therapeutics 35(8):1082-1098 "New LDL-Cholesterol Lowering Therapies: Pharmacology, Clinical Trials, and Relevance to Acute Coronary Syndromes".

Shoji et al. (1998) J Am Soc Nephrol 9:1277-1284 "Intermediate-Density Lipoprotein as an Independent Risk Factor for Aortic Atherosclerosis in Hemodialysis Patients".

Stahl (2010) "Early Clinical Development #1 REGN727: anti-PCSK9," Regeneron Pharmaceuticals. Accessible on the Internet at URL: http://files.shareholder.com/downloads/REGN/0x0x387214/534aaeb6-5e66-4e8f-86a9-0f9cac20d72f/REGN%20Investor%20Day%20Early%20Clinical%20Development1.pdf.

Steinberg et al. (2009) Proceedings of the National Academy of Sciences USA 106(24):9546-9547 "Inhibition of PCSK9: A powerful weapon for achieving ideal LDL cholesterol levels".

Stroes et al. (2014) J. Am. Coll. Cardiol. 63(23):2541-2548 "Anti-PCSK9 Antibody Effectively Lowers Cholesterol in Patients With Statin Intolerance".

Wang et al. (2007) Journal of Pharmaceutical Sciences 96(1):1-26 "Antibody Structure, Instability, and Formulation".

Wang et al. (2009) Clin. Pharmacology 49(9):1012-1024.

Westerterp et al. (2006) Vasc Biol 26(11):2552-2559 "Cholesteryl Ester Transfer Protein Decreases High-Density Lipoprotein and Severely Aggravates Atherosclerosis in APOE*3-Leiden Mice," Arterioscler Thromb.

Arai, Hidenori, "Dyslipidemia of diabetic patients" from new "Guidelines for prevention of arteriosclerostic diseases 2012 edition", Seasonal Post, (Diabetes network editorial department (SOUSINSYA), Sep. 1, 2012, vol. 4, No. 3, pp. 1-3. (with English Abstract translation).

McKee, Selina, PharmaTimes, "Praluent slashes need for apheresis treatment", Aug. 30, 2016. 2 pages.

Himmler, S. et al., Value in Health 20:A399-A811 (2017), Abstract No. PCV70, "Modelling the Societal Impact of Alirocumab in Patients with Severe Hypercholesterolemia Treated with Apheresis in Germany", 1 page.

Scott, Gale, MD Magazine, "PCSK9 Inhibitors: Weaning FH Patients off Apheresis", Aug. 29, 2016, 2 pages.

Julius, Ulrich, "Current Role of Lipoprotein Apheresis in the Treatment of High-Risk Patients", J. Cardiovasc. Dev & Dis., 2018, 5, 27, 11 pages.

Walji, Shahenaz et al., "Lipoprotein apheresis for the treatment of familial hypercholesterolemia", Clin. Lipidol. 2013, 8(5):573-586.

Anonymous: "NCT02326220 on Dec. 28, 2014: ClinicalTrials.gov Archive", Retrieved from the Internet: (https://clinicaltrials.gov/archive/NCT02326220/2014_12_28), retrieved on Nov. 7, 2016, 5 pages.

Anonymous: ""NCT02326220 on Mar. 10, 2015: ClinicalTrials.gov Archive"", Retrieved from the Internet: (https://clinicaltrials.gov/archive/NCT02326220/2015_03_10), retrieved on-Nov. 7, 2016, 5 pgs.

Anonymous: ""NCT02326220 on Apr. 7, 2015: ClinicalTrials.gov Archive"", Retrieved from the Internet: (https:// cinicaltrials.gov/archive/NCT02326220/2015_04_07), retrieved on-Nov. 7, 2016, 5 pgs.

* cited by examiner

SEQUENCE LISTING

<160> NUMBER OF SEQ ID NOS: 198

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Asn Asn Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Gly Ser Gly Gly Thr Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Asp Ser Asn Trp Gly Asn Phe Asp Leu
1               5                   10

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic REGN727 heavy chain polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

Ser Thr Ile Ser Gly Ser Gly Gly Thr Thr Asn Tyr Ala Asp Ser Val
    50                  55                  60

Lys Gly Arg Phe Ile Ile Ser Arg Asp Ser Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
            435                 440                 445

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Val Leu Tyr Arg Ser Asn Asn Arg Asn Phe
1               5                   10

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ala Ser
1

<210> SEQ ID NO 9
<211> LENGTH: 220
<212> TYPE: PRT
<213> ORGANISM: Artificial Sequence
<220> FEATURE:
<223> OTHER INFORMATION: Description of Artificial Sequence: Synthetic
      REGN727 light chain polypeptide
```

<400> SEQUENCE: 9

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45

Pro Pro Asn Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Gln Gln Tyr Tyr Thr Thr Pro Tyr Thr
1               5
```

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Glu Met Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Lys Trp Val Arg Gln Ala Pro Gly Lys Gly Leu Glu Trp Val
        35                  40                  45
```

Ala Asn Ile Asn Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
             85                  90                  95

Ala Arg Asp Ile Val Leu Met Val Tyr Asp Met Asp Tyr Tyr Tyr Tyr
                100                 105                 110

Gly Met Asp Val Trp Gly Gln Gly Thr Thr Val Thr Val Ser Ser
            115                 120                 125

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Thr Phe Ser Ser His Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn Gln Asp Gly Ser Glu Lys
1               5

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Asp Ile Val Leu Met Val Tyr Asp Met Asp Tyr Tyr Tyr Tyr
1               5                   10                  15

Gly Met Asp Val
            20

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                 85                  90                  95

Leu Gln Thr Pro Leu Thr Phe Gly Gly Gly Thr Lys Val Glu Ile Lys
            100                 105                 110

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Leu Leu His Ser Asn Gly Asn Asn Tyr
 1               5                   10

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gly Ser
 1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gln Thr Leu Gln Thr Pro Leu Thr
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Ser His Trp
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ile Asn Gln Asp Gly Ser Glu Lys
1               5
```

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Ala Arg Asp Ile Val Leu Met Val Tyr Asp Met Asp Tyr Tyr Tyr
1               5                   10                  15

Gly Met Asp Val
            20
```

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Gln Ser Leu His His Ser Asn Gly Asn Asn Tyr
1               5                   10
```

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Leu Gly Ser
1
```

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Met Gln Thr Leu Gln Thr Pro Leu Thr
1               5
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Gly Phe Thr Phe Ser Ser His Trp
1               5
```

<210> SEQ ID NO 26

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Asn Gln Asp Gly Ser Glu Lys
1               5

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Asp Ile Val Leu Met Val Tyr His Met Asp Tyr Tyr Tyr Tyr
1               5                   10                  15

Gly Met Asp Val
            20

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Leu Leu His Ser Asn Gly Asn Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Gly Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Gln Thr Leu Gln Thr Pro Leu Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Gly Phe Thr Phe Ser Ser His Trp
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Asn Gln Asp Gly Ser Glu Lys
1               5

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asp Ile Val Leu Met Val Tyr His Met Asp Tyr Tyr Tyr Tyr
1               5                   10                  15

Gly Met Asp Val
            20

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Leu His His Ser Asn Gly Asn Asn Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Gly Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Gln Thr Leu Gln Thr Pro Leu Thr
1               5
```

<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: Synthetic
      VH; m2CX1D05 polypeptide

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
            20                  25                  30

Ala Ile Ser Trp Val Arg Gln Ala Pro Gly Gln Gly Leu Glu Trp Met
        35                  40                  45

Gly Gly Ile Asn Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
            100                 105                 110

Tyr Leu Met Tyr Arg Phe Ala Ser Trp Gly Gln Gly Thr Leu Val Thr
        115                 120                 125

Val Ser Ser
    130

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; m2CX1D05 peptide

<400> SEQUENCE: 38

Gly Gly Thr Phe Asn Ser His Ala Ile Ser
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; m2CX1D05 peptide

<400> SEQUENCE: 39

Trp Met Gly Gly Ile Asn Pro Ile Leu Gly Ile Ala Asn Tyr Ala Gln
1               5                   10                  15

Lys Phe Gln Gly
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      VH CDR3; m2CX1D05 peptide

<400> SEQUENCE: 40

His Tyr Glu Ile Gln Ile Gly Arg Tyr Gly Met Asn Val Tyr Tyr Leu
1               5                   10                  15

Met Tyr Arg Phe Ala Ser
            20

<210> SEQ ID NO 41
<211> LENGTH: 213
<212> TYPE: PRT
<213> ORGANISM: Artificial Sequence
<220> FEATURE:
<223> OTHER INFORMATION: Description of Artificial Sequence: Synthetic
      LC; m2CX1D05 polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Ala
    210

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR 1; m2CX1D05 peptide

<400> SEQUENCE: 42

Arg Ala Ser Gln Gly Ile Arg Ser Ala Leu Asn
1               5                   10

<210> SEQ ID NO 43
<211> LENGTH: 11
<212> TYPE: PRT
<213> ORGANISM: Artificial Sequence

```
<220> FEATURE:
<223> OTHER INFORMATION: Description of Artificial Sequence: Synthetic
      VL CDR2; m2CX1D05 peptide

<400> SEQUENCE: 43

Leu Leu Ile Tyr Asn Gly Ser Thr Leu Gln Ser
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR3; m2CX1D05 peptide

<400> SEQUENCE: 44

Gln Gln Phe Asp Gly Asp Pro
1               5

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      VH; 1B20 polypeptide

<400> SEQUENCE: 45

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; 1B20 peptide

<400> SEQUENCE: 46

Gly Tyr Ser Phe Thr Asn Tyr Trp Ile Ser
1               5                   10

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
```

VH CDR2; 1B20 peptide

<400> SEQUENCE: 47

Trp Met Gly Ile Ile Tyr Pro Gly Asp Ser Tyr Thr Asn Tyr Ser Pro
1               5                   10                  15

Ser Phe Gln Gly
            20

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR3; 1B20 peptide

<400> SEQUENCE: 48

Asp Tyr Trp Tyr Lys Pro Leu Phe Asp Ile
1               5                   10

<210> SEQ ID NO 49
<211> LENGTH: 220
<212> TYPE: PRT
<213> ORGANISM: Artificial Sequence
<220> FEATURE:
<223> OTHER INFORMATION: Description of Artificial Sequence: Synthetic
      LC; 1B20 polypeptide

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Ala
    210                 215                 220

<210> SEQ ID NO 50

<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1; 1B20 peptide

<400> SEQUENCE: 50

Arg Ser Ser Gln Ser Val Leu Tyr Ser Ser Asn Asn Lys Asn Tyr Leu
1               5                   10                  15
Ala

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; 1B20 peptide

<400> SEQUENCE: 51

Leu Leu Ile Tyr Trp Ala Ser Thr Arg Glu Ser
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      VL CDR3; 1B20 peptide

<400> SEQUENCE: 52

Gln Gln Tyr Ser Ser Phe Pro Ile
1               5

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 54

```
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 heavy chain CDR1 antibody region peptide

<400> SEQUENCE: 54

Lys Ala Ser Gly Tyr Thr Phe Ser Ser Tyr Gly Met Tyr Trp Val Arg
1               5                   10                  15

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      AX132 heavy chain CDR2 antibody region peptide

<400> SEQUENCE: 55

Trp Ile Gly Trp Ile Asp Pro Gly Ser Gly Gly Thr Lys Tyr Asn Glu
1               5                   10                  15

Lys Phe Lys Gly Lys Ala Thr
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      AX132 heavy chain CDR3 antibody region peptide

<400> SEQUENCE: 56

Cys Ala Arg Glu Arg Tyr Gly Tyr Tyr Phe Asp Tyr Trp Gly Gln
1               5                   10                  15

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 57

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 58
<211> LENGTH: 17
<212> TYPE: PRT
```

<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 58

Ile Thr Cys Arg Ala Ser Gln Tyr Val Gly Ser Tyr Leu Asn Trp Tyr
1               5                   10                  15

Gln

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR2 antibody region peptide

<400> SEQUENCE: 59

Leu Ile Tyr Asp Ala Ser Asn Arg Ala Thr Gly Ile Pro
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 & AX213 light chain CDR3 antibody region peptide

<400> SEQUENCE: 60

Tyr Tyr Cys Gln Val Trp Asp Ser Ser Pro Pro Val Val Phe Gly Gly
1               5                   10                  15

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
                20                  25                  30

Gly Ile Asn Trp Val Arg Gln Ala Pro Gly Lys Gly Leu Glu Trp Ile
            35                  40                  45

Gly Arg Ile Asp Pro Gly Asn Gly Gly Thr Arg Tyr Asn Glu Lys Phe
        50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
        115                 120

<210> SEQ ID NO 62
<211> LENGTH: 16
<212> TYPE: PRT

```
<213> ORGANISM: Artificial Sequence
<220> FEATURE:
<223> OTHER INFORMATION: Description of Artificial Sequence: Synthetic
      AX213 heavy chain CDR1 antibody region peptide

<400> SEQUENCE: 62

Lys Ala Ser Gly Tyr Thr Phe Ser Arg Tyr Gly Ile Asn Trp Val Arg
1               5                   10                  15

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      AX213 heavy chain CDR2 antibody region peptide

<400> SEQUENCE: 63

Trp Ile Gly Arg Ile Asp Pro Gly Asn Gly Gly Thr Arg Tyr Asn Glu
1               5                   10                  15

Lys Phe Lys Gly Lys Ala Thr
            20

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      AX213 heavy chain CDR3 antibody region peptide

<400> SEQUENCE: 64

Cys Ala Arg Ala Asn Asp Gly Tyr Ser Phe Asp Tyr Trp Gly Gln
1               5                   10                  15

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 65

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 66
<211> LENGTH: 17
<212> TYPE: PRT
<213> ORGANISM: Artificial Sequence
<220> FEATURE:
```

-continued

<223> OTHER INFORMATION: Description of Artificial Sequence: Synthetic
     AX213 and AX132 light chain CDR1 antibody region peptide

<400> SEQUENCE: 66

Ile Thr Cys Arg Ala Ser Gln Tyr Val Gly Ser Tyr Leu Asn Trp Tyr
1               5                   10                  15
Gln

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
     AX213 and AX132 light chain CDR2 antibody region peptide

<400> SEQUENCE: 67

Leu Ile Tyr Asp Ala Ser Asn Arg Ala Thr Gly Ile Pro
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
     AX132 & AX213 light chain CDR3 antibody region peptide

<400> SEQUENCE: 68

Tyr Tyr Cys Gln Val Trp Asp Ser Ser Pro Val Val Phe Gly Gly
1               5                   10                  15

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
     AX1 VH antibody sequence polypeptide

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30

Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser
        115

<210> SEQ ID NO 70
<211> LENGTH: 16
<212> TYPE: PRT
<213> ORGANISM: Artificial Sequence
<220> FEATURE:

<223> OTHER INFORMATION: Description of Artificial Sequence: Synthetic
     AX1 VH CDR1 antibody sequence peptide

<400> SEQUENCE: 70

Lys Ala Ser Gly Phe Thr Phe Thr Ser Tyr Tyr Met His Trp Val Arg
1               5                   10                  15

<210> SEQ ID NO 71
<211> LENGTH: 23
<212> TYPE: PRT
<213> ORGANISM: Artificial Sequence
<220> FEATURE:
<223> OTHER INFORMATION: Description of Artificial Sequence: Synthetic
     AX1 VH CDR2 antibody sequence peptide

<400> SEQUENCE: 71

Trp Ile Gly Arg Ile Asn Pro Asp Ser Gly Ser Thr Lys Tyr Asn Glu
1               5                   10                  15

Lys Phe Lys Gly Arg Ala Thr
            20

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
     AX1 VH CDR3 antibody sequence peptide

<400> SEQUENCE: 72

Cys Ala Arg Gly Gly Arg Leu Ser Trp Asp Phe Asp Val Trp Gly Gln
1               5                   10                  15

<210> SEQ ID NO 73
<211> LENGTH: 109
<212> TYPE: PRT
<213> ORGANISM: Artificial Sequence
<220> FEATURE:
<223> OTHER INFORMATION: Description of Artificial Sequence: Synthetic
     AX1 VL antibody sequence polypeptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys
            100                 105

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
     AX1 VL CDR1 antibody sequence peptide

<400> SEQUENCE: 74

Arg Ala Ser Gln Asp Ile Ser Arg Tyr Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      AX1 AX9 AX189 VL CDR2 antibody sequence peptide

<400> SEQUENCE: 75

Ala Ala Ser Ser Leu Gln Ser
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR3 antibody sequence peptide

<400> SEQUENCE: 76

Ala Ala Tyr Asp Tyr Ser Leu Gly Gly Tyr Val
1               5                   10

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      AX9 AX189 VH antibody sequence polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Gly Ser Tyr Ala Met Asp Tyr Trp Gly
            100                 105                 110

Gln Gly Thr Leu Val Thr Val Ser Ser
        115                 120

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      AX9 AX189 VH CDR1 antibody sequence peptide

<400> SEQUENCE: 78

```
Lys Ala Ser Gly Tyr Thr Phe Ser Ser Tyr Trp Met His Trp Val Arg
1               5                   10                  15
```

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
      AX9 AX189 VH CDR2 antibody sequence peptide

<400> SEQUENCE: 79

```
Trp Ile Gly Arg Ile Asp Pro Tyr Asn Gly Gly Thr Lys Tyr Asn Glu
1               5                   10                  15

Lys Phe Lys Gly Lys Ala Thr
            20
```

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      AX9 AX189 VH CDR3 antibody sequence peptide

<400> SEQUENCE: 80

```
Cys Ala Arg Tyr Gly Tyr Tyr Leu Gly Ser Tyr Ala Met Asp Tyr Trp
1               5                   10                  15

Gly Gln
```

<210> SEQ ID NO 81
<211> LENGTH: 109
<212> TYPE: PRT
<213> ORGANISM: Artificial Sequence
<220> FEATURE:
<223> OTHER INFORMATION: Description of Artificial Sequence: Synthetic
      AX189 VL antibody sequence polypeptide

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys
            100                 105
```

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      AX189 VL CDR1 antibody sequence peptide

<400> SEQUENCE: 82

```
Arg Ala Ser Gln Asp Val Ser Arg Tyr Leu Thr
1               5                   10
```

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      AX1 AX9 AX189 VL CDR2 antibody sequence peptide

<400> SEQUENCE: 83

```
Ala Ala Ser Ser Leu Gln Ser
1               5
```

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      AX189 VL CDR3 antibody sequence peptide

<400> SEQUENCE: 84

```
Gln Ala Tyr Asp Tyr Ser Leu Ser Gly Tyr Val
1               5                   10
```

<210> SEQ ID NO 85
<211> LENGTH: 115
<212> TYPE: PRT
<213> ORGANISM: Homo sapiens

<400> SEQUENCE: 85

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115
```

<210> SEQ ID NO 86
<211> LENGTH: 5
<212> TYPE: PRT
<213> ORGANISM: Homo sapiens

<400> SEQUENCE: 86

```
Ser Tyr Gly Ile Ser
1               5
```

<210> SEQ ID NO 87
<211> LENGTH: 17
<212> TYPE: PRT

<213> ORGANISM: Homo sapiens

<400> SEQUENCE: 87

Trp Val Ser Phe Tyr Asn Gly Asn Thr Asn Tyr Ala Gln Lys Leu Gln
1               5                   10                  15
Gly

<210> SEQ ID NO 88
<211> LENGTH: 6
<212> TYPE: PRT
<213> ORGANISM: Homo sapiens

<400> SEQUENCE: 88

Gly Tyr Gly Met Asp Val
1               5

<210> SEQ ID NO 89
<211> LENGTH: 109
<212> TYPE: PRT
<213> ORGANISM: Homo sapiens

<400> SEQUENCE: 89

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 90
<211> LENGTH: 14
<212> TYPE: PRT
<213> ORGANISM: Homo sapiens

<400> SEQUENCE: 90

Thr Gly Thr Ser Ser Asp Val Gly Gly Tyr Asn Ser Val Ser
1               5                   10

<210> SEQ ID NO 91
<211> LENGTH: 7
<212> TYPE: PRT
<213> ORGANISM: Homo sapiens

<400> SEQUENCE: 91

Glu Val Ser Asn Arg Pro Ser
1               5

<210> SEQ ID NO 92
<211> LENGTH: 9
<212> TYPE: PRT
<213> ORGANISM: Homo sapiens

<400> SEQUENCE: 92

Asn Ser Tyr Thr Ser Thr Ser Met Val
1               5

<210> SEQ ID NO 93
<211> LENGTH: 123
<212> TYPE: PRT
<213> ORGANISM: Homo sapiens

<400> SEQUENCE: 93

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Tyr Asp Phe Trp Ser Ala Tyr Tyr Asp Ala Phe Asp Val
            100                 105                 110

Trp Gly Gln Gly Thr Met Val Thr Val Ser Ser
        115                 120

<210> SEQ ID NO 94
<211> LENGTH: 10
<212> TYPE: PRT
<213> ORGANISM: Homo sapiens

<400> SEQUENCE: 94

Gly Phe Thr Phe Ser Ser Tyr Ser Met Asn
1               5                   10

<210> SEQ ID NO 95
<211> LENGTH: 17
<212> TYPE: PRT
<213> ORGANISM: Homo sapiens

<400> SEQUENCE: 95

Ser Ile Ser Ser Ser Ser Tyr Ile Ser Tyr Ala Asp Ser Val Lys
1               5                   10                  15

Gly

<210> SEQ ID NO 96
<211> LENGTH: 14
<212> TYPE: PRT
<213> ORGANISM: Homo sapiens

<400> SEQUENCE: 96

Asp Tyr Asp Phe Trp Ser Ala Tyr Tyr Asp Ala Phe Asp Val
1               5                   10

<210> SEQ ID NO 97
<211> LENGTH: 111
<212> TYPE: PRT
<213> ORGANISM: Homo sapiens

<400> SEQUENCE: 97

Gln Ser Val Leu Thr Gln Pro Pro Ser Val Ser Gly Ala Pro Gly Gln

```
                1               5                  10                 15
            Arg Val Thr Ile Ser Cys Thr Gly Ser Ser Asn Ile Gly Ala Gly
                            20                 25                 30
            Tyr Asp Val His Trp Tyr Gln Gln Leu Pro Gly Thr Ala Pro Lys Leu
                        35                 40                 45
            Leu Ile Ser Gly Asn Ser Asn Arg Pro Ser Gly Val Pro Asp Arg Phe
                    50                 55                 60
            Ser Gly Ser Lys Ser Gly Thr Ser Ala Ser Leu Ala Ile Thr Gly Leu
            65                 70                 75                 80
            Gln Ala Glu Asp Glu Ala Asp Tyr Tyr Cys Gln Ser Tyr Asp Ser Ser
                            85                 90                 95
            Leu Ser Gly Ser Val Phe Gly Gly Gly Thr Lys Leu Thr Val Leu
                        100                105                110
```

<210> SEQ ID NO 98
<211> LENGTH: 14
<212> TYPE: PRT
<213> ORGANISM: Homo sapiens

<400> SEQUENCE: 98

```
Thr Gly Ser Ser Ser Asn Ile Gly Ala Gly Tyr Asp Val His
1               5                  10
```

<210> SEQ ID NO 99
<211> LENGTH: 7
<212> TYPE: PRT
<213> ORGANISM: Homo sapiens

<400> SEQUENCE: 99

```
Gly Asn Ser Asn Arg Pro Ser
1               5
```

<210> SEQ ID NO 100
<211> LENGTH: 11
<212> TYPE: PRT
<213> ORGANISM: Homo sapiens

<400> SEQUENCE: 100

```
Gln Ser Tyr Asp Ser Ser Leu Ser Gly Ser Val
1               5                  10
```

<210> SEQ ID NO 101
<211> LENGTH: 114
<212> TYPE: PRT
<213> ORGANISM: Homo sapiens

<400> SEQUENCE: 101

```
Gln Val Gln Leu Val Glu Ser Gly Gly Gly Val Ala Gln Pro Gly Arg
1               5                  10                 15
Ser Leu Arg Leu Ser Cys Ala Ala Ser Gly Phe Thr Phe Ser Ser Tyr
                20                 25                 30
Gly Met His Trp Val Arg Gln Ala Pro Gly Lys Gly Leu Glu Trp Val
            35                 40                 45
Ala Val Ile Tyr Tyr Asp Gly Ile Asn Lys His Tyr Ala Asp Ser Val
        50                 55                 60
Lys Gly Arg Phe Thr Ile Ser Arg Asp Asn Ser Lys Asn Thr Leu Tyr
65                 70                 75                 80
Leu Gln Met Asn Ser Leu Arg Ala Glu Asp Thr Ala Val Tyr Tyr Cys
                85                 90                 95
```

Ala Arg Asp Arg Gly Leu Asp Trp Gly Gln Gly Thr Leu Val Thr Val
            100                 105                 110

Ser Ser

<210> SEQ ID NO 102
<211> LENGTH: 10
<212> TYPE: PRT
<213> ORGANISM: Homo sapiens

<400> SEQUENCE: 102

Gly Phe Thr Phe Ser Ser Tyr Gly Met His
1               5                   10

<210> SEQ ID NO 103
<211> LENGTH: 17
<212> TYPE: PRT
<213> ORGANISM: Homo sapiens

<400> SEQUENCE: 103

Val Ile Tyr Tyr Asp Gly Ile Asn Lys His Tyr Ala Asp Ser Val Lys
1               5                   10                  15

Gly

<210> SEQ ID NO 104
<211> LENGTH: 5
<212> TYPE: PRT
<213> ORGANISM: Homo sapiens

<400> SEQUENCE: 104

Asp Arg Gly Leu Asp
1               5

<210> SEQ ID NO 105
<211> LENGTH: 113
<212> TYPE: PRT
<213> ORGANISM: Homo sapiens

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 106
<211> LENGTH: 17
<212> TYPE: PRT
<213> ORGANISM: Homo sapiens

<400> SEQUENCE: 106

```
Lys Ser Ser Gln Ser Val Leu Tyr Ser Ser Asn Ser Lys Asn Tyr Leu
1               5                   10                  15
Val
```

<210> SEQ ID NO 107
<211> LENGTH: 7
<212> TYPE: PRT
<213> ORGANISM: Homo sapiens

<400> SEQUENCE: 107

```
Trp Ala Ser Thr Arg Glu Ser
1               5
```

<210> SEQ ID NO 108
<211> LENGTH: 9
<212> TYPE: PRT
<213> ORGANISM: Homo sapiens

<400> SEQUENCE: 108

```
Gln Gln Tyr Tyr Ser Thr Pro Trp Thr
1               5
```

<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04 (clones LGT-209 and
      LGT-210) Vh heavy chain variable region (FR1-FR4)
      polypeptide

<400> SEQUENCE: 109

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
                20                  25                  30

Tyr Met Ser Trp Val Arg Gln Ala Pro Gly Gln Gly Leu Glu Trp Met
            35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Thr Ala Val Tyr Tyr Cys
                85                  90                  95

Ala Arg Ser Tyr Tyr Tyr Tyr Asn Met Asp Tyr Trp Gly Gln Gly Thr
                100                 105                 110

Leu Val Thr Val Ser Ser
        115
```

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 heavy chain CDR1 peptide

<400> SEQUENCE: 110

```
Thr Met Tyr Met Ser
1               5
```

<210> SEQ ID NO 111
<211> LENGTH: 17
<212> TYPE: PRT
<213> ORGANIZM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 heavy chain CDR2 peptide

<400> SEQUENCE: 111

Arg Ile Asp Pro Ala Asn Glu His Thr Asn Tyr Ala Gln Lys Phe Gln
1               5                   10                  15

Gly

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04(clones
      LGT-209 and LGT-210) Vh heavy chain complementarity
      determining region 3 (CDR3) peptide

<400> SEQUENCE: 112

Ser Tyr Tyr Tyr Tyr Asn Met Asp Tyr
1               5

<210> SEQ ID NO 113
<211> LENGTH: 106
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG10(clones
      LGT-209 and LGT-211) Vk light chain variable
      region (FR1-FR4) polypeptide

<400> SEQUENCE: 113

Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
                20                  25                  30

His Trp Tyr Gln Gln Lys Pro Gly Gln Ala Pro Arg Leu Leu Ile Tyr
            35                  40                  45

Gly Val Phe Arg Arg Ala Thr Gly Ile Pro Asp Arg Phe Ser Gly Ser
        50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 light chain CDR1 peptide

<400> SEQUENCE: 114

```
Arg Ala Ser Gln Ser Val Ser Tyr Met His
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 light chain CDR1 peptide

<400> SEQUENCE: 115

Gly Val Phe Arg Arg Ala Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      mouse anti-PCSK9 monoclonal antibody LFU720 and
      anti-PCSK9 monoclonal antibody clones LGT-209,
      LGT-210 and LGT-211 light chain CDR3 peptide

<400> SEQUENCE: 116

Leu Gln Trp Ser Ser Asp Pro Pro Thr
1               5

<210> SEQ ID NO 117
<211> LENGTH: 118
<212> TYPE: PRT
<213> ORGANISM: Homo sapiens

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Tyr Thr Phe Thr Ser Tyr
1               5
```

-continued

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Pro Phe Gly Gly Arg
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      variable heavy chain CDR peptide

<400> SEQUENCE: 120

Glu Arg Pro Leu Tyr Ala Ser Asp Leu
1               5

<210> SEQ ID NO 121
<211> LENGTH: 107
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 122

Arg Ala Ser Gln Gly Ile Ser Ser Ala Leu Ala
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic variable light chain CDR peptide

<400> SEQUENCE: 123

Ser Ala Ser Tyr Arg Tyr Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 124

Gln Gln Arg Tyr Ser Leu Trp Arg Thr
1               5

<210> SEQ ID NO 125
<211> LENGTH: 118
<212> TYPE: PRT
<213> ORGANISM: Homo sapiens

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Met Asp Tyr Trp Gly Gln Gly Thr
            100                 105                 110

Thr Val Thr Val Ser Ser
        115

<210> SEQ ID NO 126
<211> LENGTH: 10
<212> TYPE: PRT
<213> ORGANISM: Homo sapiens

<400> SEQUENCE: 126

Gly Tyr Thr Phe Thr Ser Tyr Tyr Met His
1               5                   10

<210> SEQ ID NO 127
<211> LENGTH: 17
<212> TYPE: PRT
<213> ORGANISM: Homo sapiens

<400> SEQUENCE: 127

Glu Ile His Pro Ser Gly Gly Arg Thr Asn Tyr Asn Glu Lys Phe Lys
1               5                   10                  15

Ser

<210> SEQ ID NO 128

-continued

```
<211> LENGTH: 9
<212> TYPE: PRT
<213> ORGANISM: Homo sapiens

<400> SEQUENCE: 128

Glu Arg Pro Leu Tyr Ala Met Asp Tyr
1               5

<210> SEQ ID NO 129
<211> LENGTH: 107
<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 130
<211> LENGTH: 11
<212> TYPE: PRT
<213> ORGANISM: Homo sapiens

<400> SEQUENCE: 130

Lys Ala Ser Gln Asp Val His Thr Ala Val Ala
1               5                   10

<210> SEQ ID NO 131
<211> LENGTH: 7
<212> TYPE: PRT
<213> ORGANISM: Homo sapiens

<400> SEQUENCE: 131

His Ala Ser Tyr Arg Tyr Thr
1               5

<210> SEQ ID NO 132
<211> LENGTH: 9
<212> TYPE: PRT
<213> ORGANISM: Homo sapiens

<400> SEQUENCE: 132

Gln Gln Arg Tyr Ser Leu Trp Arg Thr
1               5

<210> SEQ ID NO 133
<211> LENGTH: 118
<212> TYPE: PRT
<213> ORGANISM: Homo sapiens

<400> SEQUENCE: 133
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
            115

<210> SEQ ID NO 134
<211> LENGTH: 10
<212> TYPE: PRT
<213> ORGANISM: Homo sapiens

<400> SEQUENCE: 134

Gly Tyr Thr Phe Thr Ser Tyr Tyr Met His
1               5                   10

<210> SEQ ID NO 135
<211> LENGTH: 17
<212> TYPE: PRT
<213> ORGANISM: Homo sapiens

<400> SEQUENCE: 135

Glu Ile His Pro Ser Gly Gly Arg Thr Asn Tyr Asn Glu Lys Phe Lys
1               5                   10                  15

Ser

<210> SEQ ID NO 136
<211> LENGTH: 9
<212> TYPE: PRT
<213> ORGANISM: Homo sapiens

<400> SEQUENCE: 136

Glu Arg Pro Leu Tyr Ala Ser Asp Leu
1               5

<210> SEQ ID NO 137
<211> LENGTH: 107
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
50                  55                  60

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Arg Tyr Ser Leu Trp Arg
                 85                  90                  95

Thr Phe Gly Gln Gly Thr Lys Leu Glu Ile Lys
                100                 105
```

<210> SEQ ID NO 138
<211> LENGTH: 11
<212> TYPE: PRT
<213> ORGANISM: Homo sapiens

<400> SEQUENCE: 138

```
Lys Ala Ser Gln Asp Val His Thr Ala Val Ala
 1               5                  10
```

<210> SEQ ID NO 139
<211> LENGTH: 7
<212> TYPE: PRT
<213> ORGANISM: Homo sapiens

<400> SEQUENCE: 139

```
His Ala Ser Tyr Arg Tyr Thr
 1               5
```

<210> SEQ ID NO 140
<211> LENGTH: 9
<212> TYPE: PRT
<213> ORGANISM: Homo sapiens

<400> SEQUENCE: 140

```
Gln Gln Arg Tyr Ser Leu Trp Arg Thr
 1               5
```

<210> SEQ ID NO 141
<211> LENGTH: 118
<212> TYPE: PRT
<213> ORGANISM: Mus musculus

<400> SEQUENCE: 141

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
             35                  40                  45

Gly Glu Ile Asn Pro Ser Asn Gly Arg Thr Asn Tyr Asn Glu Lys Phe
 50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Arg Pro Leu Tyr Ala Met Asp Tyr Trp Gly Gln Gly Thr
                100                 105                 110

Ser Val Thr Val Ser Ser
            115
```

<210> SEQ ID NO 142
<211> LENGTH: 7
<212> TYPE: PRT
<213> ORGANISM: Mus musculus

<400> SEQUENCE: 142

Gly Tyr Thr Phe Thr Ser Tyr
1               5

<210> SEQ ID NO 143
<211> LENGTH: 6
<212> TYPE: PRT
<213> ORGANISM: Mus musculus

<400> SEQUENCE: 143

Asn Pro Ser Asn Gly Arg
1               5

<210> SEQ ID NO 144
<211> LENGTH: 9
<212> TYPE: PRT
<213> ORGANISM: Mus musculus

<400> SEQUENCE: 144

Glu Arg Pro Leu Tyr Ala Met Asp Tyr
1               5

<210> SEQ ID NO 145
<211> LENGTH: 108
<212> TYPE: PRT
<213> ORGANISM: Mus musculus

<400> SEQUENCE: 145

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Arg Tyr Ser Thr Pro Arg
                85                  90                  95

Thr Phe Gly Gly Gly Thr Lys Leu Glu Ile Lys Arg
            100                 105

<210> SEQ ID NO 146
<211> LENGTH: 11
<212> TYPE: PRT
<213> ORGANISM: Mus musculus

<400> SEQUENCE: 146

Lys Ala Ser Gln Asp Val Ser Thr Ala Val Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 147

Ser Ala Ser Tyr Arg Tyr Thr
1               5

<210> SEQ ID NO 148
<211> LENGTH: 9
<212> TYPE: PRT
<213> ORGANISM: Mus musculus

<400> SEQUENCE: 148

Gln Gln Arg Tyr Ser Thr Pro Arg Thr
1               5

<210> SEQ ID NO 149
<211> LENGTH: 115
<212> TYPE: PRT
<213> ORGANISM: Mus musculus

<400> SEQUENCE: 149

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Thr Thr Tyr Asn Gln Lys Phe
        50                  55                  60

Lys Gly Lys Ala Thr Leu Thr Val Asp Lys Ser Tyr Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Leu Leu Phe Ala Tyr Trp Gly Gln Gly Thr Leu Val Thr
                100                 105                 110

Val Ser Ala
        115

<210> SEQ ID NO 150
<211> LENGTH: 7
<212> TYPE: PRT
<213> ORGANISM: Mus musculus

<400> SEQUENCE: 150

Gly Tyr Thr Phe Thr Asp Tyr
1               5

<210> SEQ ID NO 151
<211> LENGTH: 6
<212> TYPE: PRT
<213> ORGANISM: Mus musculus

<400> SEQUENCE: 151

Asn Pro Asn Asn Gly Gly
1               5

<210> SEQ ID NO 152
<211> LENGTH: 6
<212> TYPE: PRT
<213> ORGANISM: Mus musculus

<400> SEQUENCE: 152

Trp Leu Leu Phe Ala Tyr
1               5

<210> SEQ ID NO 153
<211> LENGTH: 108
<212> TYPE: PRT
<213> ORGANISM: Mus musculus

<400> SEQUENCE: 153

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Leu Ser
65                  70                  75                  80

Glu Asp Leu Ala Glu Tyr Phe Cys Gln Gln Phe Tyr Ser Tyr Pro Tyr
                85                  90                  95

Thr Phe Gly Gly Gly Thr Lys Leu Glu Ile Lys Arg
            100                 105

<210> SEQ ID NO 154
<211> LENGTH: 11
<212> TYPE: PRT
<213> ORGANISM: Mus musculus

<400> SEQUENCE: 154

Lys Ala Ser Gln Asn Val Gly Thr Asn Val Ala
1               5                   10

<210> SEQ ID NO 155
<211> LENGTH: 7
<212> TYPE: PRT
<213> ORGANISM: Mus musculus

<400> SEQUENCE: 155

Ser Ala Ser Tyr Arg Tyr Ser
1               5

<210> SEQ ID NO 156
<211> LENGTH: 9
<212> TYPE: PRT
<213> ORGANISM: Mus musculus

<400> SEQUENCE: 156

Gln Gln Phe Tyr Ser Tyr Pro Tyr Thr
1               5

<210> SEQ ID NO 157
<211> LENGTH: 123
<212> TYPE: PRT
<213> ORGANISM: Mus musculus

<400> SEQUENCE: 157

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

-continued

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Gly Gly Ile Tyr Tyr Arg Tyr Asp Arg Asn Tyr Phe Asp Tyr
            100                 105                 110

Trp Gly Gln Gly Thr Thr Leu Thr Val Ser Ser
            115                 120

<210> SEQ ID NO 158
<211> LENGTH: 7
<212> TYPE: PRT
<213> ORGANISM: Mus musculus

<400> SEQUENCE: 158

Gly Tyr Thr Phe Thr Asp Tyr
1               5

<210> SEQ ID NO 159
<211> LENGTH: 6
<212> TYPE: PRT
<213> ORGANISM: Mus musculus

<400> SEQUENCE: 159

Asn Pro Asn Asn Gly Gly
1               5

<210> SEQ ID NO 160
<211> LENGTH: 14
<212> TYPE: PRT
<213> ORGANISM: Mus musculus

<400> SEQUENCE: 160

Gly Gly Ile Tyr Tyr Arg Tyr Asp Arg Asn Tyr Phe Asp Tyr
1               5                   10

<210> SEQ ID NO 161
<211> LENGTH: 107
<212> TYPE: PRT
<213> ORGANISM: Mus musculus

<400> SEQUENCE: 161

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Phe
                85                  90                  95

Thr Phe Gly Ser Gly Thr Lys Leu Glu Ile Lys
            100                 105

<210> SEQ ID NO 162

```
<211> LENGTH: 11
<212> TYPE: PRT
<213> ORGANISM: Mus musculus

<400> SEQUENCE: 162

Ser Ala Ser Gln Gly Ile Ser Asn Tyr Leu Asn
1               5                   10

<210> SEQ ID NO 163
<211> LENGTH: 7
<212> TYPE: PRT
<213> ORGANISM: Mus musculus

<400> SEQUENCE: 163

Tyr Thr Ser Ser Leu His Ser
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Tyr Ser Lys Leu Pro Phe Thr
1               5

<210> SEQ ID NO 165
<211> LENGTH: 117
<212> TYPE: PRT
<213> ORGANISM: Mus musculus

<400> SEQUENCE: 165

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Asn Thr Ser Tyr Leu Asp Ser Leu
        50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Glu Lys Phe Ala Ala Met Asp Tyr Trp Gly Gln Gly Thr Ser
            100                 105                 110

Val Thr Val Ser Ser
        115

<210> SEQ ID NO 166
<211> LENGTH: 7
<212> TYPE: PRT
<213> ORGANISM: Mus musculus

<400> SEQUENCE: 166

Gly Phe Thr Phe Ser Asp Tyr
1               5

<210> SEQ ID NO 167
```

```
<211> LENGTH: 6
<212> TYPE: PRT
<213> ORGANISM: Mus musculus

<400> SEQUENCE: 167

Asn Tyr Asp Gly Ser Asn
1               5

<210> SEQ ID NO 168
<211> LENGTH: 8
<212> TYPE: PRT
<213> ORGANISM: Mus musculus

<400> SEQUENCE: 168

Glu Lys Phe Ala Ala Met Asp Tyr
1               5

<210> SEQ ID NO 169
<211> LENGTH: 108
<212> TYPE: PRT
<213> ORGANISM: Mus musculus

<400> SEQUENCE: 169

Asp Ile Val Met Thr Gln Ser His Lys Phe Met Ser Thr Ser Phe Gly
1               5                   10                  15

Asp Arg Val Ser Ile Thr Cys Lys Ala Ser Gln Asp Val Ser Asn Ala
            20                  25                  30

Leu Ala Trp Tyr Gln Gln Lys Pro Gly His Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys Arg
            100                 105

<210> SEQ ID NO 170
<211> LENGTH: 11
<212> TYPE: PRT
<213> ORGANISM: Mus musculus

<400> SEQUENCE: 170

Lys Ala Ser Gln Asp Val Ser Asn Ala Leu Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 171

Ser Ala Ser Tyr Arg Tyr Thr
1               5

<210> SEQ ID NO 172
<211> LENGTH: 9
<212> TYPE: PRT
<213> ORGANISM: Mus musculus
```

<400> SEQUENCE: 172

Gln Gln His Tyr Ser Thr Pro Trp Thr
1               5

<210> SEQ ID NO 173
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
            20                  25                  30

Thr Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Phe Thr Phe Thr Arg His Thr Ile His
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Ile Ser Pro Ala Asn Gly Asn Thr Asn Tyr Ala Asp Ser Val Lys
1               5                   10                  15

Gly

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Ile Gly Ser Arg Glu Leu Tyr Ile Met Asp Tyr
1               5                   10

<210> SEQ ID NO 177
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Ile Gln Pro
                85                  90                  95

Thr Phe Gly Gln Gly Thr Lys Val Glu Ile Lys Arg
            100                 105

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Ala Ser Gln Asp Val Ser Thr Ala Val Ala
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Ala Ser Phe Leu Tyr Ser
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gln Gln Ser Tyr Arg Ile Gln Pro Thr
1               5

<210> SEQ ID NO 181
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Ala Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Phe Thr Phe Ser Ser Thr Ala Ile His
1               5                   10

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ile Ser Pro Ala Asn Gly Asn Thr Asn Tyr Ala Asp Ser Val Lys
1               5                   10                  15

Gly

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Trp Ile Gly Ser Arg Glu Leu Tyr Ile Met Asp Tyr
1               5                   10

<210> SEQ ID NO 185
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Leu His
                85                  90                  95

Thr Phe Gly Gln Gly Thr Lys Val Glu Ile Lys Arg
            100                 105

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Ser Gln Asp Val Ser Thr Ala Val Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Ala Ser Phe Leu Tyr Ser
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Gln Ser Tyr Pro Ala Leu His Thr
1               5

<210> SEQ ID NO 189
<211> LENGTH: 125
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Lys Leu
            20                  25                  30

Gly Met Val Trp Val Arg Gln Ala Pro Gly Lys Gly Leu Glu Trp Val
        35                  40                  45

Ser Thr Ile Ser Ser Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser
        115                 120                 125

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Pro Phe Ser Lys Leu Gly Met Val
1               5                   10

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Ile Ser Ser Gly Gly Gly Tyr Thr Tyr Tyr Pro Asp Ser Val Lys
1               5                   10                  15

Gly

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Glu Gly Ile Ser Phe Gln Gly Gly Thr Tyr Thr Tyr Val Met Asp Tyr
1               5                   10                  15

<210> SEQ ID NO 193
<211> LENGTH: 112
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 193

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110
```

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

```
Arg Ser Ser Lys Ser Leu Leu His Arg Asn Gly Ile Thr Tyr Ser Tyr
1               5                   10                  15
```

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

```
Gln Leu Ser Asn Leu Ala Ser
1               5
```

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

```
Tyr Gln Asn Leu Glu Leu Pro Leu Thr
1               5
```

<210> SEQ ID NO 197
<211> LENGTH: 2076
<212> TYPE: DNA
<213> ORGANISM: Homo sapiens

<400> SEQUENCE: 197
atgggcaccg tcagctccag gcggtcctgg tggccgctgc cactgctgct gctgctgctg      60

```
ctgctcctgg gtcccgcggg cgcccgtgcg caggaggacg aggacggcga ctacgaggag      120
ctggtgctag ccttgcgttc cgaggaggac ggcctggccg aagcacccga gcacggaacc      180
acagccacct tccaccgctg cgccaaggat ccgtggaggt tgcctggcac ctacgtggtg      240
gtgctgaagg aggagaccca cctctcgcag tcagagcgca ctgcccgccg cctgcaggcc      300
caggctgccc gccggggata cctcaccaag atcctgcatg tcttccatgg ccttcttcct      360
ggcttcctgg tgaagatgag tggcgacctg ctggagctgg ccttgaagtt gccccatgtc      420
gactacatcg aggaggactc ctctgtcttt gcccagagca tcccgtggaa cctggagcgg      480
attacccctc cacggtaccg ggcggatgaa taccagcccc ccgacggagg cagcctggtg      540
gaggtgtatc tcctagacac cagcatacag agtgaccacc gggaaatcga gggcagggtc      600
atggtcaccg acttcgagaa tgtgcccgag gaggacggga cccgcttcca cagacaggcc      660
agcaagtgtg acagtcatgg cacccacctg gcaggggtgg tcagcggccg ggatgccggc      720
gtggccaagg tgccagcat gcgcagcctg cgcgtgctca actgccaagg gaagggcacg      780
gttagcggca ccctcatagg cctggagttt attcggaaaa gccagctggt ccagcctgtg      840
gggccactgg tggtgctgct gccccctggcg ggtgggtaca gccgcgtcct caacgccgcc      900
tgccagcgcc tggcgagggc tggggtcgtg ctggtcaccg ctgccggcaa cttccgggac      960
gatgcctgcc tctactcccc agcctcagct cccgaggtca tcacagttgg ggccaccaat     1020
gcccaagacc agccggtgac cctggggact ttggggacca actttggccg ctgtgtggac     1080
ctctttgccc cagggagga catcattggt gcctccagcg actgcagcac ctgctttgtg     1140
tcacagagtg ggacatcaca ggctgctgcc cacgtggctg gcattgcagc catgatgctg     1200
tctgccgagc cggagctcac cctggccgag ttgaggcaga gactgatcca cttctctgcc     1260
aaagatgtca tcaatgaggc ctggttccct gaggaccagc gggtactgac ccccaacctg     1320
gtggccgccc tgccccccag cacccatggg gcaggttggc agctgttttg caggactgta     1380
tggtcagcac actcggggcc tacacggatg gccacagccg tcgcccgctg cgccccagat     1440
gaggagctgc tgagctgctc cagtttctcc aggagtggga gcggcgggg cgagcgcatg     1500 gaggcccaag ggggcaagct ggtctgccgg gcccacaacg cttttggggg tgagggtgtc     1560
tacgccattg ccaggtgctg cctgctaccc caggccaact gcagcgtcca cacagctcca     1620
ccagctgagg ccagcatggg gacccgtgtc cactgccacc aacagggcca cgtcctcaca     1680
ggctgcagct cccactggga ggtggaggac cttggcaccc acaagccgcc tgtgctgagg     1740
ccacgaggtc agcccaacca gtgcgtgggc cacaggagg ccagcatcca cgcttcctgc     1800
tgccatgccc caggtctgga atgcaaagtc aaggagcatg gaatcccggc ccctcaggag     1860
caggtgaccg tggcctgcga ggagggctgg accctgactg gctgcagtgc cctccctggg     1920
acctcccacg tcctgggggc ctacgccgta gacaacacgt gtgtagtcag gagccgggac     1980
gtcagcacta caggcagcac cagcgaaggg gccgtgacag ccgttgccat ctgctgccgg     2040
agccggcacc tggcgcaggc ctcccaggag ctccag                               2076
```

<210> SEQ ID NO 198
<211> LENGTH: 692
<212> TYPE: PRT
<213> ORGANISM: Homo sapiens

<400> SEQUENCE: 198

```
Met Gly Thr Val Ser Ser Arg Arg Ser Trp Trp Pro Leu Pro Leu Leu
1               5                   10                  15
```

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

-continued

```
Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
        530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
                660                 665                 670

Thr Ala Val Ala Ile Cys Cys Arg Ser Arg His Leu Ala Gln Ala Ser
            675                 680                 685

Gln Glu Leu Gln
    690
```

METHODS FOR REDUCING OR ELIMINATING THE NEED FOR LIPOPROTEIN APHERESIS IN PATIENTS WITH HYPERLIPIDEMIA BY ADMINISTERING ALIROCUMAB

This application claims the benefit under 35 U.S.C. § 119(e) of U.S. provisional application No. 62/206,326, filed on Aug. 18, 2015; 62/264,361, filed on Dec. 8, 2015; 62/270,790, filed on Dec. 22, 2015; 62/291,571, filed on Feb. 5, 2016; 62/311,455, filed on Mar. 22, 2016; and 62/367,374, filed on Jul. 27, 2016. The disclosures of the aforementioned patent applications are herein incorporated by reference in their entireties.

FIELD OF THE INVENTION

The present invention relates to the field of therapeutic treatments of diseases and disorders which are associated with elevated levels of lipids and lipoproteins. More specifically, the invention relates to the use of PCSK9 inhibitors to treat patients with hyperlipidemia and related conditions who are currently being treated with a therapeutic regimen comprising lipoprotein apheresis (e.g., LDL apheresis or Lp(a) apheresis).

BACKGROUND

Hyperlipidemia is a general term that encompasses diseases and disorders characterized by or associated with elevated levels of lipids and/or lipoproteins in the blood. Hyperlipidemias include hypercholesterolemia, hypertriglyceridemia, combined hyperlipidemia, and elevated lipoprotein a (Lp(a)). A particular prevalent form of hyperlipidemia in many populations is hypercholesterolemia.

Hypercholesterolemia, particularly an increase in low-density lipoprotein (LDL) cholesterol (LDL-C) levels, constitutes a major risk for the development of atherosclerosis and coronary heart disease (CHD) (Sharrett et al., 2001, Circulation 104:1108-1113). Low-density lipoprotein cholesterol is identified as the primary target of cholesterol lowering therapy and is accepted as a valid surrogate therapeutic endpoint. Numerous studies have demonstrated that reducing LDL-C levels reduces the risk of CHD with a strong direct relationship between LDL-C levels and CHD events; for each 1 mmol/L (~40 mg/dL) reduction in LDL-C, cardiovascular disease (CVD) mortality and morbidity is lowered by 22%. Greater reductions in LDL-C produce greater reduction in events, and comparative data of intensive versus standard statin treatment suggest that the lower the LDL-C level, the greater the benefit in patients at very high cardiovascular (CV) risk.

Familial hypercholesterolemia (FH) is an inherited disorder of lipid metabolism that predisposes a person to premature severe cardiovascular disease (CVD). Defects in at least 3 different genes that code for proteins involved in hepatic clearance of low-density lipoprotein (LDL) cholesterol (LDL-C) can cause FH. Examples of such defects include mutations in the gene coding for the LDL receptor (LDLR) that removes LDL-C from the circulation, and in the gene for apolipoprotein (Apo) B, which is the major protein of the LDL particle. In certain cases of FH, the gene coding for proprotein convertase subtilisin/kexin type 9 (PCSK9), an enzyme involved in degrading the LDLR (gain of function mutation), is mutated. In all cases, FH is characterized by an accumulation of LDL-C in the plasma from birth and subsequent development of tendon xanthomas, xanthelasmas, atheromata, and CVD. FH can be classified as either heterozygous FH (heFH) or homozygous FH (hoFH) depending on whether the individual has a genetic defect in one (heterozygous) or both (homozygous) copies of the implicated gene.

Current LDL-C-lowering medications include statins, cholesterol absorption inhibitors, fibrates, niacin, and bile acid sequestrants. Statins are a commonly prescribed treatment for LDL-C lowering. However, despite the availability of such lipid-lowering therapies, many high-risk patients fail to reach their guideline target LDL-C level (Gitt et al., 2010, Clin Res Cardiol 99(11):723-733). For patients who are still unable to achieve guideline target level for LDL-C, despite available lipid-modifying therapy (LMT), mechanical removal of LDL-C by lipoprotein apheresis (e.g., LDL apheresis) is sometimes prescribed. Lipoprotein apheresis removes apoproteinB100-containing lipoproteins from the blood. It is generally regarded as a last-resort option for patients with progressive cardiovascular disease and persistently elevated LDL-C.

However, LDL apheresis is a costly procedure that is invasive and burdensome for patients. Apheresis, in general, involves the mechanical removal blood from a patient; the blood is subjected to centrifugation, filtration or other separation steps outside the body to remove unwanted constituents and then reintroduced back into the patient. Lipoprotein apheresis acutely lowers the LDL-C concentration by 50-75%, which translates to a time-averaged LDL-C reduction of approximately 30% between apheresis procedures. Typical apheresis processes are characterized by a transient reduction in serum lipoprotein concentration that is followed over time by an almost linear return of lipoprotein levels to the elevated "baseline" level. This oscillating pattern of lipoprotein levels, which is characteristic of lipoprotein apheresis therapies, explains the need for periodic apheresis treatments that are required throughout the lifetime of an individual. Furthermore, because of the sparsity of apheresis centers in many geographical locations, many patients must travel a significant distance for this procedure, which is administered over 3 hours and is typically given every week to every 4 weeks, depending on the patient's LDL-C level and cardiovascular risk. In addition, this procedure may require placement of a shunt for frequent vascular access. Low-density lipoprotein apheresis is generally well tolerated, but may result in hypotension, hypocalcemia, allergic reactions, and an acute decrease in serum protein levels. It has been documented that quality of life (QoL, as determined by questionnaire) was lower in patients undergoing apheresis in addition to lipid-lowering drugs compared to patients treated only with lipid-lowering drugs (Schiel et al., 1995, Int J Artif Organs 18:786-793). Thus, patients who are not at LDL-C goal despite receiving an optimized LMT regimen, and who require apheresis to lower LDL-C, would greatly benefit from alternative LDL-C lowering therapies that are capable of reducing or eliminating the need for apheresis.

BRIEF SUMMARY OF THE INVENTION

The present invention provides methods for treating hyperlipidemia in patients receiving lipoprotein apheresis therapy. The therapeutic methods of the present invention result in a lowering of serum lipoprotein levels and thereby serve to eliminate or reduce a patient's need for lipoprotein apheresis. In certain embodiments, the frequency of apheresis treatments required by a patient to achieve a target lipoprotein level (e.g., a target LDL-C level) is reduced by application of the therapeutic methods of the present invention. In certain embodiments, a patient's need for apheresis to achieve a target lipoprotein level (e.g., a target LDL-C level) is eliminated by application of the therapeutic methods of the present invention.

According to one aspect, the methods of the present invention comprise administering one or more doses of a PCSK9 inhibitor to a patient who is being or has been treated (e.g., within the last six months) with lipoprotein apheresis, wherein administration of the PCSK9 inhibitor to the patient results in a lowering of the level of at least one lipoprotein in the serum of the patient and consequently reduces or eliminates the need for lipoprotein apheresis therapy by the patient.

According to another aspect, the methods of the present invention comprise selecting a patient with hypercholesterolemia who is being or has been treated with lipoprotein apheresis at an initial (pre-treatment) frequency, and administering one or more doses of a PCSK9 inhibitor to the patient, thereby lowering the level of at least one lipoprotein in the serum of the patient and consequently reducing frequency of lipoprotein apheresis required by the patient to achieve a target lipoprotein level.

Patients who are treated or treatable by the methods of the present invention include, e.g., patients with hypercholesterolemia, including patients with familial hypercholesterolemia (FH). In certain embodiments, the patients who are treated or treatable by the methods of the present invention are patients who are diagnosed with (or otherwise known to have) homozygous FH (hoFH) or heterozygous FH (heFH).

According to certain embodiments of the present invention, the PCSK9 inhibitor is administered to the patient as an add-on therapy to the patient's existing lipid-lowering therapy (e.g., on top of the patient's background statin therapy).

The present invention also provides pharmaceutical compositions comprising a PCSK9 inhibitor for use in reducing or eliminating the need for lipoprotein apheresis therapy, or for use in reducing the frequency of lipoprotein apheresis therapy by a patient.

Exemplary PCSK9 inhibitors that may be used in the context of the methods of the present invention include, e.g., anti-PCSK9 antibodies, small molecule PCSK9 inhibitors, and scaffold-based PCSK9-binding molecules.

Other embodiments of the present invention will become apparent from a review of the ensuing detailed description.

DETAILED DESCRIPTION

Figure 1:
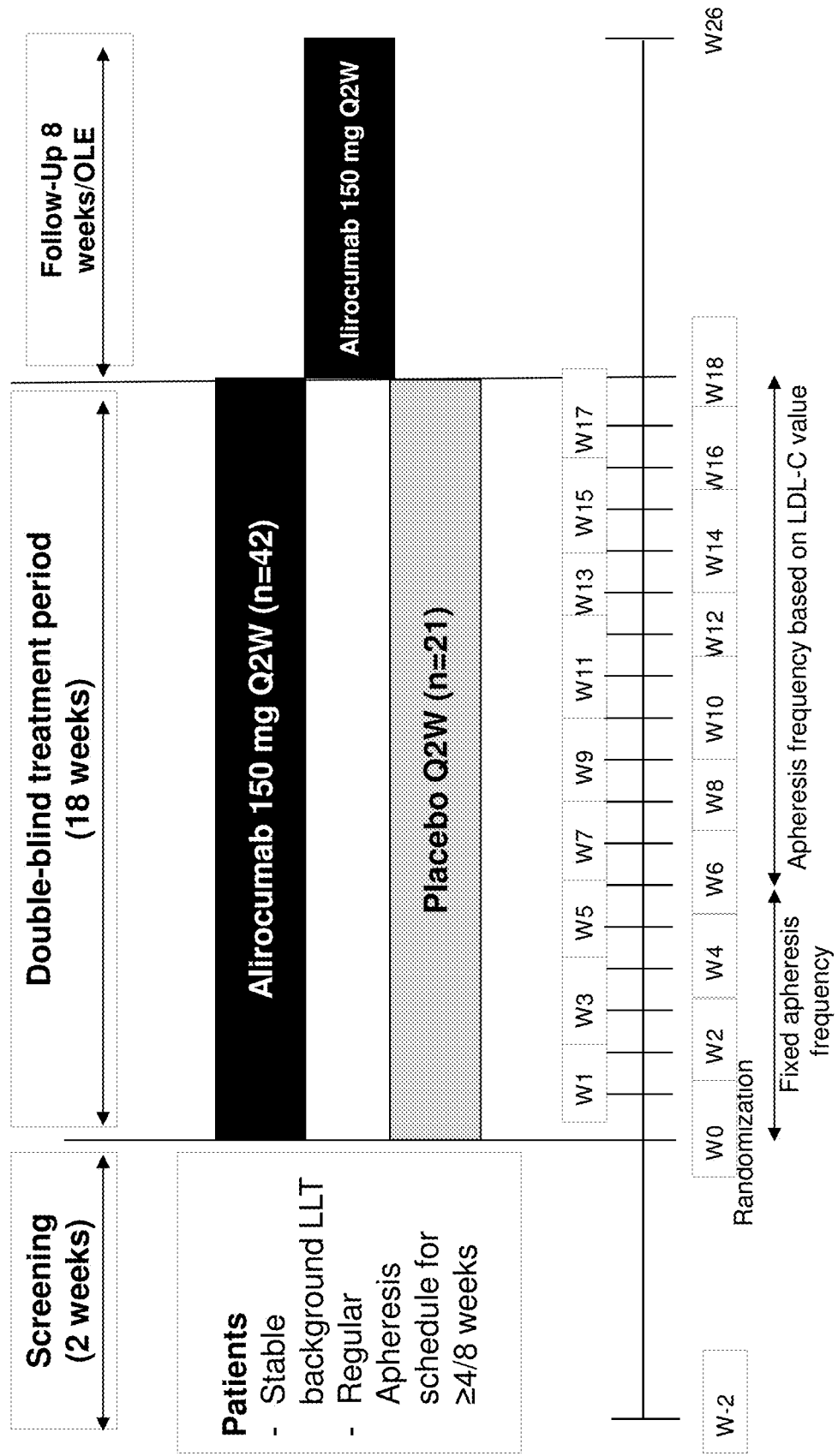
FIG. 1 is a diagram illustrating the overall design of the study described in Example 2 herein. The study included a 2 week screening period, an 18 week double-blind treatment period, and an optional 8 week follow-up/open-label extension period.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Reducing or Eliminating the Need for Lipoprotein Apheresis

The present invention relates generally to methods and compositions for reducing lipoprotein levels in patients who are undergoing or have undergone (e.g., within the last six months or more) lipoprotein apheresis to lower serum lipoprotein levels (e.g., LDL-C and/or Lp(a)). According to certain embodiments, the methods of the present invention result in a reduction in lipoprotein levels in the serum of such patients so that the need for lipoprotein apheresis is reduced or eliminated.

As used herein, the term "lipoprotein" means a biomolecular particle containing both protein and lipid. Examples of lipoproteins include, e.g., low density lipoprotein (LDL), very low density lipoprotein (VLDL), intermediate density lipoprotein (IDL), and lipoprotein (a) (Lp(a)).

As used in the context of the present invention, "lipoprotein apheresis" means a therapeutic process involving the mechanical removal blood from a patient, followed by the removal of lipoprotein (e.g., LDL-C and/or Lp(a)) from the patient's blood by processes such as filtration, adsorption, precipitation, and the like, and finally reintroduction of the treated blood back into the patient's blood stream. For purposes of the present disclosure, "LDL apheresis" and "Lp(a) apheresis" are considered types of apheresis, and therefore are encompassed by the definition of the more general definition "lipoprotein apheresis."

Specific types of lipoprotein apheresis that are included in the context of the present invention include, e.g., double membrane filtration, immunoadsorption, heparin-induced LDL precipitation, direct adsorption of lipids, dextran sulfate-cellulose adsorption (plasma or whole blood), heparin extracorporeal LDL precipitation (HELP) system, DFPP and thermofiltration plasmapheresis, and hemoperfusion.

The present invention, according to certain embodiments, includes methods for eliminating the need for lipoprotein apheresis therapy. As used herein, a particular patient's "need for lipoprotein apheresis therapy" is determined by a physician, physician's assistant, diagnostician, or other medical professional on the basis of the level of one or more lipoproteins (e.g., LDL-C and/or Lp(a)) measured or otherwise detected in the serum of the patient. A patient's "need for lipoprotein apheresis therapy" may also be determined or influenced by other factors such as the patient's family history, medical background, current therapeutic treatment status, as well as generally accepted or prevailing lipoprotein targets adopted by national medical associations and physicians' groups. For example, in certain contexts, an LDL-C level of greater than or equal to about 70 mg/dL indicates a "need for lipoprotein apheresis therapy" by a patient. In other contexts, an LDL-C level of greater than or equal to about 100 mg/dL indicates a "need for lipoprotein apheresis therapy" by a patient. In certain contexts, an LDL-C level greater than or equal to about 150 mg/dL, 200 mg/dL, 250 mg/dL, 300 mg/dL, 400 mg/dL or higher, indicates a "need for lipoprotein apheresis therapy" by a patient. In yet other contexts, whether or not a particular percentage reduction in LDL-C or Lp(a) level is met, relative to the patient's LDL-C or Lp(a) level at a particular start point ("baseline") can be used to determine whether the patient has a "need for lipoprotein apheresis therapy." For instance, a reduction in LDL-C or Lp(a) of less than 50% (e.g., less than 40%, less than 35%, less than 30%, less than 25%, etc.) from baseline may signify a "need for lipoprotein apheresis therapy."

The present invention, according to certain embodiments, includes methods for reducing the frequency of lipoprotein apheresis therapy in a patient. As will be appreciated by persons of ordinary skill in the art, a patient may be treated with lipoprotein apheresis at a particular frequency in order to achieve a particular lipoprotein goal (e.g., an LDL-C level of less than 100 mg/dL, an LDL-C level of less than 70 mg/dL, etc.). The prescribed frequency is determined based on the number of apheresis treatments required by a patient during a particular time period (e.g., weekly, monthly, etc.) in order to achieve and maintain the lipoprotein goal for the patient. Exemplary lipoprotein apheresis frequencies include, e.g., once a week, once every two weeks, once every 3 weeks, once every four weeks, once every five weeks, once a month, twice a month, once every two months, etc. The present invention includes methods for reducing the frequency of lipoprotein apheresis therapy in a patient by administering to the patient one or more doses of a PCSK9 inhibitor. According to certain embodiments of the present invention, the frequency of apheresis following administration of one or more doses of a PCSK9 inhibitor is reduced by at least 50% from the patient's pre-treatment apheresis frequency. For example, if a patient, prior to treatment with a PCSK9 inhibitor, is on a lipoprotein apheresis treatment regimen at a frequency of once a week (QW), and after treatment with a PCSK9 inhibitor the apheresis frequency for the patient is reduced to once every 2 weeks (Q2W), then the patient is said to have achieved a 50% reduction in lipoprotein apheresis frequency following treatment. In certain embodiments, the frequency of apheresis following administration of one or more doses of a PCSK9 inhibitor according to the present invention, is reduced by 75%, or by 100% (i.e., elimination of the need for lipoprotein apheresis following treatment).

Lipoprotein apheresis frequency, in the context of the present invention, can be expressed in terms of a pre-treatment frequency and a post-treatment frequency. "Pre-treatment frequency" means the frequency of apheresis therapy required by a patient in order to achieve and/or maintain a particular target lipoprotein level prior to commencement of a therapeutic regimen comprising administration of a PCSK9 inhibitor. "Post-treatment frequency" means the frequency of apheresis therapy required by a patient in order to achieve and/or maintain a particular target lipoprotein level after to commencement of a therapeutic regimen comprising administration of a PCSK9 inhibitor. The frequency of apheresis therapy required to achieve and/or maintain a particular target lipoprotein level for a particular patient is preferably determined by a qualified medical professional based on generally accepted criteria in the art, including the serum level of lipoprotein sought to be reduced or otherwise controlled.

The present invention, accordingly, includes methods of treatment comprising administration of one or more doses of a PCSK9 inhibitor to a patient, whereby the patient's post-treatment frequency of lipoprotein apheresis is less than the patient's pre-treatment frequency of lipoprotein apheresis. For example, the present invention includes therapeutic methods comprising administering one or more doses of a PCSK9 inhibitor to a patient who is undergoing or has undergone lipoprotein apheresis therapy at a pre-treatment frequency of, e.g., once a week, wherein, after receiving one or more doses of the PCSK9 inhibitor, the frequency of lipoprotein apheresis required by the patient to achieve and/or maintain a particular target lipoprotein level (i.e., post-treatment frequency) is, e.g., once every two weeks, once every three weeks, once every four weeks, or less frequently. In some instances, the need for lipoprotein apheresis required by the patient to achieve and/or maintain a particular target lipoprotein level is eliminated altogether following administration of one or more doses of the PCSK9 inhibitor.

According to certain embodiments, the present invention comprises methods for reducing or eliminating the need for lipoprotein apheresis therapy, wherein the methods comprise selecting a patient with hyperlipidemia (e.g., hypercholesterolemia) who has been treated with lipoprotein apheresis within the last month, the last 2 months, the last 3 months, the last 4 months, the last 5 months, the last 6 months, or for a longer period, and administering one or more doses of a PCSK9 inhibitor to the patient. The methods according to this aspect of the invention result in lowering the level of at least one lipoprotein in the serum of the patient, and consequently allow for a reduction or elimination of the need for lipoprotein apheresis therapy by the patient. For example, in certain embodiments of the present invention, following administration of one or more doses of a PCSK9 inhibitor, the serum LDL-C level of the patient is reduced to less than a defined level (e.g., less than 100 mg/dL or less than 70 mg/dL), such that the post-treatment frequency of lipoprotein apheresis therapy required by the patient to achieve and/or maintain a particular target lipoprotein level is reduced, or it is concluded that lipoprotein apheresis is no longer required.

In certain embodiments, rate (or frequency) of apheresis is expressed as the normalized rate of apheresis required by a patient to achieve and/or maintain a particular target lipoprotein level. As used herein, the normalized rate of apheresis for a particular patient is defined as the number of actual apheresis treatments received by the patient over defined period of time following initiation of an anti-PCSK9 therapeutic regimen, divided by the number of apheresis treatments received by the patient over an equivalent period of time prior to initiation of the anti-PCSK9 therapeutic regimen. For example, if prior to initiating a therapeutic regiment comprising administration of an anti-PCSK9 antibody, a patient received 8 apheresis treatments over an 8 week period (e.g., once a week), and after initiation of the anti-PCSK9 therapeutic regiment the patient received 2 apheresis treatments over an 8 week period (e.g., once every four weeks), then the patient's normalized rate of apheresis is $2/8=0.25$. The present invention includes methods by which the normalized rate of apheresis for a patient following administration of a PCSK9 inhibitor is, e.g., less than 0.9, less than 0.8, less than 0.7, less than 0.6, less than 0.5, less than 0.4, less than 0.3, less than 0.2, or less than 0.1.

According to certain embodiments, the patient who is treatable by the methods of the present invention has hypercholesterolemia (e.g., a serum LDL-C concentration of greater than or equal to 70 mg/dL, or a serum LDL-C concentration greater than or equal to 100 mg/dL). In certain embodiments, the patient's hypercholesterolemia is inadequately controlled by statin therapy. For example, the present invention includes methods for reducing or eliminating the frequency of lipoprotein apheresis therapy by a patient who has hypercholesterolemia that is inadequately controlled by a daily dose of a statin selected from the group consisting of atorvastatin (including atorvastatin+ezetimibe), rosuvastatin, cerivastatin, pitavastatin, fluvastatin, lovastatin, simvastatin (including simvastatin+ezetimibe), pravastatin, and combinations thereof. The present invention also includes methods for reducing or eliminating the frequency of lipoprotein apheresis therapy by a patient who has hypercholesterolemia and who exhibits statin intolerance or who otherwise experiences adverse or undesirable reaction(s) to statin therapy (e.g., skeletal muscle pain, aches, weakness or cramping [e.g., myalgia, myopathy, rhabdomyolysis, etc.]).

Methods for Treating Lipid Lesions

The present invention further relates to methods and compositions for treating, reversing or resolving physical manifestations of hypercholesterolemia. According to certain embodiments, the present invention provides methods for treating a patient having a lipid lesion associated with hypercholesterolemia. For example, the present invention provides method for treating a patient having one or more xanthelasmata. The methods and compositions according to this aspect of the invention comprise administering one or more doses of PCSK9 inhibitor to a patient in need thereof, wherein lipid lesions that were existent in the patient prior to treatment with a PCSK9 inhibitor are reduced, resolved or eliminated following administration of one or more doses of the PCSK9 inhibitor to the patient. According to certain embodiments, the present invention comprises methods for treating a patient having a lipid lesion associated with hypercholesterolemia, wherein the methods comprise selecting a patient with a lipid lesion (e.g., a xanthelasma), and administering one or more doses of a PCSK9 inhibitor to the patient.

Patient Selection

The present invention includes methods and composition useful for treating patients who are undergoing, or have recently undergone, lipoprotein apheresis (e.g., within the last six months, within the last 12 weeks, within the last 8 weeks, within the last 6 weeks, within the last 4 weeks, within the last 2 weeks, etc.). The patients who are treatable by the methods of the present invention may also exhibit one or more of additional selection criteria. For example, a patient may be selected for treatment with the methods of the present invention if the patient is diagnosed with or identified as being at risk of developing a hypercholesterolemia condition such as, e.g., heterozygous Familial Hypercholesterolemia (heFH), homozygous Familial Hypercholesterolemia (hoFH), Autosomal Dominant Hypercholesterolemia (ADH, e.g., ADH associated with one or more gain-of-function mutations in the PCSK9 gene), autosomal recessive hypercholesterolemia (ARH, e.g., ARH associated with mutations in LDLRAP1), as well as incidences of hypercholesterolemia that are distinct from Familial Hypercholesterolemia (nonFH). Diagnosis of familial hypercholesterolemia (e.g., heFH or hoFH) can be made by genotyping and/or clinical criteria. For patients who are not genotyped, clinical diagnosis may be based on either the Simon Broome criteria with a criteria for definite FH, or the WHO/Dutch Lipid Network criteria with a score >8 points.

According to certain embodiments, the patient may be selected on the basis of having a history of coronary heart disease (CHD). As used herein a "history of CHD" (or "documented history of CHD") includes one or more of: (i) acute myocardial infarction (MI); (ii) silent MI; (iii) unstable angina; (iv) coronary revascularization procedure (e.g., percutaneous coronary intervention [PCI] or coronary artery bypass graft surgery [CABG]); and/or (v) clinically significant CHD diagnosed by invasive or non-invasive testing (such as coronary angiography, stress test using treadmill, stress echocardiography or nuclear imaging).

According to certain embodiments, the patient may be selected on the basis of having non-coronary heart disease cardiovascular disease ("non-CHD CVD"). As used herein, "non-CHD CVD" includes one or more of: (i) documented previous ischemic stroke with a focal ischemic neurological deficit that persisted more than 24 hours, considered as being of atherothrombotic origin; (ii) peripheral arterial disease; (iii) abdominal aortic aneurysm; (iv) atherosclerotic renal artery stenosis; and/or (v) carotid artery disease (transient ischemic attacks or >50% obstruction of a carotid artery).

According to certain embodiments, the patient may be selected on the basis of having one or more additional risk factors such as, e.g., (i) documented moderate chronic kidney disease ($CK_D$) as defined by 30≤eGFR <60 mL/min/1.73 m2 for 3 months or more; (ii) type 1 or type 2 diabetes mellitus with or without target organ damage (e.g., retinopathy, nephropathy, microalbuminuria); (iii) a calculated 10-year fatal CVD risk SCORE ≥5% (ESC/EAS Guidelines for the management of dyslipidemias, Conroy et al., 2003, Eur. Heart J. 24:987-1003).

According to certain embodiments, the patient may be selected on the basis of having one or more additional risk factors selected from the group consisting of age (e.g., older than 40, 45, 50, 55, 60, 65, 70, 75, or 80 years), race, national origin, gender (male or female), exercise habits (e.g., regular exerciser, non-exerciser), other preexisting medical conditions (e.g., type-II diabetes, high blood pressure, etc.), and current medication status (e.g., currently taking beta blockers, niacin, ezetimibe, fibrates, omega-3 fatty acids, bile acid resins, etc.).

According to the present invention, patients may be selected on the basis of a combination of one or more of the foregoing selection criteria or therapeutic characteristics. For example, according to certain embodiments, a patient suitable for treatment with the methods of the present invention, in addition to undergoing, or have recently undergone (e.g., within the last six months), lipoprotein apheresis, may further be selected on the basis of having heFH or non-FH in combination with: (i) a history of documented CHD, (ii) non-CHD CVD, and/or (iii) diabetes mellitus with target organ damage; such patients may also be selected on the basis of having a serum LDL-C concentration of greater than or equal to 70 mg/dL.

According to certain other embodiments, a patient suitable for treatment with the methods of the present invention, in addition to having hypercholesterolemia that is not adequately controlled by a daily moderate-dose therapeutic statin regimen, may further be selected on the basis of having heFH or non-FH without CHD, or non-CHD CVD, but having either (i) a calculated 10-year fatal CVD risk SCORE ≥5%; or (ii) diabetes mellitus without target organ damage; such patients may also be selected on the basis of having a serum LDL-C concentration of greater than or equal to 100 mg/dL.

Administration of a PCSK9 Inhibitor as Add-On Therapy

The present invention includes methods of treatment wherein a patient who is undergoing, or has recently undergone, lipoprotein apheresis is administered a PCSK9 inhibitor according to a particular dosing amount and frequency, and wherein the PCSK9 inhibitor is administered as an add-on to the patient's pre-existing lipid lowering therapy (if applicable), such as an add-on to the patient's pre-existing daily therapeutic statin regimen.

For example, the methods of the present invention include add-on therapeutic regimens wherein the PCSK9 inhibitor is administered as add-on therapy to the same stable daily therapeutic statin regimen (i.e., same dosing amount of statin) that the patient was on prior to receiving the PCSK9 inhibitor. In other embodiments, the PCSK9 inhibitor is administered as add-on therapy to a therapeutic statin regimen comprising a statin in an amount that is more than or less than the dose of stain the patient was on prior to receiving the PCSK9 inhibitor. For example, after starting a therapeutic regimen comprising a PCSK9 inhibitor administered at a particular dosing frequency and amount, the daily dose of statin administered or prescribed to the patient may (a) stay the same, (b) increase, or (c) decrease (e.g., up-titrate or down-titrate) in comparison to the daily statin dose the patient was taking before starting the PCSK9 inhibitor therapeutic regimen, depending on the therapeutic needs of the patient.

Therapeutic Efficacy

The methods of the present invention result in the reduction in serum levels of one or more lipid component selected from the group consisting of LDL-C, ApoB100, non-HDL-C, total cholesterol, VLDL-C, triglycerides, Lp(a) and remnant cholesterol. The lipoprotein-lowering effects of the therapeutic regimens of the present invention consequently lead to a reduced frequency, or eliminated need for, lipoprotein apheresis in order to achieve a target lipoprotein level by the patient. For example, according to certain embodiments of the present invention, administration of a pharmaceutical composition comprising a PCSK9 inhibitor to a patient who is undergoing, or has recently undergone, lipoprotein apheresis will result in a mean percent reduction from baseline in serum low density lipoprotein cholesterol (LDL-C) of at least about 25%, 30%, 40%, 50%, 60%, or greater; a mean percent reduction from baseline in ApoB100 of at least about 25%, 30%, 40%, 50%, 60%, or greater; a mean percent reduction from baseline in non-HDL-C of at least about 25%, 30%, 40%, 50%, 60%, or greater; a mean percent reduction from baseline in total cholesterol of at least about 10%, 15%, 20%, 25%, 30%, 35%, or greater; a mean percent reduction from baseline in VLDL-C of at least about 5%, 10%, 15%, 20%, 25%, 30%, or greater; a mean percent reduction from baseline in triglycerides of at least about 5%, 10%, 15%, 20%, 25%, 30%, 35% or greater; and/or a mean percent reduction from baseline in Lp(a) of at least about 5%, 10%, 15%, 20%, 25%, or greater.

The present invention includes methods for treating a patient with hypercholesterolemia, the methods comprising administering multiple doses of an anti-PCSK9 antibody to the patient at a dosing amount of about 75 to 150 mg per dose, and a dosing frequency of about once every two weeks, (or a dosing regimen in accordance with an up-titration dosing regimen as described elsewhere herein), wherein the patient is undergoing, or has recently undergone, lipoprotein apheresis, and wherein, after about 12, 14, 16, 18, 20, 22, 24 or more weeks of treatment with the anti-PCSK9 antibody, the patient exhibits a reduction in LDL-C level from baseline of at least 50%, and therefore results in a reduced frequency or elimination of the need for lipoprotein apheresis by the patient. In certain embodiments, following one or more weeks of treatment with the anti-PCSK9 antibody, the patient exhibits a reduction in LDL-C level from baseline of about 55%, 60%, 70%, or more.

PCSK9 Inhibitors

The methods of the present invention comprise administering to a patient a therapeutic composition comprising a PCSK9 inhibitor. As used herein, a "PCSK9 inhibitor" is any agent which binds to or interacts with human PCSK9 and inhibits the normal biological function of PCSK9 in vitro or in vivo. Non-limiting examples of categories of PCSK9 inhibitors include small molecule PCSK9 antagonists, nucleic acid-based inhibitors of PCSK9 expression or activity (e.g., siRNA or antisense), peptide-based molecules that specifically interact with PCSK9 (e.g., peptibodies), receptor molecules that specifically interact with PCSK9, proteins comprising a ligand-binding portion of an LDL receptor, PCSK9-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, etc., [see, e.g., Boersma and Pluckthun, 2011, *Curr. Opin. Biotechnol.* 22:849-857, and references cited therein]), and anti-PCSK9 aptamers or portions thereof. According to certain embodiments, PCSK9 inhibitors that can be used in the context of the present invention are anti-PCSK9 antibodies or antigen-binding fragments of antibodies that specifically bind human PCSK9.

The term "human proprotein convertase subtilisin/kexin type 9" or "human PCSK9" or "hPCSK9", as used herein, refers to PCSK9 having the nucleic acid sequence shown in SEQ ID NO:197 and the amino acid sequence of SEQ ID NO:198, or a biologically active fragment thereof.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PCSK9, as used in the context of the present invention, includes antibodies that bind PCSK9 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PCSK9, however, have cross-reactivity to other antigens, such as PCSK9 molecules from other (non-human) species.

The anti-PCSK9 antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-PCSK9 antibodies comprising variants of any of the HCVR, LCVR, and/or CDR amino acid sequences disclosed herein having one or more conservative substitutions. For example, the present invention includes the use of anti-PCSK9 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain embodiments, the anti-PCSK9 antibody used in the methods of the present invention is an antibody with pH-dependent binding characteristics. As used herein, the expression "pH-dependent binding" means that the antibody or antigen-binding fragment thereof exhibits "reduced binding to PCSK9 at acidic pH as compared to neutral pH" (for purposes of the present disclosure, both expressions may be used interchangeably). For the example, antibodies "with pH-dependent binding characteristics" includes antibodies and antigen-binding fragments thereof that bind PCSK9 with higher affinity at neutral pH than at acidic pH. In certain embodiments, the antibodies and antigen-binding fragments of the present invention bind PCSK9 with at least 3, 5, 10, 15, 20, 25, 30, 35, 40, 45, 50, 55, 60, 65, 70, 75, 80, 85, 90, 95, 100, or more times higher affinity at neutral pH than at acidic pH.

According to this aspect of the invention, the anti-PCSK9 antibodies with pH-dependent binding characteristics may possess one or more amino acid variations relative to the parental anti-PCSK9 antibody. For example, an anti-PCSK9 antibody with pH-dependent binding characteristics may contain one or more histidine substitutions or insertions, e.g., in one or more CDRs of a parental anti-PCSK9 antibody. Thus, according to certain embodiments of the present invention, methods are provided comprising administering an anti-PCSK9 antibody which comprises CDR amino acid sequences (e.g., heavy and light chain CDRs) which are identical to the CDR amino acid sequences of a parental anti-PCSK9 antibody, except for the substitution of one or more amino acids of one or more CDRs of the parental antibody with a histidine residue. The anti-PCSK9 antibodies with pH-dependent binding may possess, e.g., 1, 2, 3, 4, 5, 6, 7, 8, 9, or more histidine substitutions, either within a single CDR of a parental antibody or distributed throughout multiple (e.g., 2, 3, 4, 5, or 6) CDRs of a parental anti-PCSK9 antibody. For example, the present invention includes the use of anti-PCSK9 antibodies with pH-dependent binding comprising one or more histidine substitutions in HCDR1, one or more histidine substitutions in HCDR2, one or more histidine substitutions in HCDR3, one or more histidine substitutions in LCDR1, one or more histidine substitutions in LCDR2, and/or one or more histidine substitutions in LCDR3, of a parental anti-PCSK9 antibody.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.90, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Non-limiting examples of anti-PCSK9 antibodies that can be used in the context of the present invention include, e.g., alirocumab, evolocumab, bococizumab, lodelcizumab, ralpancizumab, or antigen-binding portions of any of the foregoing antibodies.

Preparation of Human Antibodies

Methods for generating human antibodies in transgenic mice are known in the art. Any such known methods can be used in the context of the present invention to make human antibodies that specifically bind to human PCSK9.

Using VELOCIMMUNE™ technology (see, for example, U.S. Pat. No. 6,596,541, Regeneron Pharmaceuticals) or any other known method for generating monoclonal antibodies, high affinity chimeric antibodies to PCSK9 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs:1 and 11, or a substantially similar sequence thereof having at least 90%, at least 95%, at least 98% or at least 99% sequence identity. Alternatively, specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs 37, 45, 53, 61, 69, 77, 85, 93, 101, 109, 117, 125, 133, 141, 149, 157, 165, 173, 181, and 189, or a substantially similar sequence thereof having at least 90%, at least 95%, at least 98% or at least 99% sequence identity. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs 6 and 15, or a substantially similar sequence thereof having at least 90%, at least 95%, at least 98% or at least 99% sequence identity. Alternatively, the antibody or antigen-binding fragment may comprise the three light chain CDRs (LCVR1, LCVR2, LCVR3) contained within a light chain variable region (LCVR) having an amino acid sequence selected from the group consisting of SEQ ID NOs 41, 49, 57, 65, 73, 81, 89, 97, 105, 113, 121, 129, 137, 145, 153, 161, 169, 177, 185, and 193, or a substantially similar sequence thereof having at least 90%, at least 95%, at least 98% or at least 99% sequence identity.

Sequence identity between two amino acids sequences is determined over the entire length of the reference amino acid sequence, i.e. the amino acid sequence identified with a SEQ ID NO, using the best sequence alignment and/or over the region of the best sequence alignment between the two amino acid sequences, wherein the best sequence alignment can be obtained with art known tools, e.g. Align, using standard settings, preferably EMBOSS::needle, Matrix:Blosum62, Gap Open 10.0, Gap Extend 0.5.

In certain embodiments of the present invention, the antibody or antigen-binding protein comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs:1/6 and 11/15. Alternatively, in certain embodiments of the present invention, the antibody or antigen-binding protein comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs:37/41, 45/49, 53/57, 61/65, 69/73, 77/81, 85/89, 93/97, 101/105, 109/113, 117/121, 125/129, 133/137, 141/145, 149/153, 157/161, 165/169, 173/177, 181/185, and 189/193.

In certain embodiments of the present invention, the anti-PCSK9 antibody, or antigen-binding protein, that can be used in the methods of the present invention has HCDR1/HCDR2/HCDR3/LCDR1/LCDR2/LCDR3 amino acid sequences selected from SEQ ID NOs: 2/3/4/7/8/10 (mAb316P [also referred to as "REGN727," or "alirocumab"]) and 12/13/14/16/17/18 (mAb300N) (See US Patent App. Publ No. 2010/0166768) and 12/13/14/16/17/18, wherein SEQ ID NO:16 comprises a substitution of histidine for leucine at amino acid residue 30 (L30H).

In certain embodiments of the present invention, the antibody or antigen-binding protein comprises HCVR/LCVR amino acid sequence pairs selected from the group consisting of SEQ ID NOs:1/6 and 11/15. In certain exemplary embodiments, the antibody or antigen-binding protein comprises an HCVR amino acid sequence of SEQ ID NO:1 and an LCVR amino acid sequence of SEQ ID NO:6. In certain exemplary embodiments, the antibody or antigen-binding protein comprises an HCVR amino acid sequence of SEQ ID NO:11 and an LCVR amino acid sequence of SEQ ID NO:15. In certain exemplary embodiments, the antibody or antigen-binding protein comprises an HCVR amino acid sequence of SEQ ID NO:11 and an LCVR amino acid sequence of SEQ ID NO:15 comprising a substitution of histidine for leucine at amino acid residue 30 (L30H).

Pharmaceutical Compositions and Methods of Administration

The present invention includes methods which comprise administering a PCSK9 inhibitor to a patient, wherein the PCSK9 inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Exemplary pharmaceutical formulations comprising anti-PCSK9 antibodies that can be used in the context of the present invention include any of the formulations as set forth in U.S. Pat. No. 8,795,669 (describing, inter alia, exemplary formulations comprising alirocumab), or in WO2013/166448, or WO2012/168491.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of PCSK9 inhibitor (e.g., anti-PCSK9 antibody) administered to a subject according to the methods of the present invention is, generally, a therapeutically effective amount. As used herein, the phrase "therapeutically effective amount" means a dose of PCSK9 inhibitor that results in a detectable reduction (at least about 5%, 10%, 15%, 20%, 25%, 30%, 35%, 40%, 45%, 50%, 55%, 60%, 65%, 70%, 75%, or more from baseline) in one or more parameters selected from the group consisting of LDL-C, ApoB100, non-HDL-C, total cholesterol, VLDL-C, triglycerides, Lp(a) and remnant cholesterol, or an amount that reduces or eliminates a patient's need for lipoprotein apheresis or that reduces a patient's normalized rate of apheresis (as defined elsewhere herein).

In the case of an anti-PCSK9 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PCSK9 antibody. According to certain exemplary embodiments of the present invention, a therapeutically effective amount of an anti-PCSK9 antibody is 75 mg, 150 mg or 300 mg (e.g., in the case of alirocumab), or 140 mg or 420 mg (e.g., in the case of evolocumab). Other dosing amounts of PCSK9 inhibitors will be apparent to persons of ordinary skill in the art and are contemplated within the scope of the present invention.

The amount of anti-PCSK9 antibody contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight.

Combination Therapies

As described elsewhere herein, the methods of the present invention may comprise administering a PCSK9 inhibitor to a patient in combination with ("on top of") the patient's previously prescribed lipid lowering therapy. For example, in the context of reducing or eliminating the need for lipoprotein apheresis, a PCSK9 inhibitor may be administered to a patient in combination with a stable daily therapeutic statin regimen. Exemplary daily therapeutic statin regimens that a PCSK9 inhibitor may be administered in combination with in the context of the present invention include, e.g., atorvastatin (10, 20, 40 or 80 mg daily), (atorvastatin/ezetimibe 10/10 or 40/10 mg daily), rosuvastatin (5, 10 or 20 mg daily), cerivastatin (0.4 or 0.8 mg daily), pitavastatin (1, 2 or 4 mg daily), fluvastatin (20, 40 or 80 mg daily), simvastatin (5, 10, 20, 40 or 80 mg daily), simvastatin/ezetimibe (10/10, 20/10, 40/10 or 80/10 mg daily), lovastatin (10, 20, 40 or 80 mg daily), pravastatin (10, 20, 40 or 80 mg daily), and combinations thereof. Other lipid lowering therapies that a PCSK9 inhibitor may be administered in combination with in the context of the present invention include, e.g., (1) an agent which inhibits cholesterol uptake and or bile acid re-absorption (e.g., ezetimibe); (2) an agent which increase lipoprotein catabolism (such as niacin); and/or (3) activators of the LXR transcription factor that plays a role in cholesterol elimination such as 22-hydroxycholesterol.

According to certain embodiments of the present invention, methods are provided comprising administering a PCSK9 inhibitor (e.g., an anti-PCSK9 antibody such as alirocumab, evolocumab, bococizumab, lodelcizumab, or ralpancizumab) to a patient in combination with an inhibitor of angiopoietin-like protein 3 (e.g., an anti-ANGPTL3 antibody such as REGN1500), an inhibitor of angiopoietin-like protein 4 (e.g., an anti-ANGPTL4 antibody such as the anti-ANGPTL4 antibody referred to in U.S. Pat. No. 9,120,851 as "H1H268P" or "H4H284P"), or an inhibitor of angiopoietin-like protein 8 (e.g., an anti-ANGPTL8 antibody).

In the context of the methods of the present invention, additional therapeutically active component(s), e.g., any of the agents listed above or derivatives thereof, may be administered just prior to, concurrent with, or shortly after the administration of a PCSK9 inhibitor; (for purposes of the present disclosure, such administration regimens are considered the administration of a PCSK9 inhibitor "in combination with" an additional therapeutically active component). The present invention includes pharmaceutical compositions and methods of use thereof in which a PCSK9 inhibitor is co-formulated with one or more of the additional therapeutically active component(s) as described elsewhere herein.

Administration Regimens

According to certain embodiments of the present invention, multiple doses of a PCSK9 inhibitor (i.e., a pharmaceutical composition comprising a PCSK9 inhibitor) may be administered to a subject over a defined time course (e.g., on top of a daily therapeutic statin regimen or other background lipid lowering therapy). The methods according to this aspect of the invention comprise sequentially administering to a subject multiple doses of a PCSK9 inhibitor. As used herein, "sequentially administering" means that each dose of PCSK9 inhibitor is administered to the subject at a different point in time, e.g., on different days separated by a predetermined interval (e.g., hours, days, weeks or months). The present invention includes methods which comprise sequentially administering to the patient a single initial dose of a PCSK9 inhibitor, followed by one or more secondary doses of the PCSK9 inhibitor, and optionally followed by one or more tertiary doses of the PCSK9 inhibitor.

The terms "initial dose," "secondary doses," and "tertiary doses," refer to the temporal sequence of administration of the individual doses of a pharmaceutical composition comprising a PCSK9 inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the PCSK9 inhibitor, but generally may differ from one another in terms of frequency of administration. In certain embodiments, however, the amount of PCSK9 inhibitor contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

According to exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of a PCSK9 inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2, 4, 6, 8 or more weeks after the immediately preceding dose. Similarly, in embodiments involving multiple tertiary doses, each tertiary dose may be administered at the same frequency as the other tertiary doses. For example, each tertiary dose may be administered to the patient 1 to 2, 4, 6, 8 or more weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens comprising an up-titration option (also referred to herein as "dose modification"). As used herein, an "up-titration option" means that, after receiving a particular number of doses of a PCSK9 inhibitor, if a patient has not achieved a specified reduction in one or more defined therapeutic parameters, the dose of the PCSK9 inhibitor is thereafter increased. For example, in the case of a therapeutic regimen comprising administration of 75 mg doses of an anti-PCSK9 antibody to a patient at a frequency of once every two weeks, if after 8 weeks (i.e., 5 doses administered at Week 0, Week 2 and Week 4, Week 6 and Week 8), the patient has not achieved a serum LDL-C concentration of less than 70 mg/dL, then the dose of anti-PCSK9 antibody is increased to e.g., 150 mg administered once every two weeks thereafter (e.g., starting at Week 10 or Week 12, or later).

In certain embodiments, the anti-PCSK9 antibody is administered to a subject at a dose of about 75 mg every two weeks, for example for at least three doses (or throughout the course of the treatment regimen spanning days, weeks, months, or years).

In certain embodiments, the anti-PCSK9 antibody is administered to a subject at a dose of about 150 mg every two weeks, for example for at least three doses (or throughout the course of the treatment regimen spanning days, weeks, months, or years).

In some embodiments, the antibody is administered to a subject at a dose of about 75 mg every two weeks for 12 weeks, and the dose remains at 75 mg every two weeks if, at week 8, the subject's LDL-C value was less than 100 mg/dl and a 30% reduction of LDL-C.

In other embodiments, the antibody is administered to a subject at a dose of about 75 mg every two weeks for 12 weeks, and the dose is titrated up to about 150 mg every two weeks if, at week 8, the subject's LDL-C value was greater than or equal to 100 mg/dl.

In some embodiments, the antibody is administered to a subject at a dose of about 75 mg every two weeks for 12 weeks, and the dose remains at 75 mg every two weeks if, at week 8, the subject's LDL-C value was less than 70 mg/dl and a 30% reduction of LDL-C.

In another embodiment, the antibody is administered to a subject at a dose of about 300 mg every four weeks.

In a further embodiment, the antibody is administered to a subject at a dose of about 300 mg every four weeks for a total of three doses, and the dose is changed to 150 mg every two weeks for another 36 weeks if, at week 8, the subject did not achieve a pre-determined treatment goal or the subject did not have at least a 30% reduction of LDL-C from baseline.

In certain embodiments, the anti-PCSK9 antibody is administered to a subject at a dose of about 150 mg every four weeks for at least three doses.

In some embodiments, the antibody is administered to a subject at a dose of about 150 mg every four weeks for 12 weeks, and the dose remains at 150 mg every four weeks if, at week 8, the subject's LDL-C value was less than 100 mg/dl and a 30% reduction of LDL-C.

In other embodiments, the antibody is administered to a subject at a dose of about 150 mg every four weeks for 12 weeks, and the dose is titrated up to about 300 mg every two weeks if, at week 8, the subject's LDL-C value was greater than or equal to 100 mg/dl.

In some embodiments, the antibody is administered to a subject at a dose of about 150 mg every four weeks for 12 weeks, and the dose remains at 150 mg every four weeks for another 12 weeks if, at week 8, the subject's LDL-C value was less than 70 mg/dl and a 30% reduction of LDL-C.

In another embodiment, the antibody is administered to a subject at a dose of about 300 mg every four weeks.

In a further embodiment, the antibody is administered to a subject at a dose of about 300 mg every four weeks for a total of three doses, and the dose is changed to 150 mg every two weeks for another 36 weeks if, at week 8, the subject did not achieve a pre-determined treatment goal or the subject did not have at least a 30% reduction of LDL-C from baseline.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human PCSK9

Human anti-PCSK9 antibodies were generated as described in U.S. Pat. No. 8,062,640. The exemplary PCSK9 inhibitor used in the following Example is the human anti-PCSK9 antibody designated "mAb316P," also known as "REGN727," or "alirocumab." mAb316P has the following amino acid sequence characteristics: a heavy chain comprising SEQ ID NO:5 and a light chain comprising SEQ ID NO:9; a heavy chain variable region (HCVR) comprising SEQ ID NO:1 and a light chain variable domain (LCVR) comprising SEQ ID NO:6; a heavy chain complementarity determining region 1 (HCDR1) comprising SEQ ID NO:2, a HCDR2 comprising SEQ ID NO:3, a HCDR3 comprising SEQ ID NO:4, a light chain complementarity determining region 1 (LCDR1) comprising SEQ ID NO:7, a LCDR2 comprising SEQ ID NO:8 and a LCDR3 comprising SEQ ID NO:10.

Example 2

A Randomized, Double-Blind, Placebo-Controlled, Parallel-Group Study to Evaluate the Efficacy and Safety of Alirocumab in Patients with Heterozygous Familial Hypercholesterolemia Undergoing Lipid Apheresis Therapy

INTRODUCTION

The objective of the present study was to evaluate the effect of alirocumab 150 mg administered once every two weeks ("Q2W") in comparison with placebo on the frequency of LDL apheresis treatments in patients with HeFH undergoing LDL apheresis therapy.

Adult men and women diagnosed with HeFH who were undergoing LDL apheresis therapy at a frequency of once every week or once every two weeks were enrolled in this study. The subjects' background treatment with LMT was maintained throughout the study. In such patients, the choice of placebo as a control is appropriate for the objectives of this study, since it provides the most robust assessment of efficacy and safety of alirocumab.

An average reduction of the LDL-C value ranges from 30% to 75% depending on the technique and duration of apheresis (Bambauer et al., Scientific World Journal, 2012, 2012:1-19). With weekly or bi-weekly treatment, the LDL-C levels can be reduced by 40% to 50%. According to the present study, apheresis was not performed when the LDL-C value at that visit was 30% lower than the baseline (pre-apheresis) LDL-C value. The LDL-C levels rise towards baseline after each apheresis procedure, but do not reach the original levels; with repeated weekly or bi-weekly apheresis, the baseline levels continue to fall until a plateau is reached (Thompsen et al., Atherosclerosis, 2006, 189:31-38). As such, a criterion to determine the necessity of apheresis, based on a 30% reduction in LDL-C levels, is justified since this reduction, if observed with administration of alirocumab, will be consistent over time, achieving approximately the same level of reduction in LDL-C as with the apheresis procedure.

Alirocumab Q2W (75 mg and 150 mg SC) and Q4W (150 mg and 300 mg SC) dosing regimens have been evaluated in other phase 3 trials of alirocumab. Based on the results of 2 dose finding studies, the Q2W dosing regimen was selected to maintain constant LDL-C lowering throughout the inter-dosing interval in all patients, with the maximum efficacy at 12 weeks provided by the 150 mg Q2W dosing. Heterozygous familial hypercholesterolemia patients generally have high baseline LDL-C levels. Considering that these patients have had life-long exposure to elevated LDL-C, their LDL-C target is either 100 mg/dL or 70 mg/dL, depending on their history of CVD or other risk factors. To reach and maintain their LDL-C target, it was surmised that such patients were very likely to require the most potent dose of alirocumab and at a frequency needed to maintain this effect at the end of the dosing interval. Therefore, the 150 mg Q2W dose was selected for this study.

In the double-blind treatment period of this study, 150 mg alirocumab Q2W administered for 18 weeks to patients with HeFH who require apheresis every 1 or 2 weeks to lower LDL-C, was evaluated for its ability to reduce the frequency of apheresis from week 7 to week 18 compared to the frequency during the 8 weeks before screening. Patients received 150 mg alirocumab Q2W through week 76 in the open-label treatment period.

Preliminary pharmacokinetic (PK) data from phase 2 studies, DFI11565, DFI11566, and R727-CL-1003, showed that exposure to alirocumab declined during the 8-week follow-up period that followed the double-blind treatment period, with total serum concentrations of alirocumab still detectable, but at very low levels. Therefore, to ensure sufficiently low, noneffective serum alirocumab concentrations, patients were followed during a follow-up period of 8 weeks (i.e., 10 weeks after the last dose).

Study Objectives

The primary objective of the study was to evaluate the effect of alirocumab 150 mg Q2W in comparison with placebo on the frequency of LDL apheresis treatments in patients with HeFH undergoing weekly or bi-weekly LDL apheresis therapy.

The secondary objectives of the study were: (a) To evaluate the effect of alirocumab 150 mg Q2W on LDL-C levels in patients with HeFH undergoing LDL apheresis therapy; (b) To evaluate the effect of alirocumab 150 mg Q2W on the following lipid parameters: ApoB, non-HDL-C, total cholesterol, Lp(a), HDL-C, TGs, and ApoA-1 in patients with HeFH undergoing LDL apheresis therapy during the study; (c) To evaluate the safety and tolerability of alirocumab 150 mg Q2W in patients with HeFH undergoing LDL apheresis therapy; (d) To assess the PK of alirocumab 150 mg Q2W in patients with HeFH undergoing LDL apheresis therapy (QW versus Q2W); (e) To evaluate the development of anti-alirocumab antibodies; (f) To evaluate PCSK9 levels in response to alirocumab therapy as well as pre and post-apheresis; and (g) To evaluate quality of life ("Q0L") in these patients.

Study Design

The present study was a randomized, double-blind, placebo-controlled, parallel-group study in patients with HeFH undergoing LDL apheresis therapy every 1 or 2 weeks.

The study consisted of 4 periods: screening, double-blind treatment period, open-label treatment period, and a follow-up. The double-blind treatment period comprised 2 intervals: day 1 to week 6 (with planned study drug administration on days 1, 15, and 29), when apheresis frequency will be fixed to the individual patient's established schedule, and week 7 to week 18 (with planned study drug administration on days 43, 57, 71, 85, 99, and 113), when apheresis frequency will be adjusted based on the patient's response to treatment.

Screening:

Patients who had been on a stable apheresis schedule (every 7 or 14 days), with stable apheresis settings for at least 4 weeks prior to the screening visit (week −2) and stable background medical LMT for at least 8 weeks prior to the screening visit (week −2), entered a 2-week screening period.

Double-Blind Treatment:

Patients who met all inclusion criteria and none of the exclusion criteria were randomly assigned in a 2:1 ratio to receive 18 weeks of treatment: Alirocumab 150 mg SC Q2W, or Placebo for alirocumab SC Q2W.

Treatment injections during the double-blind treatment period were administered Q2W starting on the day of randomization (week 0 [day 1]/visit 2). Patients were monitored at the clinical site for 30 minutes after the first dose. If LDL apheresis coincided with study drug administration, study drug was administered immediately after completion of the LDL apheresis procedure.

From day 1 to week 6, the apheresis frequency was fixed to the individual patient's established schedule (QW or Q2W). Starting at week 7, the LDL apheresis was administered based on the LDL-C value at that visit (determined by point-of-care testing). LDL apheresis was NOT administered when the LDL-C value at that visit was at least 30% lower than the pre-apheresis LDL-C value at baseline (day 1). The criterion to determine the necessity of apheresis, based on a 30% reduction in LDL-C levels, is justified since this reduction, if observed with administration of alirocumab, will be consistent over time, achieving approximately the same level of reduction in LDL-C as with the apheresis procedure. Investigators remained blinded to the point-of-care lab value for LDL-C and only received an alert as to whether or not LDL apheresis should be administered.

Open-Label Treatment:

In the open-label treatment period, patients received alirocumab 150 mg SC Q2W. Treatment continued uninterrupted from the last dose of study drug during the double-blind treatment period (last dose at week 16) to week 18 (the first dose in the open-label treatment period), through week 76.

The first injection during the open-label treatment period was administered at the week 18 visit (the first visit of the open-label treatment period) as part of patient injection training. Subsequent injections were administered by the patient or a designated caregiver (spouse, relative, etc.) at a patient-preferred location (e.g., home or place of work). Patients were also permitted to choose to return to the site Q2W to have the injection administered by study personnel.

Apheresis treatment was not required in the open-label treatment period of the study. At the investigator's discretion, patients were permitted to continue to undergo apheresis procedures, as needed. In the event that a planned apheresis procedure coincided with a clinic visit or alirocumab dosing day, study assessments were done before apheresis, and alirocumab was administered after apheresis.

Follow-Up:

Patients were seen at the end of study visit at week 86.

Throughout the Study:

All samples for clinical laboratory (lipid and specialty lipid panels) and PK evaluations were obtained immediately prior to and immediately after the LDL apheresis procedure (if LDL apheresis is administered at that visit) and before study drug administration.

For those patients not undergoing LDL apheresis at a visit, all samples for clinical laboratory evaluation were obtained before administration of study drug.

Overall safety was assessed by monitoring/evaluation of TEAEs, physical examinations, vital signs (pulse rate and blood pressure), electrocardiograms (ECGs), and clinical safety laboratory tests at prespecified time points. The potential emergence of anti-alirocumab antibodies was evaluated. PCSK9 levels were evaluated prior and post-apheresis.

The use of all medications and nutritional supplements (including consumption of red yeast products) known to alter serum lipids, including (but not limited to) statins, ezetimibe, fibrates, niacin, and bile acid resins was permitted, as long as that therapy had been stable for at least 8 weeks prior to the screening visit (week-2). Patients were instructed to continue taking their background medical LMT throughout the duration of the study, starting at screening through the end of treatment visit.

Patients' diets remained stable throughout the duration of the study, starting at screening through the end of treatment visit.

Patients' exercise regimens remained stable throughout the duration of the study, starting at screening through the end of treatment visit.

Patient Selection

The study protocol called for approximately 63 patients to be enrolled at up to 15 sites in the US and Germany. The patients were randomized as follows: approximately one-third of enrolled patients (~21) received placebo; and approximately two-thirds of enrolled patients (~42) received alirocumab.

The study population consisted of adult men and women diagnosed with HeFH who were undergoing every 1 or 2 weeks LDL apheresis therapy.

Randomization was stratified according to: Apheresis frequency: QW vs Q2W; and baseline Lp(a) levels: normal (<30 mg/dL) vs elevated (≥30 mg/dL). Since some patients with elevated LDL-C also have elevated Lp(a) levels, stratification ensured adequate representation in the placebo/treatment groups.

Inclusion Criteria:

The patients enrolled in this study were required to meet conditions 1-6 (below) to be eligible for inclusion in the study:

(1) Men and women 18 years of age at the time of the screening visit (2) Diagnosis of HeFH; [Note: Diagnosis of HeFH was made either by genotyping or by clinical criteria. For those patients who had not been genotyped, the clinical diagnosis could be made based on either the Simon Broome criteria with a criteria for definite FH, or the WHO/Dutch Lipid Network criteria with a score >8 points];

(3) Currently undergoing LDL apheresis therapy QW for at least 4 weeks, or Q2W for at least 8 weeks prior to the screening visit (week −2) and have initiated apheresis treatment for at least 5 months prior to that; [Note: Acceptable apheresis techniques are: Double membrane filtration, Immunoadsorption, Heparin-induced LDL precipitation, Direct adsorption of lipids, Dextran sulfate adsorption (plasma), Dextran Sulfate adsorption (whole blood)];

(4) Willing and able to comply with clinic visits and study-related procedures;

(5) Provide signed informed consent; and (6) Able to understand and complete study-related questionnaires.

Exclusion Criteria:

Prospective patients who met any of the following criteria were excluded from the study:

(1) Homozygous FH;

(2) Background medical LMT (if applicable) that had not been stable for at least 8 weeks prior to the screening visit (week −2);

(3) LDL apheresis schedule/apheresis settings that had not been stable for at least 4 weeks prior to the screening visit (week −2) for patients undergoing apheresis weekly and at least 8 weeks prior to the screening visit (week −2) for patients undergoing apheresis bi-weekly;

(4) An LDL apheresis schedule other than QW to Q2W;

(5) Initiation of a new exercise program or exercise that has not remained stable within 8 weeks prior to the screening visit (week −2);

(6) Initiation of a new diet or a diet that has not been stable within 8 weeks prior to the screening visit (week −2);

(7) Use of nutraceuticals or over-the-counter therapies known to affect lipids, at a dose/amount that has not been stable for at least 8 weeks prior to the screening visit (week −2), or between the screening and randomization visit;

(8) Presence of any clinically significant uncontrolled endocrine disease known to influence serum lipids or lipoproteins;

(9) Signs and symptoms of hypothyroidism (thyroid replacement therapy is permitted);

(10) History of bariatric surgery within 12 months prior to the screening visit (week −2);

(11) Unstable weight (variation >5 kg) within 2 months prior to the screening visit (week −2);

(12) Newly diagnosed (within 3 months prior to randomization visit [day 1]) diabetes mellitus or poorly controlled (hemoglobin A1c [HbA1c]>9%) diabetes;

(13) Use of systemic corticosteroids, unless used as replacement therapy for pituitary/adrenal disease with a stable regimen for at least 6 weeks prior to randomization; topical, intra-articular, nasal, inhaled and ophthalmic steroid therapies are not considered as 'systemic' and are allowed;

(14) Use of estrogen or testosterone therapy, unless the regimen has been stable in the past 6 weeks prior to the screening visit (week −2) and no plans to change the regimen during the study;

(15) Systolic blood pressure >160 mm Hg or diastolic blood pressure >100 mm Hg at the screening visit (week −2) or time of randomization (day 1) [Note: Blood pressure assessment for study eligibility may be obtained at a visit occurring between these 2 visits in the event that the patient had not taken, or planned not to take, prescribed hypertensive medications at the screening or randomization visit due to apheresis schedule];

(16) History of a myocardial infarction (MI), unstable angina leading to hospitalization, coronary artery bypass graft surgery (CABG), percutaneous coronary intervention (PCI), uncontrolled cardiac arrhythmia, carotid surgery or stenting, stroke, transient ischemic attack, or carotid revascularization within 3 months prior to the screening visit (week −2), or endovascular procedure or surgical intervention for peripheral vascular disease within 1 month prior to the screening visit (week −2);

(17) History of New York Heart Association Class III or IV heart failure within 12 months prior to the screening visit;

(18) Known history of a hemorrhagic stroke;

(19) History of cancer within the past 5 years, except for adequately treated basal cell skin cancer, squamous cell skin cancer, or in situ cervical cancer;

(20) Known history of a positive test for human immunodeficiency virus;

(21) Use of any active investigational drugs within 1 month or 5 half-lives of screening, whichever is longer;

(22) Patients who have been treated with at least 1 dose of alirocumab or any other anti-PCSK9 monoclonal antibody in any other clinical studies;

(23) Conditions/situations such as: (a) Any clinically significant abnormality identified at the time of screening that, in the judgment of the investigator or any sub-investigator, would preclude safe completion of the study or constrain endpoints assessment; e.g., major systemic diseases, patients with short life expectancy; or (b) Considered by the investigator or any sub-investigator as inappropriate for this study for any reason, e.g.: (i) Deemed unable to meet specific protocol requirements, such as scheduled visits; (ii) Deemed unable to tolerate injections, as per the patient or the investigator; (iii) Investigator or any sub-investigator, pharmacist, study coordinator, other study staff or relative thereof directly involved in the conduct of the protocol, etc.; (iv) Presence of any other conditions (e.g., geographic or social), either actual or anticipated, that the investigator feels would restrict or limit the patient's participation for the duration of the study;

(24) Laboratory findings during screening period (not including randomization labs): (a) Positive test for hepatitis B surface antigen and/or hepatitis C antibody; (b) Positive serum beta-hCG or urine pregnancy test in women of childbearing potential; (c) TG >500 mg/dL (>5.65 mmol/L) (1 repeat lab is allowed); (d) eGFR <15 mL/min/1.73 m2 according to 4-variable Modification of Diet in Renal Disease Study equation (calculated by Central Lab); (e) Alanine aminotransferase (ALT) or aspartate aminotransferase (AST) >3× upper limit of normal (ULN) (1 repeat lab is allowed); (f) CPK >3×ULN (1 repeat lab is allowed);

(25) Known hypersensitivity to monoclonal antibody therapeutics or to any component of the drug product;

(26) Pregnant or breastfeeding women;

(27) Women of childbearing potential not protected by highly-effective method(s) of birth control (as defined in the informed consent form [ICF] and/or in a local protocol addendum) and/or who are unwilling or unable to be tested for pregnancy. Postmenopausal women must be amenorrheic for at least 12 months.

Study Treatments

The study treatment was a single SC injection of 1 mL for a 150 mg dose of alirocumab or placebo, provided in an autoinjector or a prefilled syringe, administered in the abdomen, thigh, or outer area of the upper arm administered Q2W.

During the double-blind treatment period (day 1 to week 18), eligible patients were randomized to receive: Alirocumab 150 mg SC Q2W, or Placebo for alirocumab SC Q2W.

During the open-label treatment period patients received open-label alirocumab 150 mg SC Q2W, starting at week 18 with the last dose administered at week 76.

Sterile alirocumab drug product was supplied at a concentration of 150 mg/mL in histidine, pH 6.0, polysorbate 20, and sucrose in an autoinjector or a prefilled syringe.

Placebo matching alirocumab was supplied in the same formulation as alirocumab, without the addition of protein, in an autoinjector or a prefilled syringe.

All patients and/or caregivers who elected to inject the study drug outside of the clinic on dosing days were trained by the study staff before administering injections. Patients/caregivers were instructed on the administration of study drug at the week 18 visit, and self-administered the first dose of the open-label treatment period at the week 18 visit. Subsequent injections were administered Q2W by the patient (self-injection) or a designated caregiver (spouse, relative, etc.) at a patient-preferred location (e.g., home or place of work).

Patients were also given the option to return to the site Q2W to have the injection administered by study personnel.

Method of Treatment Assignment

Patients were randomly assigned to receive placebo, or alirocumab 150 mg Q2W in a ratio of 1:2, implementing a permuted-block design to ensure even distribution of the treatment assignments. Randomization was stratified according to the frequency of the apheresis procedure (every 7 or 14 days) and Lp(a) levels (normal or elevated). Enrollment was capped so that no more than two-thirds of the patients were undergoing apheresis.

All patients, regardless of treatment assignment in the double-blind treatment period, received alirocumab 150 mg Q2W during the open-label treatment period.

Concomitant Medications

Any treatment administered from the time of informed consent to the end of the follow-up period/final study visit is considered concomitant medication. This includes medications that were started before the study and were ongoing during the study. Concomitant medications were kept to a minimum during the study. If considered necessary for the patient's welfare and unlikely to interfere with study drug, concomitant medications (other than those that are prohibited during the study) were permitted to be given at the discretion of the investigator, with a stable dose (when possible).

Prohibited Medications:

Any background medical LMT that was not stable for at least 8 weeks prior to the screening visit (week 2) was prohibited.

Permitted Medications:

The use of all medications and nutritional supplements (including consumption of red yeast products) known to alter serum lipids including, but not limited to, statins, ezetimibe, fibrates, niacin, and bile acid resins was permitted as long as that therapy had been stable for at least 8 weeks prior to the screening visit (week 2). Patients were instructed to continue taking their background medical LMT throughout the duration of the study, starting at screening through the end of treatment visit.

Patients' diets remained stable throughout the duration of the study, starting at screening through the end of treatment visit.

Patients' exercise programs remained stable throughout the duration of the study, starting at screening through the end of treatment visit.

Study Endpoints

Baseline characteristics will include standard demography (e.g., age, race, weight, height, etc.), disease characteristics including medical history, and medication history for each patient.

Primary Efficacy Endpoint:

The primary efficacy endpoint is the rate of apheresis treatments during the 12-week period from week 7 to week 18, normalized by the number of planned apheresis treatments according to each patient's established schedule at screening, week −10 to week −2.

The normalized rate of apheresis is defined for each patient as: Number of actual apheresis treatments received from week 7 to week 18 divided by Number of planned apheresis treatments per randomization strata at baseline (6 for Q2W or 12 for QW).

In case of patient dropout before week 18, the actual number of apheresis procedures (from week 7 to week 18) will be added to the imputed number of the remaining planned apheresis treatments according to randomization strata for the numerator.

The impact of normalization on the planned apheresis treatments, according to each patient's established schedule at baseline, allows the homogenizing to the same rate scale for patients entering the study with different apheresis schedules (i.e., apheresis QW or Q2W).

Secondary Efficacy Endpoints:

For the following lipid endpoints, such as percent changes from baseline to a specific post-baseline visit during the double-blind treatment period, 2 time points are defined: prior to and after the apheresis procedure. For key efficacy endpoints, the lipid parameters will be analyzed using the assessments collected prior to each apheresis procedure. In the case where the apheresis is not performed at a protocol-specified visit, the single lab assessment planned for collection is used for both time points (i.e., including key efficacy endpoints). The baseline value is defined as the last available value for each of the parameters before the first double-blind dose of study drug.

Secondary endpoints of the present study were as follows:

(1) Percent change from baseline in LDL-C (pre-apheresis) to week 6, regardless of adherence to treatment;

(2) The standardized rate of apheresis treatments during the 4-week period from week 15 to week 18, defined similarly as for the primary efficacy endpoint;

(3) Percent change from baseline in ApoB (pre-apheresis) to week 6, regardless of adherence to treatment;

(4) Percent change from baseline in non-HDL-C (pre-apheresis) to week 6, regardless of adherence to treatment;

(5) Percent change from baseline in total cholesterol (pre-apheresis) to week 6, regardless of adherence to treatment;

(6) Percent change from baseline in ApoA-1 (pre-apheresis) to week 6, regardless of adherence to treatment;

(7) Proportion of patients with 30% reduction in LDL-C (pre-apheresis) at week 6, regardless of adherence to treatment;

(8) Proportion of patients with 50% reduction in LDL-C (pre-apheresis) at week 6, regardless of adherence to treatment;

(9) Percent change from baseline in LDL-C (pre-apheresis) to week 18, regardless of adherence to treatment;

(10) Percent change from baseline in ApoB (pre-apheresis) to week 18, regardless of adherence to treatment;

(11) Percent change from baseline in non-HDL-C (pre-apheresis) to week 18, regardless of adherence to treatment;

(12) Percent change from baseline in total cholesterol (pre-apheresis) to week 18, regardless of adherence to treatment;

(13) Percent change from baseline in ApoA-1 (pre-apheresis) to week 18, regardless of adherence to treatment;

(14) Proportion of patients with 30% reduction in LDL-C (pre-apheresis) at week 18, regardless of adherence to treatment;

(15) Proportion of patients with 50% reduction in LDL-C (pre-apheresis) at week 18, regardless of adherence to treatment;

(16) Change of W-BQ22 index score from baseline to week 18, regardless of adherence to treatment;

(17) Percent change from baseline in Lp(a) (pre-apheresis) to week 6, regardless of adherence to treatment;

(18) Percent change from baseline in HDL-C (pre-apheresis) to week 6, regardless of adherence to treatment;

(19) Percent change from baseline in TG levels (pre-apheresis) to week 6, regardless of adherence to treatment;

(20) Percent change from baseline in Lp(a) (pre-apheresis) to week 18, regardless of adherence to treatment;

(21) Percent change from baseline in HDL-C (pre-apheresis) to week 18, regardless of adherence to treatment;

(22) Percent change from baseline in TG levels (pre-apheresis) to week 18, regardless of adherence to treatment;

(23) The change in ApoB/ApoA-1 ratio (pre-apheresis) from baseline to week 6, regardless of adherence to treatment;

(24) The change in ApoB/ApoA-1 ratio (pre-apheresis) from baseline to week 18, regardless of adherence to treatment;

(25) The standardized rates of apheresis treatments during the 4-week period from week 7 to week 10, defined accordingly as for the primary efficacy endpoint;

(26) The standardized rates of apheresis treatments during the 4-week period from week 11 to week 14, defined accordingly as for the primary efficacy endpoint;

(27) Integrated assessment of frequency of apheresis and LDL-C values for 12-week period from the beginning of week 7 to the end of week 18 (patients ranked according to their LDL-C values and apheresis rate; the mean rank for all patients is determined and the difference of each treated patients LDL-C level or apheresis rate from mean rank for that variable is expressed as a percentage; the percent difference for the 2 variables on per patient basis are added to provide a summated percent difference. When combined and analyzed per treatment group, the resulting number will indicate low LDL-C and/or decreased rate of apheresis);

(28) Proportion of patients achieving LDL-C levels of <200 mg/dL, <130 mg/dL, <100 mg/dL and <70 mg/dL prior to apheresis at week 6, regardless of adherence to treatment;

(29) Proportion of patients achieving LDL-C levels of <200 mg/dL, <130 mg/dL, <100 mg/dL, and <70 mg/dL prior to apheresis at week 18, regardless of adherence to treatment;

(30) Raw values, as well as percent and absolute change in LDL-C and other lipids, from baseline to both time points of each visit, regardless of adherence to treatment, in the double-blind treatment period;

(31) Raw values, as well as percent and absolute change in LDL-C and other lipids, from baseline to each visit, regardless of adherence to treatment, in the open-label treatment period;

(32) Safety parameters (AEs [including adjudicated cardiovascular events], laboratory data, vital signs, and ECG) assessed throughout the study.

Other Endpoints:

(1) Anti-alirocumab antibodies assessed throughout the study; (2) The percent change in high-sensitivity C-reactive protein (hs-CRP) and HbA1c from baseline to weeks 18 and 6; (3) Concentrations of total alirocumab in serum prior to and post-apheresis; (4) Free and total PCSK9 level prior and post-apheresis.

Study Procedures

All laboratory samples were collected before the dose of study drug was administered. Blood samples were collected from patients in fasting conditions, if possible (e.g., overnight [at least 10 hours fast], only water) for all clinic visits for lipid panels. Although preferred, fasting was not a prerequisite for samples for the lipid panels. Alcohol consumption and smoking within 48 hours or intense physical exercise within 24 hours preceding blood sampling was not permitted.

Total-C, HDL-C, TG, ApoB, ApoA-1, and Lp(a) were directly measured by a central laboratory. LDL-C was calculated using the Friedewald formula. If TG values exceeded 400 mg/dL (4.52 mmol/L) then the central lab reflexively measured (via the beta quantification method) the LDL-C rather than calculating it. Non-HDL-C was calculated by subtracting HDL-C from the total-C. Ratio ApoB/ApoA-1 was calculated.

Lipid Panel (Fasting):

Blood samples for the lipid panel (total-C, TG, HDL-C, and calculated LDL-C) were collected after at least a 10-hour fast at pre-specified time points.

Specialty Lipid Panel (Fasting):

Blood samples for the specialty lipid panel (ApoB, ApoA-1, and Lp[a]) were collected after at least a 10-hour fast at pre-specified time points.

Well-Being Questionnaire:

The W-BQ22 was used to assess the impact of hypercholesterolemia and treatment on well-being at specified time points.

Blood Pressure and Heart Rate:

Blood pressure and heart rate were assessed at pre-specified time points. Blood pressure was preferably measured in sitting position under standardized conditions, approximately at the same time of the day, on the same arm, with the same apparatus (after the patient has rested comfortably in sitting position for at least 5 minutes). At the first screening visit, blood pressure was measured in both arms. The arm with the highest diastolic pressure was determined at this visit, and blood pressure was measured on this arm throughout the study. This highest value was recorded in the electronic case report form (eCRF). Heart rate was measured at the time of the measurement of blood pressure.

Physical Examination:

A thorough and complete physical examination was performed at pre-specified time points.

Body Weight and Height:

Body weight were obtained with the patient wearing undergarments or very light clothing and no shoes, and with an empty bladder. The same scale was preferably used throughout the study. The use of calibrated balance scales was recommended, if possible.

Electrocardiogram:

Electrocardiograms were performed before blood is drawn during visits that required blood draws. A standard 12-lead ECG was performed at pre-specified time points. The 12-lead ECGs were performed after at least 10 minutes' rest and in the supine position. The electrodes were positioned at the same place insofar as possible, for each ECG recording throughout the study. The ECG was interpreted locally by the investigator. Any new and/or clinically significant changes in ECG parameters were immediately rechecked for confirmation before making any decision for the concerned patient. Any clinically significant abnormality was documented as an AE/SAE, as applicable. Each trace was analyzed in comparison with the screening recorded trace. All ECG traces were kept as source data. Heart rate was recorded from the ventricular rate, and the PR, QRS, RR and QT intervals will be recorded.

Laboratory Testing:

All laboratory samples (including PK and ADA samples) were collected after assessments were performed and before a dose of study drug was administered at visits that correspond with a dosing day.

Adjudicating Cardiovascular Events:

Adjudicated cardiovascular events included all cardiovascular AEs positively adjudicated. The adjudication categories were as follows: (1) CHD death; (2) Nonfatal MI; (3) Fatal and nonfatal ischemic stroke; (4) Unstable angina requiring hospitalization; (5) Congestive heart failure requiring hospitalization; (6) Ischemia-driven coronary revascularization procedure (PCI, CABG).

Statistical Analyses

It was estimated that a sample size of 63 patients (alirocumab 42: placebo 21) would have at least 85% power to detect a 33% difference in mean apheresis rates using a two-sided significance level and assuming a standard deviation of 40%.

The primary efficacy analysis population was the primary intent-to-treat (ITT) population, defined as all randomized patients. The secondary efficacy analysis population was based on randomized patients who had least one pre-apheresis calculated LDL-C value before the first dose of study drug (or randomization, if the patient did not receive any study drug) and at least one calculated LDL-C value in one of the pre-apheresis analysis windows up to week 6. The statistical analysis was conducted when the last patient completed all efficacy assessments at week 18. LDL-C data were analysed post-hoc using the Kroon formula to estimate the interval means of LDL-C in weeks 6-18 (after potential withdrawal of apheresis therapy).

The standardized rate of apheresis treatments was analysed through the rate of treatments received during the 12-week period (week 7 to week 18), divided by the number of planned treatments (6 for Q2W and 12 for weekly), using the ranked analysis of covariance (ANCOVA) model. The standardized apheresis rate could range from 0 to 1, with 0 indicating that the patient skipped all planned apheresis treatments between week 7 to week 18, and 1 indicating that the patient received all planned treatments. A rate of 0.75 indicated that the patient received 75% of planned apheresis treatments (and skipped 25% of planned treatments). Patient drop-outs were accounted for according to pre-determined criteria. The median treatment difference was determined using the Hodges-Lehmann estimation and 95% confidence intervals (CI) using Moses distribution-free confidence interval.

A hierarchical inferential approach was used to control type I error. As the primary endpoint analysis was significant at the 5% alpha level, key secondary efficacy endpoints were tested sequentially.

Results

Baseline Characteristics

Baseline characteristics of the patients enrolled in the study are summarized in Tables 1 through 4.

TABLE 1

Patient Characteristics at Baseline

| Characteristic | Placebo (N = 21) | Alirocumab 150 mg Q2W (N = 41) | All (N = 62) |
|---|---|---|---|
| Age | | | |
| Mean (SD) | 57.0 (10.5) | 59.5 (9.2) | 58.7 (9.7) |
| Min:Max | 27:73 | 41:79 | 27:79 |
| Age group (years) [n (%)] | | | |
| <65 | 16 (76.2%) | 25 (61.0%) | 41 (66.1%) |
| >=65 | 5 (23.8%) | 16 (39.0%) | 21 (33.9%) |
| Sex [n (%)] | | | |
| Male | 10 (47.6%) | 26 (63.4%) | 36 (58.1%) |
| Female | 11 (52.4%) | 15 (36.6%) | 26 (41.9%) |
| Race [n (%)] | | | |
| White | 21 (100%) | 39 (95.1%) | 60 (96.8%) |
| Black or African American | 0 | 2 (4.9%) | 2 (3.2%) |
| Asian | 0 | 0 | 0 |
| Other, miscellaneous | 0 | 0 | 0 |
| Country [n (%)] | | | |
| Germany | 10 (47.6%) | 20 (48.8%) | 30 (48.4%) |
| U.S. | 11 (52.4%) | 21 (51.2%) | 32 (51.6%) |
| Weight (kg) | | | |
| Mean (SD) | 86.9 (21.3) | 90.0 (16.1) | 88.9 (17.9) |
| Min:Max | 56:124 | 60:124 | 56:124 |
| BMI group (kg/m²) [n (%)] | | | |
| >=30 | 8 (38.1%) | 23 (56.1%) | 31 (50%) |

TABLE 2

Background LMT at Randomization

| Background LMT | Placebo (N = 21) | Alirocumab 150 mg Q2W (N = 41) | All (N = 62) |
|---|---|---|---|
| Taking Statin | 13 (61.9%) | 21 (51.2%) | 34 (54.8%) |
| Taking Maximum Daily Dose of Statin* | 8 (38.1%) | 11 (26.8%) | 19 (30.6%) |
| Any LMT other than Statins | 16 (76.2%) | 26 (63.4%) | 42 (67.7%) |

*Reasons for patients not being on statin or not on maximum daily dose of statin: muscle symptoms, increased CPK, elevated LFTs, concomitant medications, advance age, low BMI, glucose abnormalities, regional practice, potential for cognitive impairment.

TABLE 3

History of Apheresis Treatments

| | Placebo (N = 21) | Alirocumab 150 mg Q2W (N = 41) | All (N = 62) |
|---|---|---|---|
| Frequency in which the subject is undergoing apheresis | | | |
| QW | 9 (42.9%) | 18 (43.9%) | 27 (43.5%) |
| Q2W | 12 (57.1%) | 23 (56.1%) | 35 (56.5%) |
| Time from first known apheresis treatment (years) | | | |
| Mean (SD) | 8.32 (8.11) | 7.22 (7.60) | 7.59 (7.73) |
| Median | 5.32 | 4.54 | 4.89 |
| Min:Max | 0.5:27.3 | 0.5:32.9 | 0.5:32.9 |

TABLE 4

Lipid Parameters at Baseline

| Lipid Parameter | Placebo (N = 21) | Alirocumab 150 mg Q2W (N = 41) | All (N = 62) |
|---|---|---|---|
| Calculated LDL-C (mg/dL) | | | |
| Mean (SD) | 191.6 (68.9) | 175.1 (54.6) | 180.7 (59.7) |
| Median | 180.0 | 176.0 | 179.5 |
| Q1:Q3 | 140.0:240.0 | 129.0:219.0 | 133.0:227.0 |
| Min:Max | 81:316 | 53:275 | 53:316 |
| Non-HDL-C (mg/dL) | | | |
| Mean (SD) | 224.5 (68.0) | 210.3 (62.8) | 215.1 (64.4) |
| Min:Max | 90:313 | 56:265 | 56:313 |
| Total-C (mg/dL) | | | |
| Mean (SD) | 272.3 (73.6) | 256.9 (60.6) | 262.1 (65.1) |
| Min:Max | 147:399 | 140:377 | 140:399 |
| HDL-C (mg/dL) | | | |
| Mean (SD) | 47.8 (17.3) | 46.6 (16.2) | 47.0 (16.4) |
| Min:Max | 24:98 | 24:108 | 24:108 |
| TGs (mg/dL) | | | |
| Mean (SD) | 164.4 (61.6) | 176.0 (87.2) | 172.1 (79.0) |
| Min:Max | 81:308 | 59:393 | 59:393 |
| Lipoprotein-(a) (mg/dL) | | | |
| Mean (SD) | 45.7 (49.5) | 43.0 (54.5) | 43.9 (52.4) |
| Min:Max | 7:202 | 1.5:285 | 21.5:285 |

Seventy-six patients with heFH undergoing regular weekly or Q2W lipoprotein apheresis provided consent to participate and were screened. As summarized in Tables 1-4, a total of 62 patients (age: mean±SD age, 58.7±9.7 years) were randomized. 58.1% of randomized patients were male. At screening visit, 28 patients were on no statin due to tolerability and 34 patients indicated taking daily statin with 19 of them taking the maximum daily dose. All patients had atherosclerotic disease (coronary and/or cerebrovascular and/or peripheral) and 56.5% had a family history of coronary heart disease. On average patients were on regular lipoprotein apheresis for (mean±SD) 7.6±7.7 years; median (Min:Max): 4.9 (0.5:32.9) years. The apheresis frequency was Q2W (56.5%) and QW (43.5%). 16.1% of patients had diabetes. 1.6% of patients had chronic kidney disease. Baseline mean LDL-C was 4.7 mmol/L (180.7 mg/dL); median (Min:Max): 4.7 (1.4:8.2) mmol/L [179.5 (53.0:316.0) mg/dL]. Baseline mean Lp(a) was 43.9 mg/dL (median [Min:Max]: 19.0 [1.5:285.0] mg/dL).

Sixty patients completed the 6-week double-blind treatment period (40 [97.6%] in the alirocumab group and 20 [95.2%] in the placebo group) (i.e. when apheresis rate was determined by the patient's established schedule), and 57 completed the 18-week double-blind treatment period (37 [90.2%] and 20 [95.2%], respectively), when the apheresis schedule was determined by LDL-C value previously achieved. Of the 5 (8.1%) patients who prematurely discontinued study treatment, 1 (4.8%) was on placebo (withdrawn due to adverse events) and 4 (9.8%) were on alirocumab (2 were withdrawn for adverse events and 1 for poor compliance, 1 patient withdrew consent).

The mean±standard deviation (SD) age of the population was 58.7±9.7 years, 36 (58.1%) patients were men, and 60 (96.8%) were white. The median (minimum, maximum) duration of apheresis treatments before entry into the study was 4.9 (0.5, 32.9) years.

The baseline characteristics were balanced between treatment groups. The mean calculated baseline LDL-C (at study entry) was 4.5±1.4 mmol/L (175.1 mg/dL) in the alirocumab group and 5.0±1.8 mmol/L (191.6 mg/dL) in the placebo group (P=0.35). Twenty-seven (43.5%) patients followed a weekly apheresis schedule at baseline and 35 (56.5%) patients followed a Q2W schedule. The mean LDL-C value in patients undergoing weekly apheresis was 3.9±1.3 mmol/L (151.3±51.3 mg/dL) versus 5.3±1.4 mmol/L (204.9±55.7 mg/dL) in patients undergoing Q2W apheresis. Thirty-eight (61.3%) patients had normal baseline lipoprotein (a) levels (<30 mg/dL) and 24 (38.7%) had elevated levels. Thirty-four (54.8%) patients were taking a statin at screening, 19 (55.9%) of whom were on a maximum daily dose. Baseline LDL-C values were (4.0±1.4 mmol/L (155.0±54.6 mg/dL) among statin-treated patients compared with 5.4±1.4 mmol/L (208.0±53.2 mg/dL) in patients not taking a statin. Thirty patients (48.4%) were from Germany and 32 (51.6%) from the United States.

The mean±SD duration of injection exposure was 17.4±2.3 weeks (8.6±1.3 injections) in the alirocumab group and 17.5±3.1 weeks (8.4±1.7 injections) in the placebo group.

Efficacy Results

Efficacy results are summarized in Tables 5 through 8.

Table 5 shows the standardized rate of apheresis from week 7 to week 18

TABLE 5

Primary Efficacy Analysis: Standardized Rate of Apheresis Treatments from Week 7 to Week 18 (ITT)

| Standardized rate of apheresis treatments from week 7 to week 18 | Placebo (N = 21) | Alirocumab 150 mg Q2W (N = 41) |
|---|---|---|
| Mean (SD) | 0.806 (0.191) | 0.128 (0.242) |
| Median | 0.833 | 0.000 |
| Min:Max | 0.42:1.00 | 0.00:1.00 |
| Hodges-Lehmann estimate of median treatment difference | | 0.750 |
| 95% Moses distribution free CI | | (0.667 to 0.833) |
| p-value vs. placebo | | <.0001 |

Only legitimate apheresis treatment skipping per point-of-care LDL-C value is counted as "apheresis not occurred". Missing apheresis treatment information (for any reason) from week 7 to week 18 is imputed to an outcome of the apheresis treatment "occurred" at the visit.
The standardized rate of apheresis treatments is defined as: Number of actual apheresis treatments/planned apheresis treatments (6 for Q2W or 12 for QW).

TABLE 6

Standardized Rate of Apheresis Treatments from Week 7 to Week 18 (ITT)

| Standardized rate of apheresis treatments [n (%)] | Placebo (N = 21) | Alirocumab 150 mg Q2W (N = 41) |
|---|---|---|
| 0 | 0 | 26 (63.4%) |
| >0 and <=0.25 | 0 | 7 (17.1%) |
| >0.25 and <=0.5 | 3 (14.3%) | 5 (12.2%) |
| >0.5 and <=0.75 | 5 (23.8%) | 1 (2.4%) |
| >0.75 and <1 | 7 (33.3%) | 1 (2.4%) |
| 1 | 6 (28.6%) | 1 (2.4%) |

Only legitimate apheresis treatment skipping per point-of-care LDL-C value is counted as "apheresis not occurred". Missing apheresis treatment information (for any reason) from week 7 to week 18 is imputed an outcome of the apheresis treatment "occurred" at the visit. Two patients (1 in placebo and 1 in alirocumab) terminated study treatments before week 6 and the standardized apheresis rates were imputed as 1.

The primary efficacy endpoint achieved statistically significant benefit in favour of alirocumab-treated patients, with a Hodges-Lehmann median estimate of the treatment difference versus placebo of 0.75 (95% confidence interval: 0.67-0.83). Therefore, alirocumab-treated patients had a 0.75 (75%) additional reduction in the standardized rate of apheresis treatments versus placebo-treated patients (P<0.0001). The median treatment difference in the standardized rate of apheresis treatments from week 7 to week 18, when apheresis treatment was determined by LDL-C concentration previously achieved, was 0.75 (95% CI 0.58-0.92) for patients who had been undergoing weekly apheresis and 0.67 (95% CI 0.50-1.00) for those on a Q2W schedule, in favour of alirocumab.

The median treatment difference in the standardized rate of apheresis treatments over the 4-week period (week 15 to week 18) was 0.50 (95% CI 0.50 to 1.00; P<0.0001) in favour of alirocumab, indicating a 50% reduction in the standardized rate of apheresis treatments versus placebo.

Figure 2:
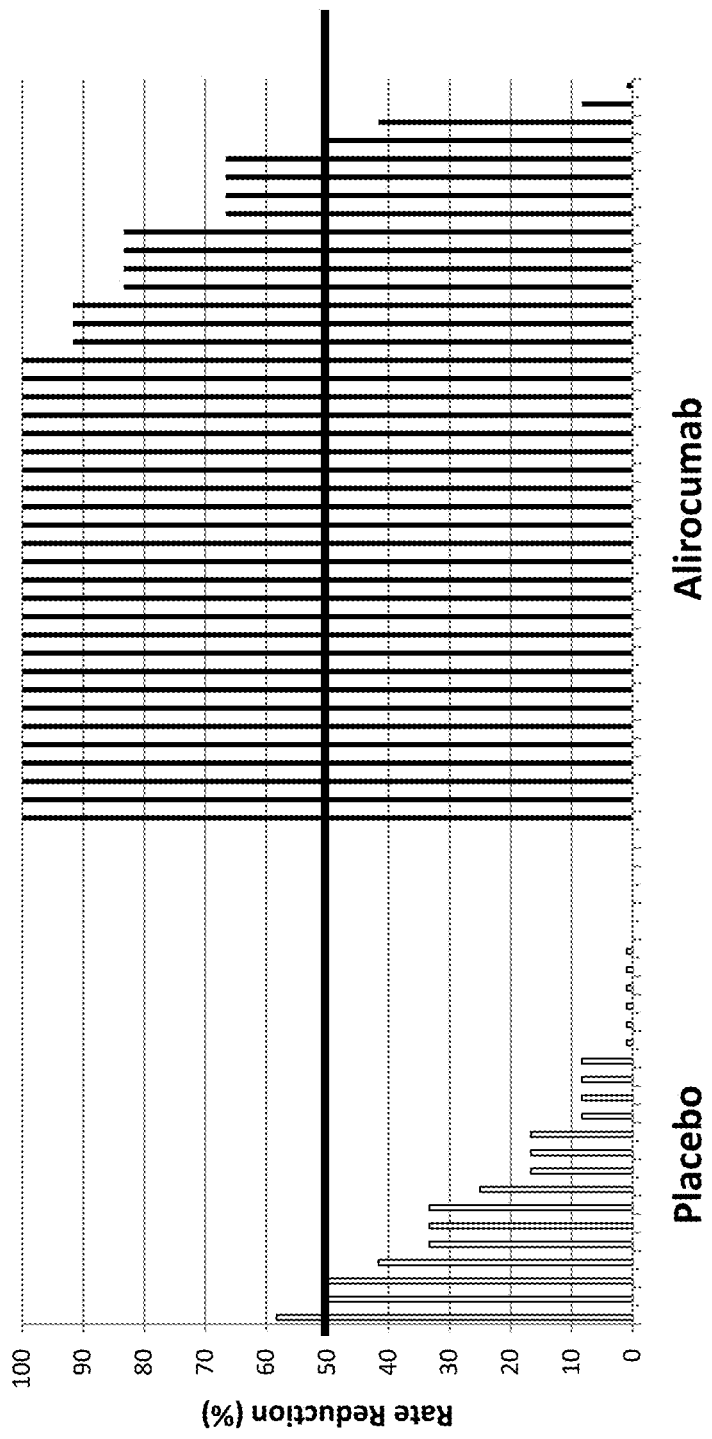
FIG. 2 is a waterfall plot showing individual patients' reductions in rate of apheresis treatments from week 7 to week 18 in the placebo and alirocumab-treated patient groups (ITT population). Only apheresis treatment skipping per point-of-care LDL-C value is counted as "apheresis not occurred". Missing apheresis treatment information (for any reason) from week 7 to week 18 is imputed to an outcome of the apheresis treatment "occurred" at the visit.
Figure 3:
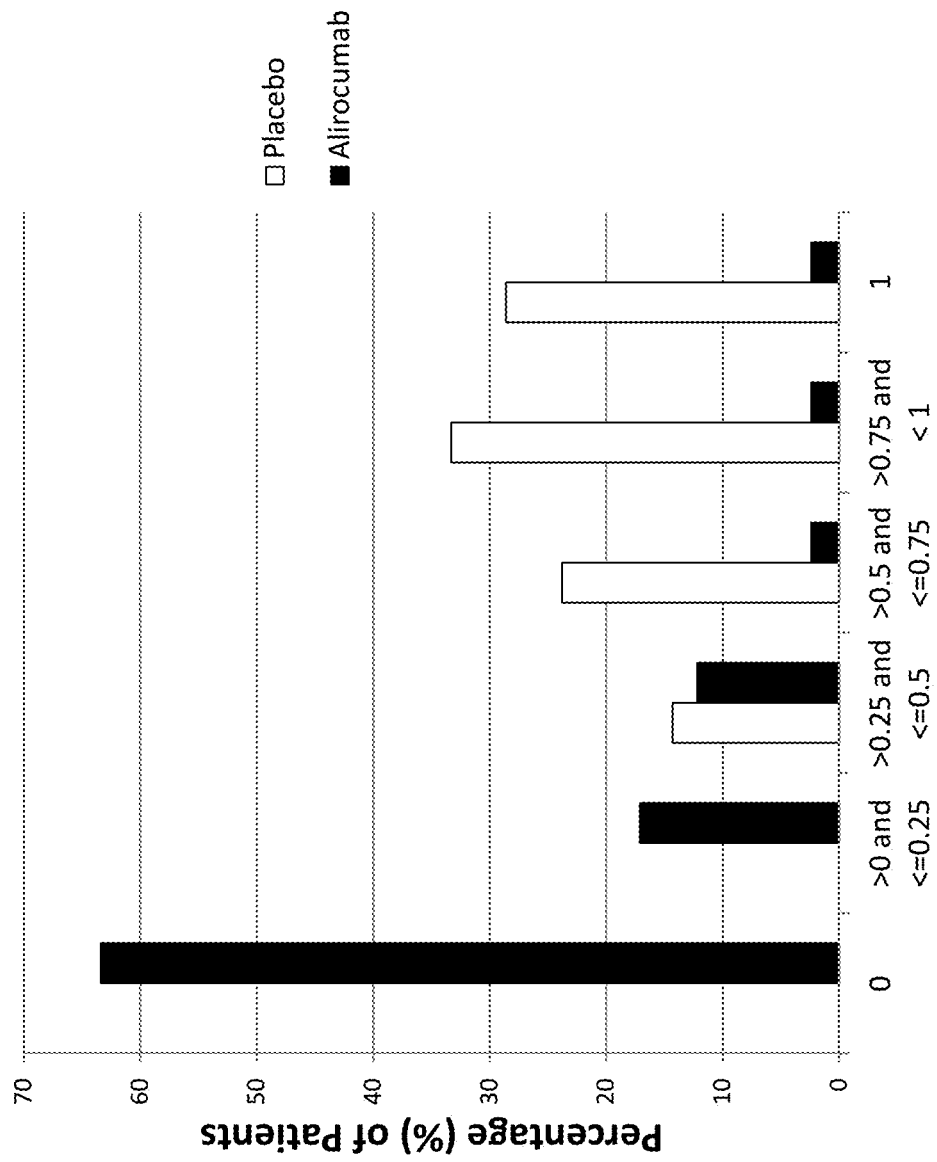
FIG. 3 shows the standardized apheresis rate from week 7 to week 18 in the placebo and alirocumab-treated patient groups. Apheresis rates are shown along the x-axis; the y-axis shows the percentage of patients exhibiting the corresponding apheresis rate range.
Figure 4:
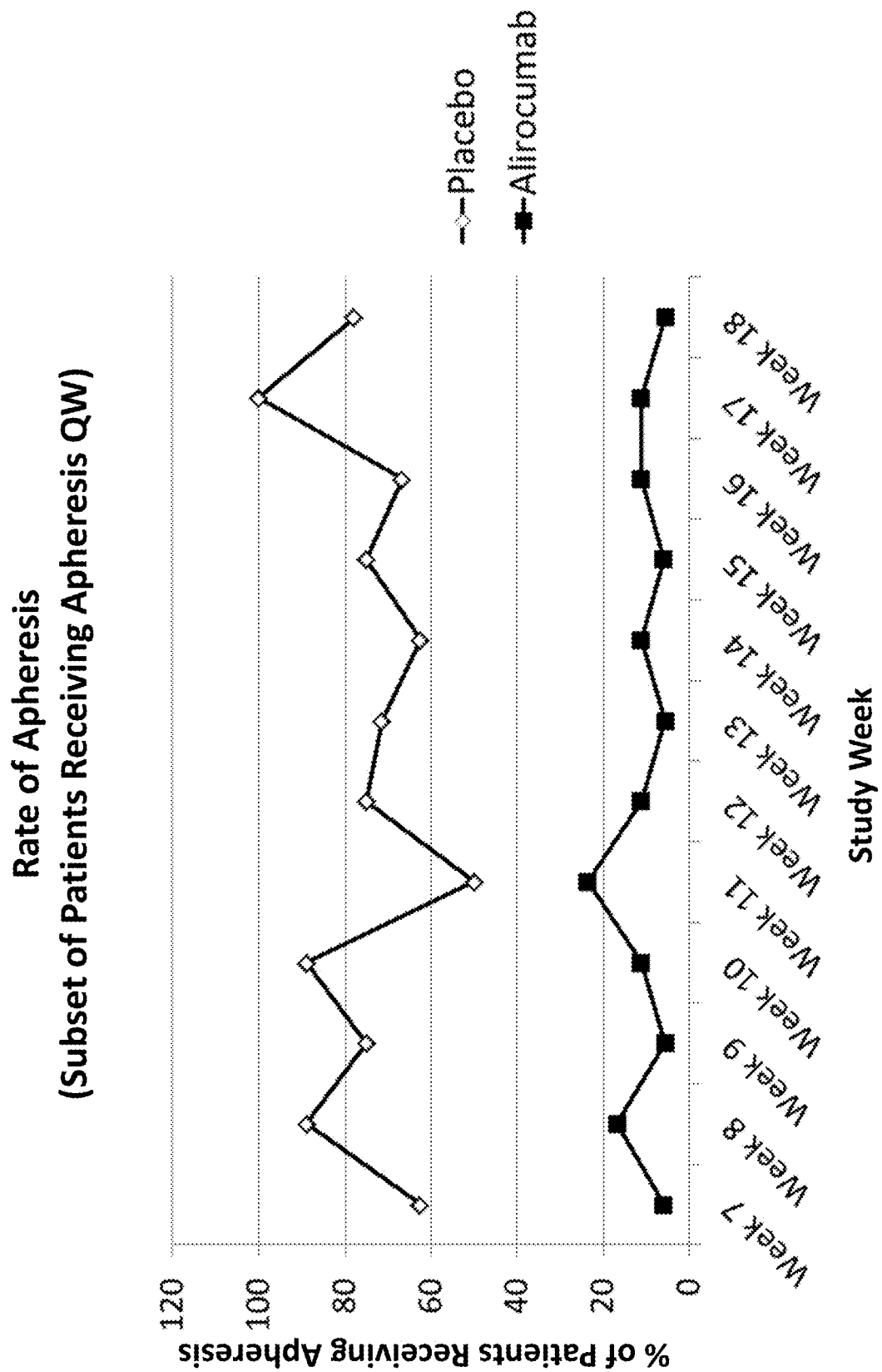
FIG. 4 shows the percent of patients receiving apheresis in the placebo and alirocumab-treated patient groups at different time points from week 7 through week 18 of the study. The patients shown in this chart are those who were receiving apheresis weekly (QW) at the start of the study.
Figure 5:
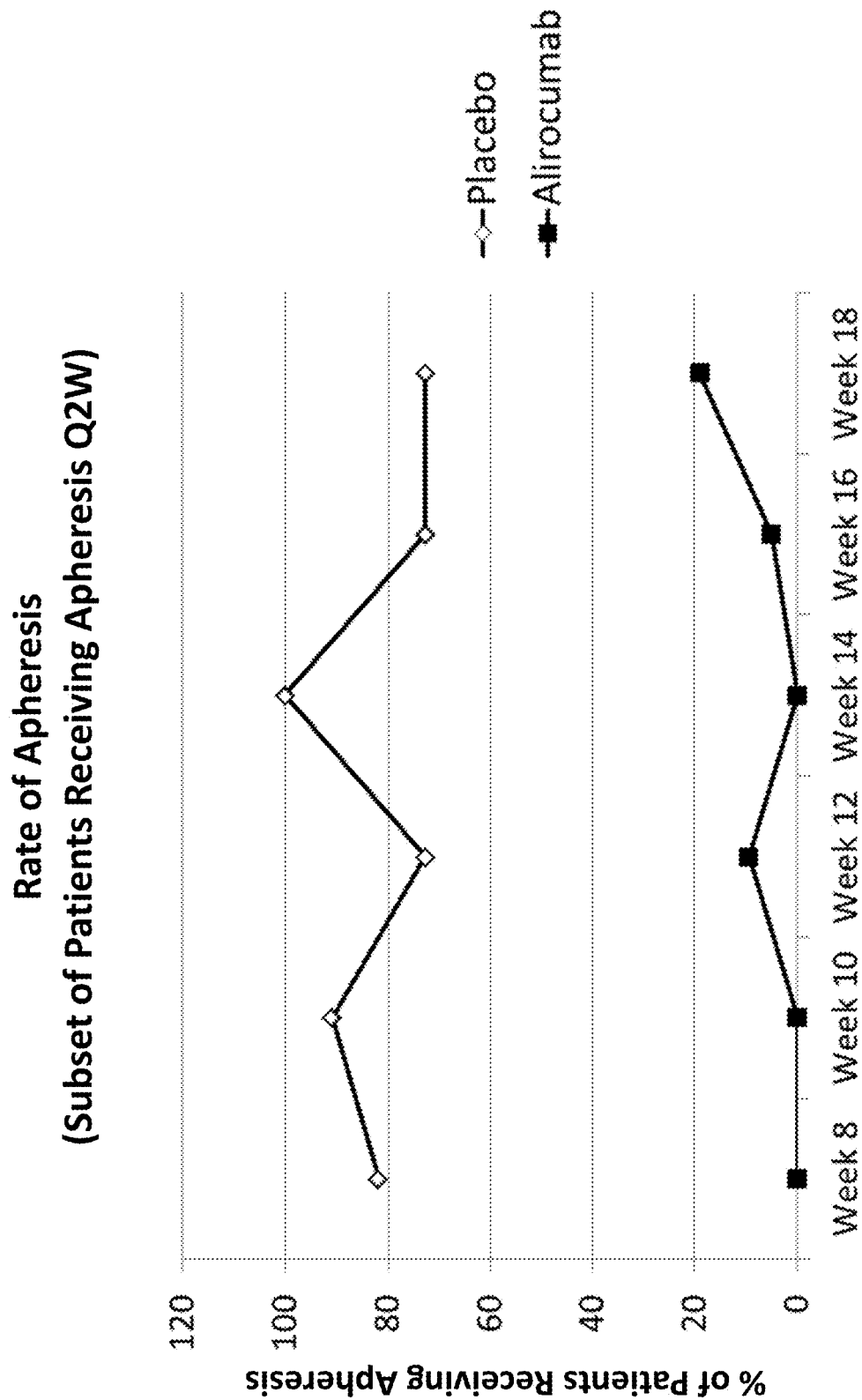
FIG. 5 shows the percent of patients receiving apheresis in the placebo and alirocumab-treated patient groups at different time points from week 7 through week 18 of the study. The patients shown in this chart are those who were receiving apheresis once every other week (Q2W) at the start of the study.
Figure 6:
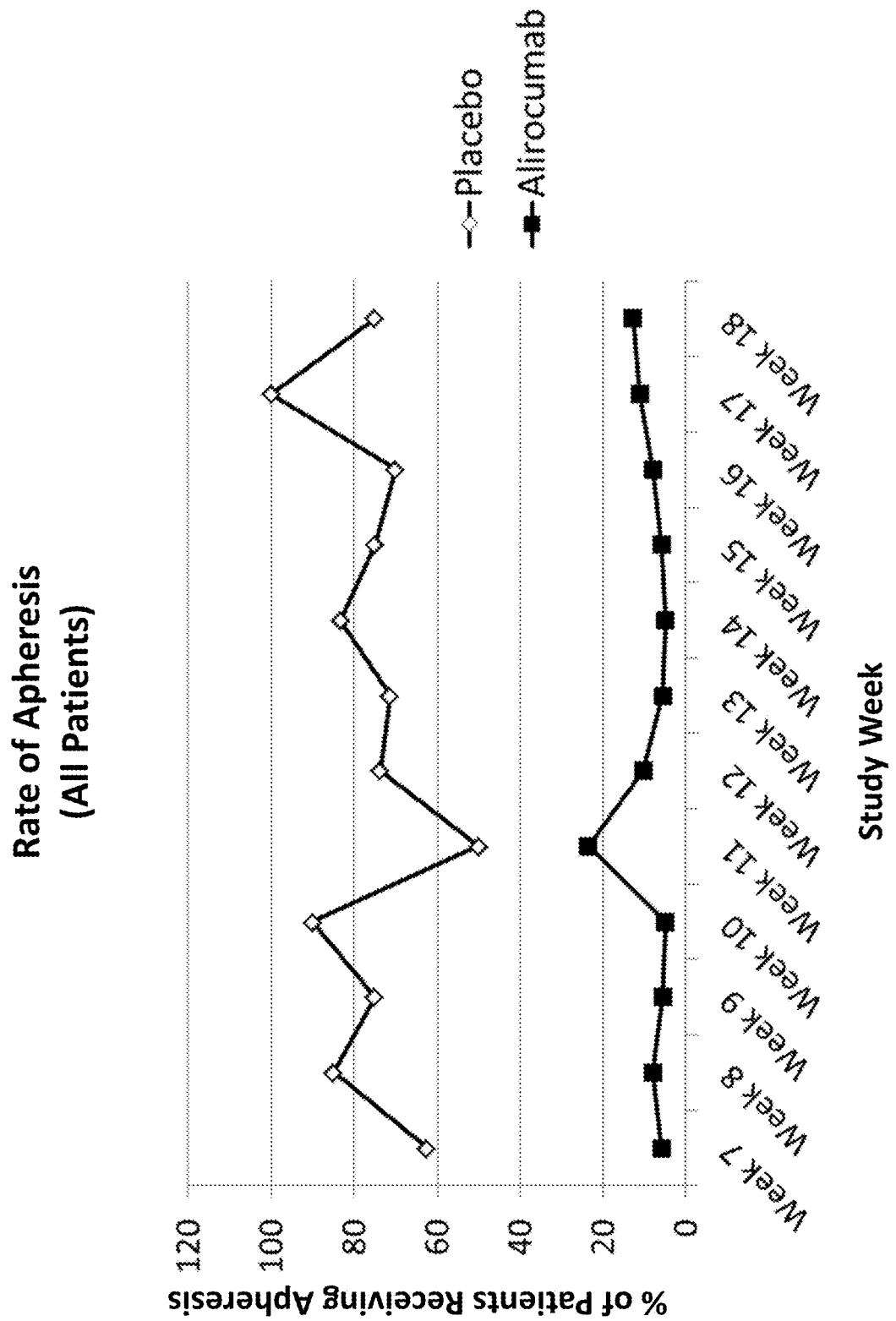
FIG. 6 shows the percent of patients receiving apheresis in the placebo and alirocumab-treated patient groups at different time points from week 7 through week 18 of the study. The patients shown in this chart represent all patients enrolled in the study.

As shown in Table 5, the mean rate of apheresis treatments in alirocumab-treated patients was 0.128, whereas the mean rate of apheresis treatments in the placebo group was 0.806. A graphical representation of the percent reduction in rate of apheresis treatments for individual alirocumab-treated patients compared with individual patients in the placebo group over the 12-week period is shown in FIG. 2. During this period, 63.4% of patients on alirocumab had no apheresis procedures, and 92.7% avoided at least half of the procedures. That is, 26 patients in the alirocumab-treated group achieved a 100% reduction in rate of apheresis treatments. By contrast, none of the patients in the placebo group achieved a 100% reduction in rate of apheresis treatments. These results are also reflected in Table 6 and FIGS. 3 through 6, illustrating the rate of apheresis treatments for patients in placebo and alirocumab-treated groups from week 7 to week 18 of the study. The results show that patients who added alirocumab to their existing treatment regimen were able to significantly reduce the frequency of their standardized apheresis therapy over 12 weeks by 75% compared to placebo (P<0.0001).

Figure 7:
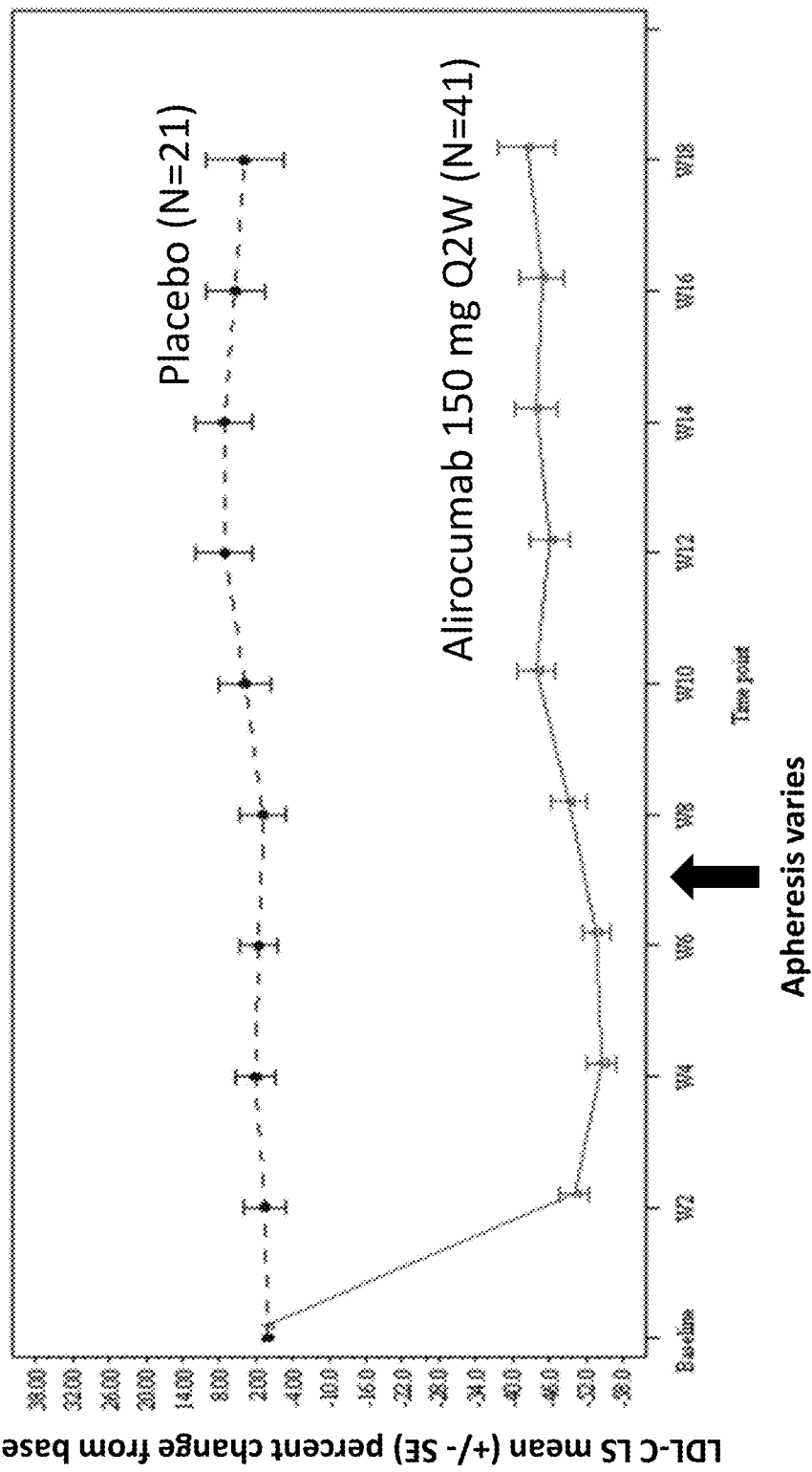
FIG. 7 shows the calculated LDL-C percentage change from baseline in the placebo and alirocumab-treated patient groups at different time points throughout the course of the study. The black arrow labeled "apheresis varies" indicates the time point at which the apheresis frequency going forward was determined for individual patients based on LDL-C level. Prior to this time point, patients received apheresis at a fixed frequency based on the individual patient's established schedule.
Figure 8:
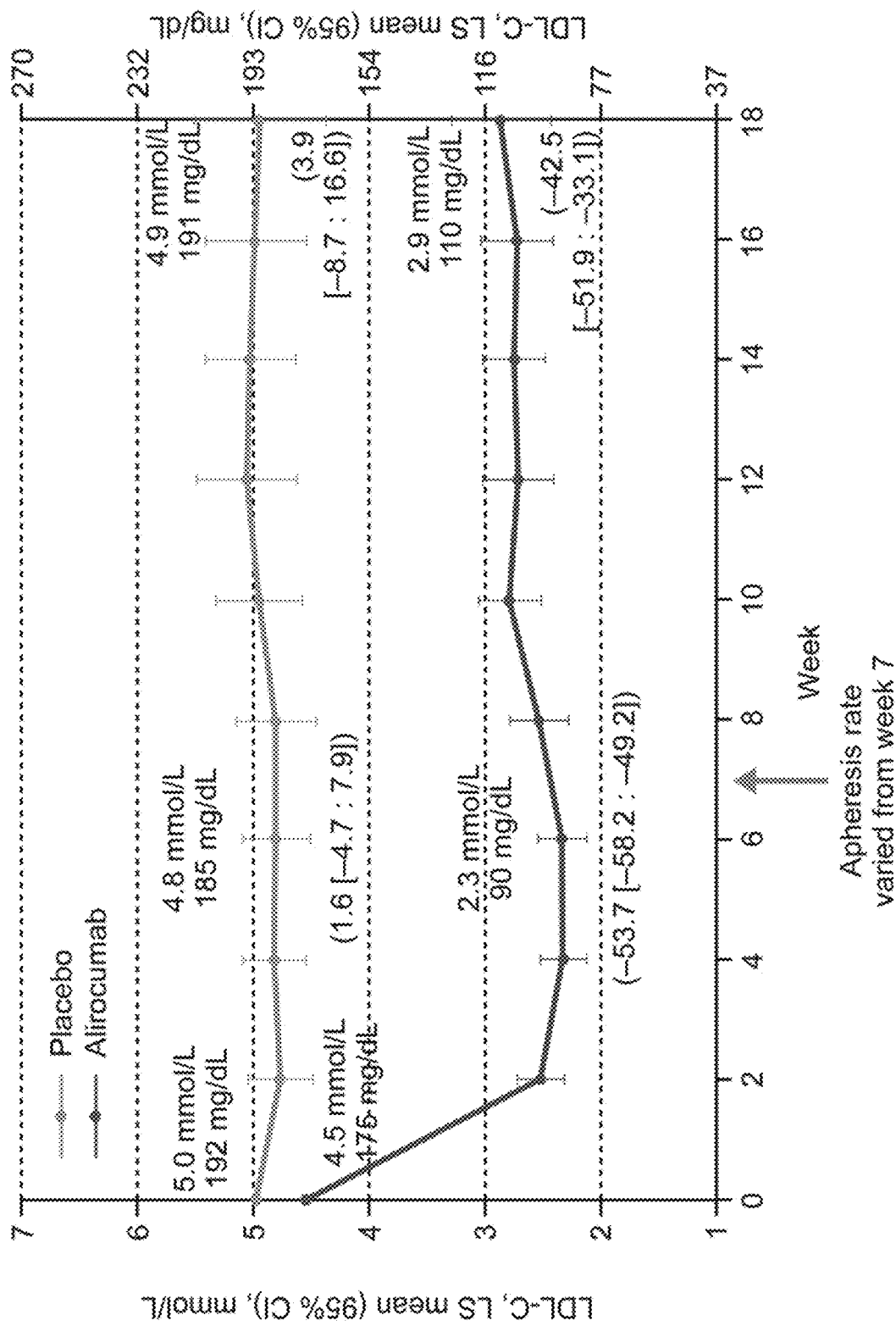
FIG. 8 shows the calculated LDL-C levels (expressed in terms of LS-mean [+/−SE] mg/dL) in the placebo and alirocumab-treated patient groups at different time points throughout the course of the study. The black arrow labeled "apheresis varies" indicates the time point at which the apheresis frequency going forward was determined for individual patients based on LDL-C level. Prior to this time point, patients received apheresis at a fixed frequency based on the individual patient's established schedule.

Table 7 and FIGS. 7 and 8 show the effects of alirocumab treatment as compared to placebo in terms of changes in serum LDL-C levels over the course of the study. Overall, alirocumab-treated patients exhibited a mean reduction in LDL-C from baseline greater than 50% at week 6, while patients in the placebo group did not exhibit any significant degree of LDL-C reductions.

TABLE 7

LDL-C Percent Change from Baseline Analysis at Week 6 (pre-apheresis): MMRM-ITT

| Percent change from baseline in Calculated LDL Cholesterol | Placebo (N = 21) | Alirocumab 150 mg Q2W (N = 41) |
|---|---|---|
| Baseline (mg/dL) | | |
| Mean (SD) | 191.6 (68.9) | 175.1 (54.6) |
| Median | 180.0 | 176.0 |
| Min:Max | 81:316 | 53:275 |
| Week 6 percent change from baseline (%) | | |
| LS Mean (SE) | 1.6 (3.1) | −53.7 (2.3) |
| LS mean difference (SE) vs placebo | | −55.3 (3.9) |
| 95% CI | | (−63.1 to −47.5) |
| p-value vs placebo | | <.0001 |

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point and strata-by-time point interaction, as well as the continuous fixed covariates of baseline calculated LDL-C value and baseline calculated LDL-C value-by-time point interaction. Time points in the model include bi-weekly timepoints from week 2 (pre-apheresis) to week 18 (pre-apheresis).

Key secondary efficacy results for placebo and alirocumab-treated patients are summarized in Table 8.

TABLE 8

Key Secondary Efficacy Analysis Results

| Endpoints | Placebo Result | Alirocumab Result | Comparison | P-value |
|---|---|---|---|---|
| Calculated LDL-C Percent change from baseline to Week 6 (Pre-apheresis) | LS mean: 1.6% | LS mean: −53.7% | Diff: −55.3% | <0.0001 |
| Rate of apheresis treatments Week 15 to week 18 | Median: 1.000 | Median: 0.000 | Diff*: 0.500 | <0.0001 |
| Apo B Percent change from baseline to Week 6 (Pre-apheresis) | LS mean: 1.2% | LS mean: −42.8% | Diff: −44.0% | <0.0001 |
| non-HDL-C Percent change from baseline to Week 6 (Pre-apheresis) | LS mean: 2.8% | LS mean: −47.1% | Diff: −50.0% | <0.0001 |
| Total-C Percent change from baseline to Week 6 (Pre-apheresis) | LS mean: 3.1% | LS mean: −36.4% | Diff: −39.4% | <0.0001 |
| Apo A-1 Percent change from baseline to Week 6 (Pre-apheresis) | LS mean: 0.0% | LS mean: 4.2% | Diff: 4.2% | 0.3012 |
| ≥30% reduction in LDL-C from baseline to Week 6 (Pre-apheresis) | Proportion: 4.8% | LS mean: 95.1% | Odds Ratio: 144.4 | <0.0001 |
| ≥50% reduction in LDL-C from baseline to Week 6 (Pre-apheresis) | Proportion: 0 | LS mean: 63.4% | Odds Ratio: 48.1 | 0.0006 |
| Calculated LDL-C Percent change from baseline to Week 18 (Pre-apheresis) | LS mean: 3.9% | LS mean: −42.5% | Diff: −46.4% | <0.0001 |
| Apo B Percent change from baseline to Week 18 (Pre-apheresis) | LS mean: 1.8% | LS mean: −33.5% | Diff: −35.2% | <0.0001 |
| non-HDL-C Percent change from baseline to Week 18 (Pre-apheresis) | LS mean: 4.7% | LS mean: −45.8% | Diff: −40.4% | <0.0001 |
| Total-C Percent change from baseline to Week 18 (Pre-apheresis) | LS mean: 4.6% | LS mean: −27.3% | Diff: −31.9% | <0.0001 |
| Apo A-1 Percent change from baseline to Week 18 (Pre-apheresis) | LS mean: −0.7% | LS mean: 8.1% | Diff: 8.8% | 0.0404 |
| ≥30% reduction in LDL-C from baseline to Week 18 (Pre-apheresis) | Proportion: 0 | LS mean: 65.9% | Odds Ratio: 39.8 | <0.0001 |
| ≥50% reduction in LDL-C from baseline to Week 18 (Pre-apheresis) | Proportion: 0 | LS mean: 43.9% | Odds Ratio: 18.8 | <0.0001 |
| W-BQ22 (Well-being measure) Change from baseline to Week 18 | LS mean: −0.34 | LS mean: −0.86 | Diff: −0.52 | 0.6887 |
| Lp(a) Percent change from baseline to Week 6 (Pre-apheresis) | LS mean: −4.0% | LS mean: −18.0% | Diff: −14.1% | 0.0262 |
| HDL-C Percent change from baseline to Week 6 (Pre-apheresis) | LS mean: 4.0% | LS mean: 9.2% | Diff: 5.2% | 0.2168 |
| TG Percent change from baseline to Week 6 (Pre-apheresis) | LS mean: 3.0% | LS mean: −12.9% | Diff: −15.8% | 0.0204 |
| Lp(a) Percent change from baseline to Week 18 (Pre-apheresis) | LS mean: −0.9% | LS mean: −5.0% | Diff: −4.1% | 0.6805 |
| HDL-C Percent change from baseline to Week 18 (Pre-apheresis) | LS mean: 2.5% | LS mean: 10.5% | Diff: 8.0% | 0.2022 |
| TG Percent change from baseline to Week 18 (Pre-apheresis) | LS mean: 4.2% | LS mean: −1.4% | Diff: −5.6% | 0.5770 |

The mean pre-apheresis LDL-C value decreased from 4.5 mmol/L (175 mg/dL) at baseline to 2.3 mmol/L (90 mg/dL) at week 6 in the alirocumab group; corresponding data for patients in the placebo group are 5.0 mmol/L (192 mg/dL) and 4.8 mmol/L (185 mg/dL) (FIG. 2). The LS mean±SE (95% CI) percent change in pre-apheresis LDL-C from baseline at week 6 was −53.7±2.3 (−58.2 to −49.2) in the alirocumab group and 1.6±3.1 (−4.7 to 7.9) in the placebo group (LS mean±SE percent difference −55.3±3.9, 95% CI −63.1 to −47.5; P<0.0001). By week 18, the mean LDL-C value in the alirocumab group had risen slightly, to 2.9 mmol/L (110 mg/dL), compared with 4.9 mmol/L (191 mg/dL) in the placebo group (LS mean±SE percent difference −46.4±7.9, 95% CI 62.3 to −30.5; P<0.0001).

A cross-validation, comparing point-of-care LDL-C values with central laboratory values, showed that both measures were highly correlated (Pearson's correlation 0.86).

Percent change from baseline to week 18 in lipoprotein (a) was −5.7% for alirocumab versus −3.0% for placebo among patients with normal baseline values, and 4.9% versus 7.6%, respectively, in patients with elevated baseline values. During weeks 7-18, when apheresis treatment could be withdrawn, alirocumab treatment was associated with a lower mean±SD time-averaged LDL-C value (using the Kroon formula 18) over the course of the (potential) apheresis interval of 2.4±1.3 mmol/L (92.7±50.2 mg/dL) versus 3.8±1.7 mmol/L (146.7±65.6 mg/dL) for placebo (P<0.0001).

In a post-hoc analysis, the time-averaged LDL-C values in the alirocumab-treated patients were consistently lower than those in the placebo-treated patients.

Safety

TEAEs were reported by 75.6% of patients in the alirocumab group and by 76.2% of patients in the placebo group, none of which were fatal. The rates of serious adverse events (9.8% for alirocumab and 9.5% for placebo) and events leading to treatment discontinuation (4.9% and 4.8%, respectively) were also similar in both groups.

Three patients (7.3%) in the alirocumab group and none in the placebo group had two consecutive pre-apheresis calculated LDL-C values <0.7 mmol/L (25 mg/dL). Two of these patients had at least one adverse event, one of which had several serious adverse events (pneumonia, acute myocardial infarction, acute respiratory failure, cardiac failure congestive, sepsis and aortic valve stenosis). Twenty-seven patients (23 [56.1%] on alirocumab and 4 [19.0%] on placebo) had two consecutive LDL-C values <0.7 mmol/L after apheresis, of which 15 (65.2%) and 2 (50.0%), respectively, had an adverse event. None of the events was serious but one patient (4.3%) discontinued treatment with alirocumab.

Summary and Conclusions

The present study shows that patients receiving alirocumab exhibited a reduced rate of apheresis treatments, and a reduced number of apheresis treatments over the course of the study, compared to patients receiving placebo. In particular, alirocumab treatment resulted in a higher reduction in the rate of apheresis treatments as compared to the placebo treatment, by a median estimate of 0.75 or 75% (p<0.0001).

The present study also demonstrated that 63.4% of patients treated with alirocumab had no apheresis performed vs. 0% in placebo treated patients (that is, no patients in the placebo-treated group were able to forego apheresis treatments completely, whereas 63.4% of patients in the alirocumab treatment arm were able to eliminate apheresis treatments altogether following alirocumab treatment). In addition, 92.7% of patients treated with alirocumab had at least 50% reduction in frequency of apheresis vs 14.3% in placebo treated patients. Moreover, alirocumab reduced LDL-C by 55% (vs. PBO) at week 6 from 175 mg/dl to 89.5 mg/dl. Significant reductions in apoB, non-HDL-C and TC were also observed in alirocumab-treated patients. Alirocumab treatment reduced the standardized rate of apheresis treatments from week 15 to week 18.

With regard to safety, subcutaneous administration of alirocumab in patients with HeFH undergoing LDL apheresis therapy every 1 or 2 weeks was generally safe and well tolerated. The number of patients reporting TEAEs overall and AESIs were comparable across treatment groups.

All of the patients in this study were at high cardiovascular risk and had taken LLT previously, including statins. At screening, only 54.8% of the patients were taking a statin, 55.9% of whom were on a maximally tolerated dose. A large proportion of the overall population reported a history of down-titration of statin treatment due to tolerability issues (43.5%) and 62.9% reported changing to a different statin. Various reasons were given for not taking a statin or for not taking it at the maximum daily dose, ranging from muscle symptoms to anxiety about side-effects, and regional practices/local labelling, indicating that patients with heFH on apheresis present a diverse and difficult-to-treat population, with limited treatment options.

Patients in the USA showed different characteristics to those in Germany, with higher baseline LDL-C, greater prevalence of statin intolerance, and a less frequent apheresis regimen. In the USA, lipoprotein apheresis for heFH is often only considered for patients who, after 6 months, do not have an adequate response to maximum tolerated drug therapy and have elevated LDL-C plus other cardiovascular risk factors. In Germany, where apheresis centers are more common, apheresis is considered within 12 months of failure of diet and LLT, and at a lower LDL-C threshold, and weekly is preferred to Q2W apheresis. Furthermore, recommendations for LDL-C lowering from Europe are based on a risk-stratified treat-to-target approach, whereas US guidelines advocate a dose-adapted approach. In view of the approach adopted in European guidelines, in which the target LDL-C value is <1.8 mmol/L (70 mg/dL), German patients on alirocumab with LDL-C above this target value would still meet the criteria for apheresis. Consequently, LLT with alirocumab may prove complementary to lipoprotein apheresis in patients with very high LDL-C or who fail to meet the target LDL-C value.

In conclusion, this study achieved significant reduction in the primary efficacy endpoint and demonstrates that PCSK9 inhibitors such as alirocumab are an effective therapeutic option to reduce or eliminate a patient's need for lipoprotein apheresis therapy, or to delay the requirement for such treatments.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for eliminating a patient's need for lipoprotein apheresis therapy, or reducing the frequency of lipoprotein apheresis therapy required by a patient to achieve a target lipoprotein level, the method comprising selecting a patient with hypercholesterolemia who is being or has been treated with lipoprotein apheresis at an initial (pre-treatment) frequency, and administering one or more doses of a PCSK9 inhibitor to the patient, thereby lowering the level of at least one lipoprotein in the serum of the patient and reducing frequency of lipoprotein apheresis required by the patient to achieve a target lipoprotein level, wherein the PCSK9 inhibitor is an antibody or antigen-binding fragment thereof that specifically binds PCSK9, wherein the antibody or antigen-binding fragment thereof:
   a) is alirocumab; or
   b) comprises the heavy and light chain complementarity determining regions (CDRs) of a heavy chain variable region/light chain variable region (HCVR/LCVR) amino acid sequence pair comprising SEQ ID NOs: 1/6.

2. The method of claim 1, wherein the initial (pre-treatment) frequency of apheresis is once a week or once every two weeks.

3. The method of claim 1, wherein the frequency of apheresis following administration of the one or more doses of the PCSK9 inhibitor is once every three weeks, once every four weeks, once every five weeks, or less frequent than once every five weeks.

4. The method of claim 1, wherein, following administration of the one or more doses of the PCSK9 inhibitor, the patient no longer requires apheresis to maintain the target lipoprotein level.

5. The method of claim 1, wherein the patient, prior to treatment with the one or more doses of the PCSK9 inhibitor, is diagnosed with heterozygous familial hypercholesterolemia (HeFH) or homozygous familial hypercholesterolemia (HoFH), and/or elevated lipoprotein(a) (Lp[a]).

6. The method of claim 1, wherein the lipoprotein apheresis therapy is selected from the group consisting of: cascade filtration, immunoadsorption, heparin-induced LDL precipitation, LDL-adsorption (dextran sulfate) liposorber, LDL hemoperfusion, and LDL-hemoperfusion (liposorber D).

7. The method of claim 1, wherein the patient, prior to or at the time of treatment with the one or more doses of the PCSK9 inhibitor, is on a stable lipoprotein apheresis schedule at the initial (pre-treatment) frequency for at least 2 weeks prior to administration of the first dose of the PCSK9 inhibitor.

8. The method of claim 1, wherein the patient is on a stable background lipid modifying therapy (LMT) prior to administration of the one or more doses of the PCSK9 inhibitor.

9. The method of claim 1, wherein the patient is on a stable background lipid modifying therapy (LMT) concurrent with administration of the one or more doses of the PCSK9 inhibitor.

10. The method of claim 8, wherein the stable background LMT is low-, moderate-, or high-dose statin therapy.

11. The method of claim 9, wherein the stable background LMT is low-, moderate-, or high-dose statin therapy.

12. The method of claim 1, wherein the lipoprotein that is lowered in the serum of the patient following administration of the one or more doses of the PCSK9 inhibitor is one or more lipoproteins selected from the group consisting of LDL-C, ApoB, non-HDL-C, total cholesterol, and Lp(a).

13. The method of claim 1, wherein the target lipoprotein level is a senior LDL-C level of less than 200 mg/dL, less than 130 mg/dL, less than 100 mg/dL, or less than 70 mg/dL.

14. The method of claim 1, wherein the antibody or antigen-binding protein that specifically binds PCSK9 is administered to the patient at a dose of about 150 mg at a frequency of once every two weeks.

15. The method of claim 14, wherein the antibody or antigen-binding protein is alirocumab.

16. The method of claim 1, wherein the antibody or antigen-binding fragment thereof comprises heavy and light chain CDR amino acid sequences having SEQ ID NOs: 2, 3, 4, 7, 8 and 10.

17. The method of claim 16, wherein the antibody or antigen-binding fragment thereof comprises an HCVR having the amino acid sequence of SEQ ID NO:1 and an LCVR having the amino acid sequence of SEQ ID NO:6.

* * * * *